United States Patent [19]
Lichtenberger et al.

[11] Patent Number: 5,955,451
[45] Date of Patent: *Sep. 21, 1999

[54] METHODS OF ENHANCING THE THERAPEUTIC ACTIVITY OF NSAIDS AND COMPOSITIONS OF ZWITTERIONIC PHOSPHOLIPIDS USEFUL THEREIN

[75] Inventors: Lenard Lichtenberger; Bruce D Butler, both of Houston, Tex.

[73] Assignee: The University of Texas System Board of Regents

[ * ] Notice: This patent is subject to a terminal disclaimer.

[21] Appl. No.: 08/719,134

[22] Filed: Sep. 24, 1996

Related U.S. Application Data

[63] Continuation-in-part of application No. 08/440,417, May 12, 1995, Pat. No. 5,763,422.
[51] Int. Cl.$^6$ .................................................. A61K 43/82
[52] U.S. Cl. ........................... 514/78; 514/171; 514/360; 514/547; 514/925; 424/78.05
[58] Field of Search .............................. 514/78, 171, 360, 514/925, 547; 424/78.05

[56] References Cited

U.S. PATENT DOCUMENTS

| | | |
|---|---|---|
| 4,279,906 | 7/1981 | Frosch ...................................... 424/247 |
| 4,309,420 | 1/1982 | Ghyczy et al. . |
| 4,332,795 | 6/1982 | Ghyczy et al. . |
| 4,369,182 | 1/1983 | Ghyczy et al. . |
| 4,378,354 | 3/1983 | Ghyczy et al. . |
| 4,421,747 | 12/1983 | Ghyczy et al. . |
| 4,528,193 | 7/1985 | Ghyczy et al. . |
| 4,684,632 | 8/1987 | Schulz et al. . |
| 4,687,766 | 8/1987 | Wendel et al. . |
| 4,918,063 | 4/1990 | Lichtenberger et al. . |
| 5,032,585 | 7/1991 | Lichtenberger . |

FOREIGN PATENT DOCUMENTS

| | | |
|---|---|---|
| 58-150508 | 9/1983 | Japan . |
| 63-048226 | 2/1988 | Japan . |
| 63-048228 | 2/1988 | Japan . |
| 3176425 | 7/1991 | Japan . |
| WO 96/.16920 | 11/1991 | WIPO . |

OTHER PUBLICATIONS

Author unknown, "Press Digest for Nature Medicine," *Nature Medicine*, pp. 1–4, in particular, p. 2, Feb., 1995.

Clarke, et al., "Antinociceptive effects of non–steroidal anti–inflammatory drugs in a rat model of unilateral hind-paw inflammation," *European Journal of Pharmacology* 257 (1994) 103–108.

Davis, et al., "Processed Aloe vera administered Topically Inhibits Inflammation," *Journal of the American Podiatric Medical Assocation*, vol. 79, No. 8 (Aug., 1989) 395–397.

Dial, et al., "Gastroprotective Activity of Dietary Lipids," *AGA Abstracts*, pp. A61, Apr., 1992.

Dialog Search Report, pp. 1–24, dated Jan. 9, 1995, 3:50 p.m.

Dialog Search Report, pp. 1–6, dated Jan. 9, 1995, 3:19 p.m.

Dialog Search Report, pp. 1–66, dated Jan. 9, 1995, 2:03 p.m.

Giraud, et al., "Zwitterionic phospholipids facilitate the transport of aspirin across artificial membranes," *Gastroenterology*, vol. 108, No. 4, A101, 1995.

Glenn, et al., "Simple Laboratory Procedures for the Evaluation of Topically–Active Anti–Inflammatory Drugs," *Agents and Actions*, vol. 8/5 (1978) 497–503.

Go, et al., "Gastric Mucosal Hydrophobicity and Helicobacter Pylori: Absence of a Direct Relation?" *AGA Abstracts:* 102(4) (Part 2), Apr., 1992.

Lichtenberger, et al., "ASA Forms An Ionic Complex With Phosphatidylcholine: Possible Molecular Explanation For Its Ulcergenic Action," *Gastroenterology*, vol. 104, No. 4, Part 2, A134, AGA Abstracts, 1993.

Lichtenberger, et al., "Certain NSAIDS Chemically Associate With Surface Phospholipids: Insight Into Mechanism And Reversal of NSAID–Induced Gastric Injury," *Gastroenterology*, vol. 106, A125, 1994.

Lichtenberger, et al., "NSAIDs complexed to phosphatidylcholine have reduced GI toxicity and enhanced bioavailability," *Gastroenterology*, vol. 108, No. 4, A149, 1995.

Lichtenberger, et al., "Effect of naproxen on gastric mucosal hydrophobicity: possible interaction with surface phospholipids," *Gastroenterology:* vol. 108, No. 4, A149, 1995.

Lichtenberger, et al., "Ammonium ($NH_{4+}$) Prevents the Denovo Formation of a Phospholipid (PL) Monolayer Surface: Is This the Basis of H. Pylori–Induced Reduction in Gastric Mucosal Hydrophobicity?" *AGA Abstracts*, pp. A653, Apr., 1992.

(List continued on next page.)

*Primary Examiner*—Keith D. MacMillan
*Attorney, Agent, or Firm*—Locke Liddell & Sapp LLP; Denise L. Mayfield

[57] ABSTRACT

Disclosed are compositions comprising non-steroid anti-inflammatory drugs (NSAID'S) complexed with zwitterionic, neutral phospholipids, or both, having reduced gastrointestinal irritating effects and enhanced antipyretic, analgesic, and antiinflammatory activity. Also disclosed are improved methods of using the complexes for treating fever, inflammation, and preventing platelet aggregation. In some embodiments, the anti-pyretic activity of sub-therapeutically used amounts of NSAID's are enhanced to elicit anti-pyretic activity in vivo when associated (noncovalently) with zwitterionic phospholipids, such as dipalmitoyl phosphatidyl choline. Methods and compositions useful for enhancing the therapeutic activity of non-steroidal anti-inflammatory agents in the presence of anti-secretory agents are also discussed.

16 Claims, 31 Drawing Sheets

OTHER PUBLICATIONS

Lichtenberger, et al., "Chronic Elevation of Intraluminal Ammonia Induces Gastroduodenal (G–D) Hypertrophy and a Defect in the Mucosal Barrier," AGA Abstracts, Apr., 1992.

Lichtenberger, et al., "Non–Steroidal Anti–Inflammatory Drugs (NSAIDs) Associate with Zwitterionic Phospholipids: Insight Into the Mechanism and Reversal of NSAID–Induced Gastrointestinal Injury," Nature Medicine, 1(2): 154–158, 1995.

Lichtenberger, et al, "Zwitterionic Phospholipids Enhance Aspirin's Therapeutic Activity, as Demonstrated in Rodent Model Systems," JPET, 277:1221–1227, 1996.

Rhone–Poulenc Rorer, Nattermann Phospholipid GMBH, "1. Lecithin: Definitions and Descriptions," Phospholipids and Liposomes, published after 1990.

Wang, "Zwitterionic Surfactant," Light Industrial Press, China (1991) A copy is not available; see I.D.S. for discussion).

International Search Report.

Liversidge, et al., "Influence of Indomethacin Amphoteric Gel on Gastric Ulcerogenicity and Absorption of Indomethacin In Rats," Pharm. Res., 6(1): 44–48, 1989, Database Chemical Abstracts on STN, AN 1989:107568.

Chemical Abstracts AN 1989: 107568, Liversidge et al, 1989.

Chemical Abstracts AN 1983:172935, Lind et al, 1983.

International Search Report, mailed May 1996.

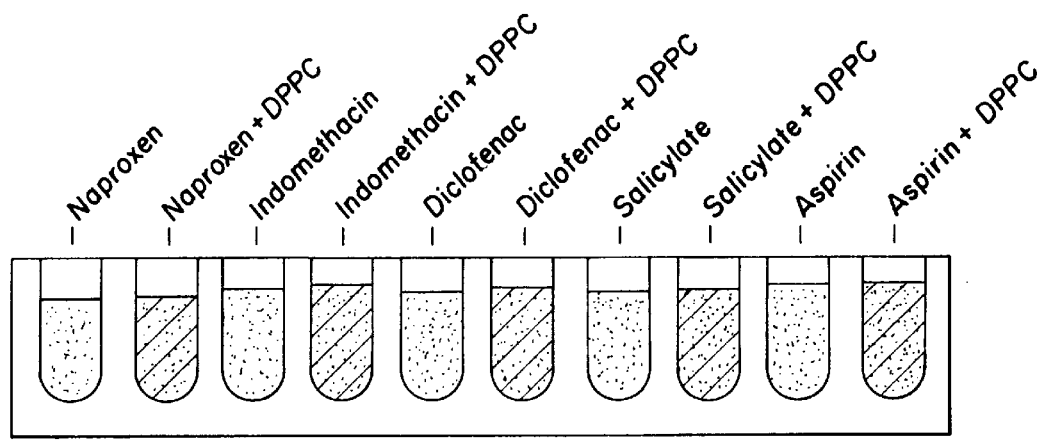
Fig. IA
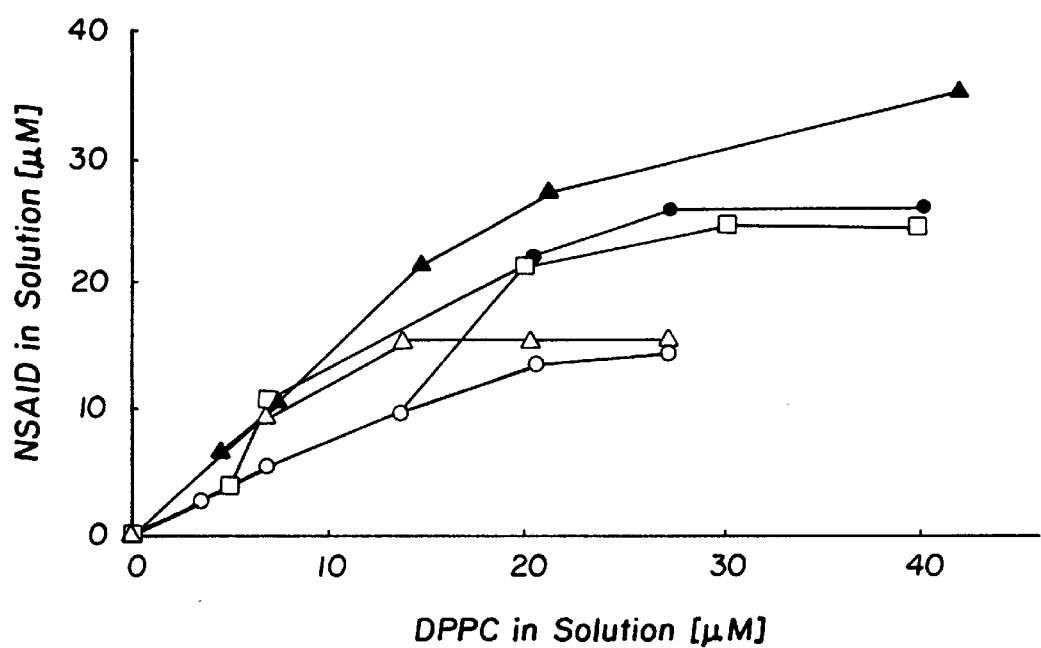
Fig. IB

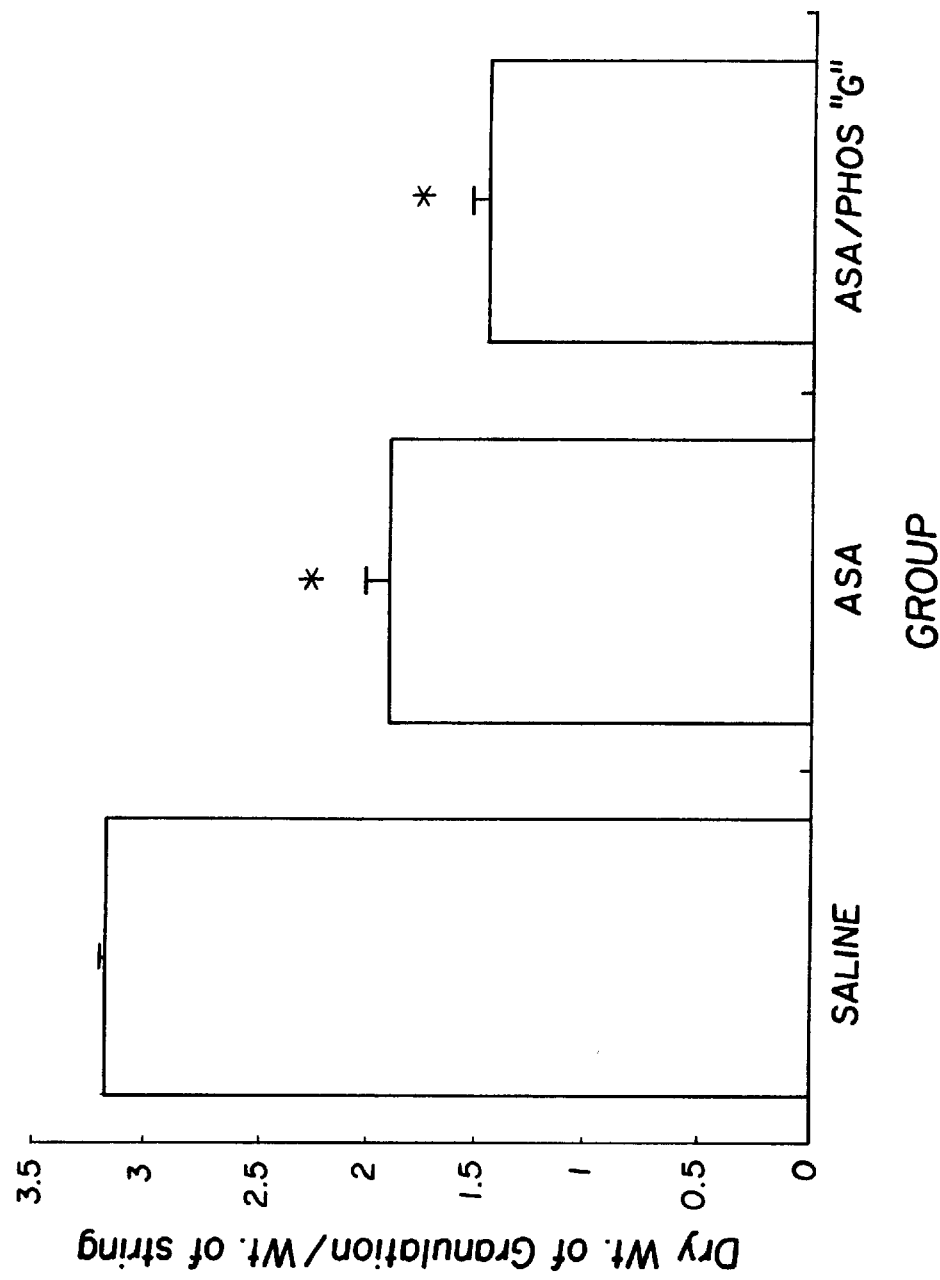

METHODS OF ENHANCING THE THERAPEUTIC ACTIVITY OF NSAIDS AND COMPOSITIONS OF ZWITTERIONIC PHOSPHOLIPIDS USEFUL THEREIN

The present application is a continuation-in-part of U.S. patent application Ser. No. 08/440,417, filed May 12, 1995, now U.S. Pat. No. 5,763,422.

The government owns rights in the present invention pursuant to grant number DK 33239 from the National Institute of Health.

BACKGROUND OF THE INVENTION

1. Field of the Invention

The present invention relates generally to the fields of pharmacology and medicine and more particularly, it concerns the treatment and prevention of fever, pain and inflammation with non-steroidal anti-inflammatory drugs (NSAIDs) complexed with phospholipids, and in other embodiments in further combination with neutral lipids. The invention also provides methods for retarding platelet aggregation, and the application of these methods in treating cardiovascular and vascular diseases as it relates to platelet activity.

2. Description of the Related Art

The consumption of NSAIDs among the general populace is unparalleled by any other drug class due to their great efficacy in the treatment of pain, inflammation and fever (Rainsford, 1985). The widespread usage of these drugs is anticipated to increase even further due to their efficacy in the treatment of osteoarthritic and generalized aches and pain as the elderly increase as a percentage of the population (Alexander et al., 1985; Jolobe and Montgomery, 1984), and as NSAIDs are employed in the treatment/prevention of stroke and cardiovascular disease.

The major concern with these developments relates to the tendency of NSAIDs to induce gastrointestinal (GI) mucosal lesions, perforations and bleeding resulting in significant morbidity and mortality, even in occasional NSAID users (Rainsford, 1989; Graham, 1989; Allison et al., 1992). Strategies to reduce the gastroduodenal injurious effects of these drugs with enteric coatings, have had limited success due to the delayed therapeutic actions of these specially packaged NSAIDs (Alpsten et al., 1982; Mojaverian et al., 1987).

Although it is clear that the GI side-effects of NSAIDs are in part attributable to their ability to inhibit the biosynthesis of gastroprotective prostaglandins, a significant amount of evidence exists that NSAIDs act locally on the mucosa to induce GI ulcers and bleeding by a prostaglandin-independent mechanism (Rainsford, 1989; Whittle et al., 1980; Whittle, 1981; Ligumsky et al., 1982; McCormack and Brune, 1987).

The present inventor and others have obtained evidence that the mucosa of the stomach and other regions of the GI tract have hydrophobic, non-wettable properties, that protect the underlying epithelium from gastric acid and other luminal toxins (Hills et al, 1983; Goddard et al., 1987; Goddard et al., 1990; Kao et al., 1990). This biophysical characteristic, which can be quantified by contact angle analysis, appears to be attributable to the presence of an extracellular lining of surfactant-like phospholipid on the luminal aspects of the mucus gel layer (Goddard et al., 1990; Kao et al., 1990). Evidence has also come forth that these zwitterionic phospholipids are synthesized in surface mucus cells of the stomach, as well as those present in discrete submucosal glands of the GI tract, where they are stored in specific organelles and secreted by a prostaglandin-dependent pathway (Kao and Lichtenberger, 1991). It has also been reported that aspirin and other NSAIDs have the ability to rapidly transform the gastric mucosa from a non-wettable to a wettable state within minutes after luminal administration, thereby increasing the tissue's susceptibility to the corrosive actions of gastric acid (Hills et al., 1983; Goddard et al., 1987; Goddard et al., 1990; Kao et al., 1990).

One solution to this problem has been to formulate injectable solutions of NSAIDs and thus bypass the GI tract completely. The low water solubility of these drugs, however, has caused problems with this technique. Stable, injectable solutions of indoleacetic and indanacetic acid derivatives have been developed to address this problem, by complexing these NSAIDs with phosphatidylcholine and phosphatidylethanolamine derivatives (See U.S. Pat. No. 4,309,420).

U.S. Pat. No. 4,421,747 describes NSAIDs complexed with phospholipids for oral administration. These complexes were shown to retain their antiinflammatory action and to have reduced ulcer formation in rats. However, no enhancement of therapeutic effects was reported with these preparations.

WO 91/16920 (Vical Inc.) relates to phospholipid prodrug derivatives of a salicylate or non-steroidal, anti-inflammatory drug. These preparations are made by combining salicylic acid or NSAID with a phospholipid in the presence of a coupling agent, thereby producing a covalently linked NSAID-phospholipid compound. These prodrugs are described as useful in reducing the toxicity of high dose, long term usage of NSAID preparations.

JP 3176425 (Nippon Shinyaku KK) relates to compositions including non-steroidal, anti-inflammatory drugs together with neutral lipids and phospholipids in a fat and oil emulsion. Although the method of preparation is not described in the abstract, these compositions appear to be encapsulated in lipid, such as in a micelle. The combination of the drug with the neutral lipids and the phospholipids is described as not affecting the drug's pharmacological actions.

JP 63048228 (Toa Eiyo KK) relates to topically applied compositions that include non-steroidal anti-inflammatory drug together with phospholipid and a "disintegrator". The disintegrator is described as providing for a preparation with improved dispersability and increased absorptivity. JP 63048226 (Ono Pharmaceutical KK) relates to compositions that include a phospholipid base (such as phosphatidylcholine) and an anti-inflammatory agent (such as acetylsalicylic acid and indomethacin). KK JP 58150508 (Ono Pharmaceutical) relates to topical compositions that include a phospholipid base (such as phosphatidylcholine) and an anti-inflammatory agent (such as acetylsalicylic acid and indomethacin).

U.S. Pat. No. 4,369,182 (Nattermann & CIE), relates to inflammation-preventing pharmaceutical compositions for oral administration. The compositions are prepared and then lyophilized into powder form. The described compositions include natural and synthetic phospholipids (dipalmitoylphosphatidylcholine (DPPC)), in combination with nonsteroidal agents including salicylic acid, acetyl-salicylic acid, diflunisal, indomethacin, glucametacine, acemetacin, sulindac, ibuprofen, naproxen, tolmetin and other NSAID's. Also described are NSAID's in combination with phosphatidylcholine preparations, named phospholipons. U.S. Pat. No. 4,421,747 relates to methods of alleviating inflammation with compositions as described in the '182 patent.

Despite the extensive work in the area of NSAIDs, a need continues to exist in the art for preparations that include reduced amounts of this useful class of drug without loss of therapeutic efficacy. Methods and compositions that provide for similar or enhanced anti-pyretic, anti-inflammatory, anti-platelet and analgesic activity at lower doses than currently prescribed for pharmacological activity would also render this very valuable class of drugs available to those previously unable to tolerate standard and/or prolonged therapeutic regimens of NSAID.

SUMMARY OF THE INVENTION

The present invention seeks to overcome these and other drawbacks inherent in the prior art by providing compositions and methods capable of maintaining and/or improving the pharmacological activity of non-steroidal antiinflammatory drugs by noncovalent association with zwitterionic phospholipids. In some embodiments, these preparations may further include neutral lipids, such as the triglycerides.

The present invention illustrates the ability of one or more zwitterionic phospholipids to enhance the fever-reducing potential of an NSAID. Pharmacological activity of low dose NSAID to reduce inflammation and pain may also be observed, and in some cases enhanced by chemically associating the NSAID with zwitterionic phospholipid, such as phosphatidyl choline (PC), dipalmitoylphosphatidylcholine (DPPC), and other disaturated phosphatidyl cholines, and the like. In some embodiments, the association of NSAID and zwitterionic phospholipid is of a non-covalent nature. In still other embodiments, the NSAID and zwitterionic phospholipid compositions may be further described as including more or less equimolar amounts of these ingredients. The compositions may also, of course, comprise a pharmaceutically acceptable carrier in any form, such as solid powder, gel or liquid form.

The present invention focusses techniques that are demonstrated in some cases to enhance the therapeutic activities of NSAIDs. This is accomplished without the disadvantage of hindering the pharmacological activity or therapeutic bioavailability of the drug rendering the preparations effective even at low doses.

Accordingly, the present invention provides in one aspect a method for enhancing the antipyretic activity of a nonsteroidal anti-inflammatory drug (NSAID). This method comprises providing a non-covalently associated combination of a zwitterionic phospholipid with an amount of a nonsteroidal anti-inflammatory drug that provides reduced anti-pyretic activity in the absence of the zwitterionic phospholipid. Some embodiments of the present preparations are further described as being essentially free of anionic phospholipid, or as including an amount of anionic phospholipid that is biologically inert and/or not an active component, of the preparation.

The term "essentially free" as used in the description of the present invention, is understood to mean compositions that include less than about 0.10% of anionic phospholipid, and in even further defined embodiments, less than 0.01% anionic phospholipid. As used in the description of the present invention, the term zwitterionic phospholipid embraces a wide range of phospholipids, including but not limited to phosphatidylcholine, phosphatidylserine, phosphalidylethanolamine, sphingomyelin and other ceramides, as well as various other zwitterionic phospholipids. In some embodiments, these compositions are essentially free of anionic phospholipid.

In other embodiments of the described method, the amount of nonsteroidal anti-inflammatory drug is defined as an amount that provides reduced antipyretic activity in the absence of the zwitterionic phospholipid. Such amounts of the drug sub-therapeutically effective amounts thereof. This activity or lack of activity is observed in the absence of zwitterionic phospholipid, while the same or about the same amount of the NSAID does demonstrate pharmacological activity in the presence of zwitterionic phospholipid. In this regard, the phenomenon is observed that the combination of low amounts of nonsteroidal anti-inflammatory drugs with phospholipid have potent pharmacological activity, while doses of the drug alone (i.e., without zwitterionic phospholipid) do not.

The present method employs compositions that may include any variety of those drugs generally classified as nonsteroidal anti-inflammatory drugs. By way of example, these drugs include ibuprofen, piroxicam, salicylate, aspirin, naproxen, indomethacin, diclofenac, or any mixture thereof. In particular embodiments, the nonsteroidal anti-inflammatory drug is salicylate. By way of example and not limitation, NSAID's useful in the practice of the invention, include those noted in Table 1.

TABLE 1

Nonsteroidal Anti-Inflammatory Drugs To Be Used in Combination with Zwitterionic Phospholipids

| | | |
|---|---|---|
| Propionic acids | Fenoprofen calcium | Nalfon ® |
| | Flurbiprofen | Ansaid ® |
| | Suprofen | |
| | Benoxaprofen | |
| | Ibuprofen (prescription) | Motrin ® |
| | Ibuprofen (200 mg. over the counter) | Nuprin, Motrin 1B ® |
| | Ketoprofen | Orduis, Oruvall ® |
| | Naproxen | Naprosyn ® |
| | Naproxen sodium | Aleve, Anaprox, Aflaxen ® |
| | Oxaprozin | Daypro ® |
| Acetic acids | Diclofenac sodium | Voltaren ® |
| | Diclofenac potassium | Cataflam ® |
| | Etodolac | Lodine ® |
| | Indomethacin | Indocin ® |
| | Ketorolac tromethamine (intramuscular) | Acular, Toradol ® |
| | Ketorolac (oral) | Toradol ® |
| Ketones | Nabumetone | Relafen ® |
| | Sulindac | Clinoril ® |
| | Tolmetin sodium | Tolectin ® |
| Fenamates | Meclofenamate sodium | Meclomen ® |
| | Mefenamic acid | Ponstel ® |
| Oxicams | Piroxicam | Dolibid ® |
| Salicylic acid | Diflunisal | Feldene ® |
| | Aspirin | |
| Pyrazolin acid | Oxyphenbutazone | Tandearil ® |
| | Phenylbutazone | Butazolidin ® |

NSAIDs such as benoxaprofen, ketoprofen, oxaprozin, etodolac, ketorolac tromethamine, ketorolac and nabumetone, together with zwitterionic phospholipid, comprise still other particular embodiments of the invention, again both with and without neutral lipid.

In particular embodiments, the zwitterionic phospholipid in the compositions is dipalmitoyl phosphatidylcholine, phosphatidyl choline, or a mixture thereof.

The pharmacological, particularly anti-pyretic, activity of NSAIDs, is shown to be enhanced several-fold over preparations with similar doses without zwitterionic phospholipid. Surprisingly, the present inventors have found that combination of the aforedescribed nonsteroidal anti-inflammatory drugs with zwitterionic phospholipid dramatically enhances the anti-pyretic activity and potency of the drug, even at sub-therapeutically active doses, and in some cases from about 2-fold to about 6-fold relative to non-phospholipid containing preparations. Hence, the methods are expected to be particularly efficacious in reducing fever in a mammal having reduced tolerance for NSAID's.

Amounts ranging between one-tenth and one-half that typically necessary to illicit a fever-reducing response in a mammal may thus be realized employing the present inventive methods and compositions. In this regard, it is expected that amounts of between 2 mg/kg to about 300 mg/kg will provide fever-reducing therapeutic activity. Of course, the amount/dose used will depend in specific cases on the particular pharmacological characteristics of the NSAID or combination of NSAIDs included. Further defined ranges of the drug expected to provide the anti-pyretic activity herein disclosed range from between about 10 to about 150 mg/kg or about 20 or 50 mg/kg to about 150 mg/kg.

The present inventors have also observed the claimed compositions are useful for enhancing the platelet retarding activity of a non-steroidal anti-inflammatory drug. This method for inhibiting platelet aggregation comprises providing a non-covalently associated combination of zwitterionic phospholipid and an amount of non-steroidal anti-inflammatory agent that provides reduced inhibition of platelet aggregation in the absence of zwitterionic phospholipid. In some embodiments, this composition is essentially free of anionic phospholipid and/or includes an amount of anionic phospholipid that is a biologically inert component of the preparation. The amounts of non-steroidal anti-inflammatory drug employed as part of the composition, again, is relatively low, and may be further described as an amount that generally provides reduced pharmacological activity in the absence of zwitterionic phospholipid. Again, the zwitterionic phospholipid of choice is, in some embodiments, DPPC, PC, or a combination thereof.

The compositions of the aforedescribed methods may further include a neutral lipid, such as a triglyceride. For a partial listing of representative neutral lipids, such as the triglycerides, reference is specifically made to U.S. Pat. Nos. 4,950,656 and 5,043,329. Both saturated and unsaturated triglycerides may be employed in the present compositions, and include such triglycerides as tripalmitin (saturated), triolein and trilinolein (unsaturated). However, these particular triglycerides are listed here for convenience only, and are merely representative of a variety of useful triglycerides, and is further not intended to be inclusive.

Turning now to another aspect of the invention, methods for enhancing the analgesic activity of a non-steroidal anti-inflammatory drug are provided. These methods again comprise providing a non-covalently associated composition comprising zwitterionic phospholipid and an amount of a non-steroidal anti-inflammatory drug that provides reduced pharmacological activity in the absence of zwitterionic phospholipid. In some embodiments, these compositions are essentially free of anionic phospholipid, or include amounts of anionic phospholipid that are biologically inert. In particular embodiments, the nonsteroidal anti-inflammatory drug is one or more of those listed in Table 1. In particular embodiments, the NSAID is aspirin, salicylate, a salt thereof, or a combination thereof. While any of a number of different zwitterionic phospholipids may be employed in the composition of the method, in some embodiments, the phospholipid is dipalmitoyl phosphatidyl choline, phosphatidyl choline, or a combination thereof. In these and other embodiments of the described method, an anionic phospholipid that may be excluded or included only in biologically inert amounts is phosphatidyl glycerol (PG).

In still another aspect, the invention provides methods of enhancing the anti-inflammatory activity of non-steroidal anti-inflammatory drugs. The method comprises proving a non-covalently associated combination of zwitterionic phospholipid with an amount of a non-steroidal anti-inflammatory drug. The amount of NSAID in the composition is again defined as an amount that provides reduced pharmacological activity in the absence of zwitterionic phospholipid. In some embodiments, the method employs compositions that are essentially free of anionic phospholipids, such as the DPPG or PG, or includes amounts of anionic phospholipid that are biologically and pharmacologically inert.

In particular embodiments, the composition is further defined as comprising an equimolar amount of NSAID and zwitterionic phospholipid. The present inventors' studies demonstrate the described combination of ingredients provides an enhancement of the anti-inflammatory activity and potency of these drugs compared to drug preparations that do not include zwitterionic phospholipid. Also demonstrated is the reduction in anti-inflammatory activity observed where pharmacologically active (i.e., non-biologically insert amounts) amounts of anionic phospholipid, such as PG (PI), are included in the preparation. Hence, preparations that include pharmacologically active amounts of DPPG or PI would not necessarily provide for the same enhanced anti-inflammatory activity, or the aforedescribed enhanced pharmacological activity (i.e., antipyretic or enhanced reduction in platelet aggregation activity), described in the present methods. Pharmacologically active amounts of other negatively-charged phospholipids would also not be contemplated as particularly useful in view of these results.

Turning now to still a further aspect of the present invention, a method for enhancing the antipyretic potential of subtherapeutically effective amounts of nonsteroidal anti-inflammatory drug is disclosed. In some embodiments, the method comprises again combining zwitterionic phospholipid with an amount of non-steroidal anti-inflammatory drug to provide a noncovalently associated composition thereof. In some embodiments, the composition is further defined as essentially free of biologically active amounts of anionic (or negatively charged) phospholipid.

As used in the description of the above method, a subtherapeutically effective amount of NSAID is defined as an amount that provides reduced antipyretic activity in the absence of a zwitterionic phospholipid. The enhancement in activity of low amounts of NSAID illustrated in the various in vivo studies disclosed herein demonstrate that while doses of aspirin of about 9 mg/kg in combination with the zwitterionic phospholipid, DPPC, did provide for a fever reducing (anti-pyretic) pharmacologic response, treatment with this same dose of NSAID without phospholipid did not.

The present invention also discloses particular pharmaceutical preparations. These pharmaceutical preparations are further described as suitable for enteral or oral administration, and comprise a non-covalently associated combination of zwitterionic phospholipid, non-steroidal anti-inflammatory drug, and a pharmaceutically acceptable carrier. These compositions are formulated to provide a non-covalently linked composition that is further described as being essentially free of biologically active (pharmacologically active) amounts of anionic phospholipid, and in some embodiments, essentially free of DPPG.

In some applications, the non-steroidal anti-inflammatory drug is one or more of those listed in Table 1, such as naproxen, indomethacin, diclophenac, salicylate, aspirin, or any mixture thereof. In particular embodiments, the nonsteroidal anti-inflammatory drug of choice is salicylate. While any variety of zwitterionic phospholipids may be employed alone or in combination with the described drugs, some of the representative phospholipids include phosphatidyl choline, dipalmitoyl phosphatidylcholine, phosphatidyl serine, other zwitterionic phospholipids, or mixtures thereof. The compositions may further include a neutral lipid, such as a triglyceride. Representative triglycerides are described in U.S. Pat. No. 4,950,656, which reference is specifically incorporated herein by reference for this purpose. In particular embodiments, the pharmaceutical preparation is defined as comprising an equimolar amount of zwitterionic phospholipid and NSAID.

In yet another aspect, the present invention provides a method of maintaining and/or enhancing the therapeutic activity of a non-steroidal anti-inflammatory drug in the presence of a drug that reduces or inhibits gastric secretion. In one embodiment, the method comprises administering a combination of a non-steroidal anti-inflammatory agent and a zwitterionic phospholipid to an animal having received an anti-secretory agent. By way of example, drugs that reduce or inhibit gastric acid secretion in an animal include omeprazole.

The present invention also provides methods for maintaining or enhancing therapeutic activity of a non-steroidal anti-inflammatory agent in the presence of an H2 receptor blocker. In some embodiments, the method comprises administering the anti-inflammatory agent in association with a zwitterionic phospholipid to the animal having received an H2 receptor blocker, wherein the pH of the gastric secretions in the animal are maintained at fasting levels. As used in the description of the present invention, fasting levels are defined as a pH of about a pH 1 to about pH 4. By way of example, H2 receptor blockers include Zantac, Tagamet, nizetidine, as well as those agents listed at Table 7.

The present invention further provides a method for maintaining and/or enhancing the bio-availability of a non-steroidal anti-inflammatory drug in an animal. In some embodiments, the method comprises administering a combination of a non-steroidal anti-inflammatory agent and a zwitterionic phospholipid to an animal having received an anti-secretory agent, wherein the pharmacological activity of the NSAID is greater than the pharmacological activity of the non-steroidal anti-inflammatory agent administered in the absence of a zwitterionic phospholipid. activity in an animal receiving an anti-secretory agent.

The present invention further provides a pharmaceutical preparation comprising a non-covalently associated combination of a non-steroidal anti-inflammatory agent, zwitterionic phospholipid, and an agent that reduces or inhibits gastric acid secretion. Such agents include, by way of example, anti-secretory agents. By way of example, such anti-secretory agents include omeprazole. Such agents include both proton pump inhibitors (e.g. lansoprazole), and H2 receptor antagonists.

As used herein, "pharmaceutically acceptable carrier" includes any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

As used in the description of the present invention, the term "subtherapeutically effective amount", particularly as it is used to described the amount of NSAID employed, is defined as an amount of the NSAID that provides reduced pharmacological (i.e., anti-pyretic) activity in the absence of non-covalent association with a zwitterionic phospholipid.

It is understood that as used in the present disclosure and appended claims, the terms "a" and "an," as in "an element" or "a molecule" are intended to include one or more items or elements, and in no way limit the description or claimed element to one element or item.

The following abbreviations are employed in the description of the invention:

PI=phosphatidyl inositol
PC=phosphatidylcholine
PG=phosphatidylglycerol
L-NAME=N-nitro-L-arginine Methyl Ester

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Photograph of test tubes containing 30 nM of the sodium salts of one of the five NSAIDs tested in chloroform in the absence and presence of 30 nM DPPC (naproxen, indomethacin, diclofenac, salicylate, aspirin).

FIG. 1B. The concentration of each NSAID in solution increases (quantified by UV absorption) in proportion to the molar equivalents of DPPC dissolved in chloroform (Naproxen=-▼-; Aspirin=-•-; Salicylate=-□-, Diclofenac=-Δ-; Indomethacin=-○-).

represents a statistically significant difference between the values of rats treated with the NSAID alone (–DPPC) and those treated with the NSAID/DPPC complex (+DPPC) (Saline=-●-; ASA=-□-; ASA/DPPC=-○-).

FIG. 5. Anti-inflammatory action of ASA and Phospholipon G™ (Phospholipid "G") as determined by the implanted string assay as described. Dosage is 90 mg/kg ASA. Each bar represents data for n=5 rats.

Figure 6:
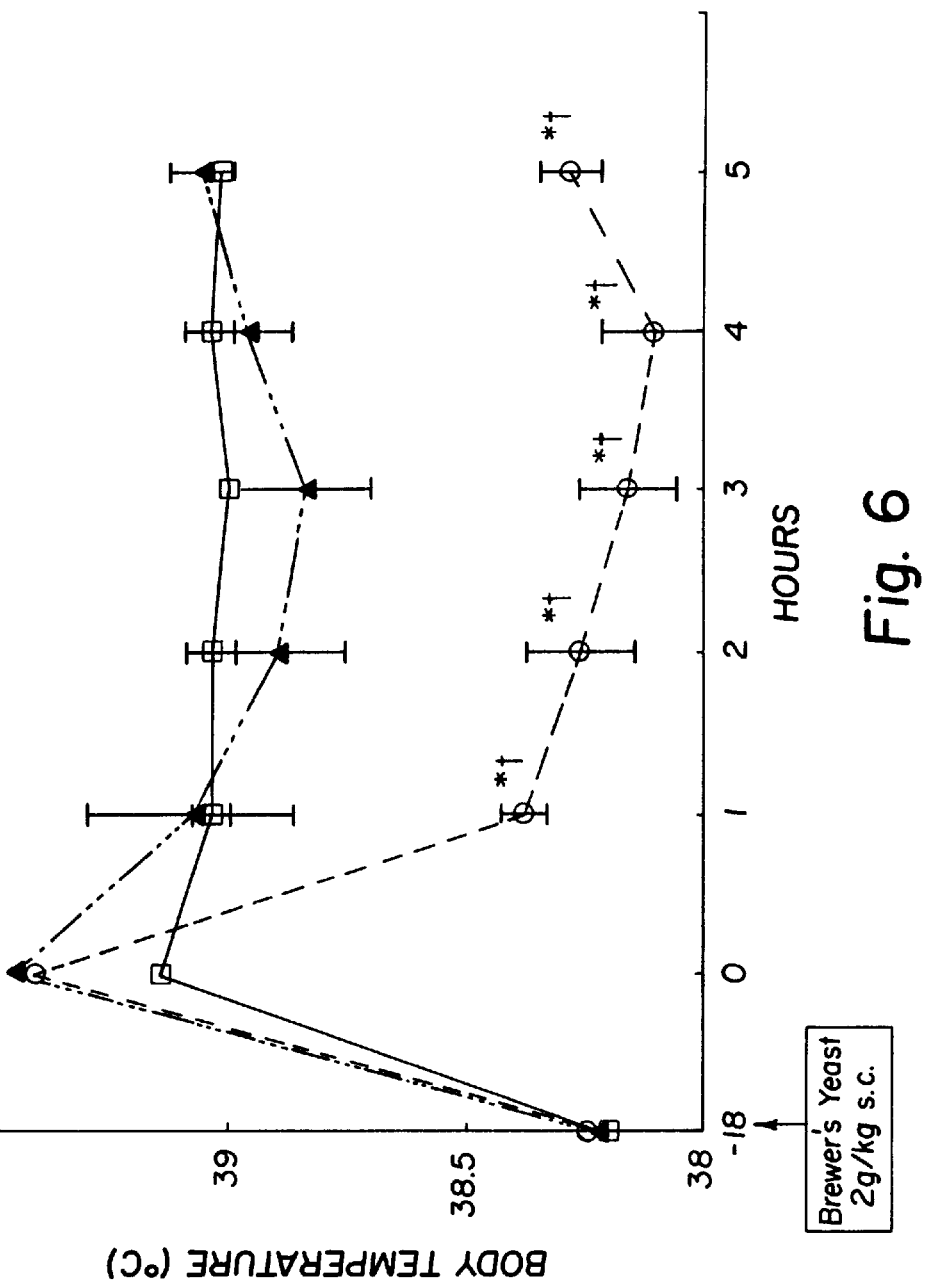

FIG. 6. Antipyretic activity of ASA\DPPC complex at a subthreshold ASA dosage (9.0 mg/kg) (Saline=-□-; ASA (9.0 mg/kg)=-▼-; ASA/DPPC (9 mg/kg)=-○-).

Figure 7:
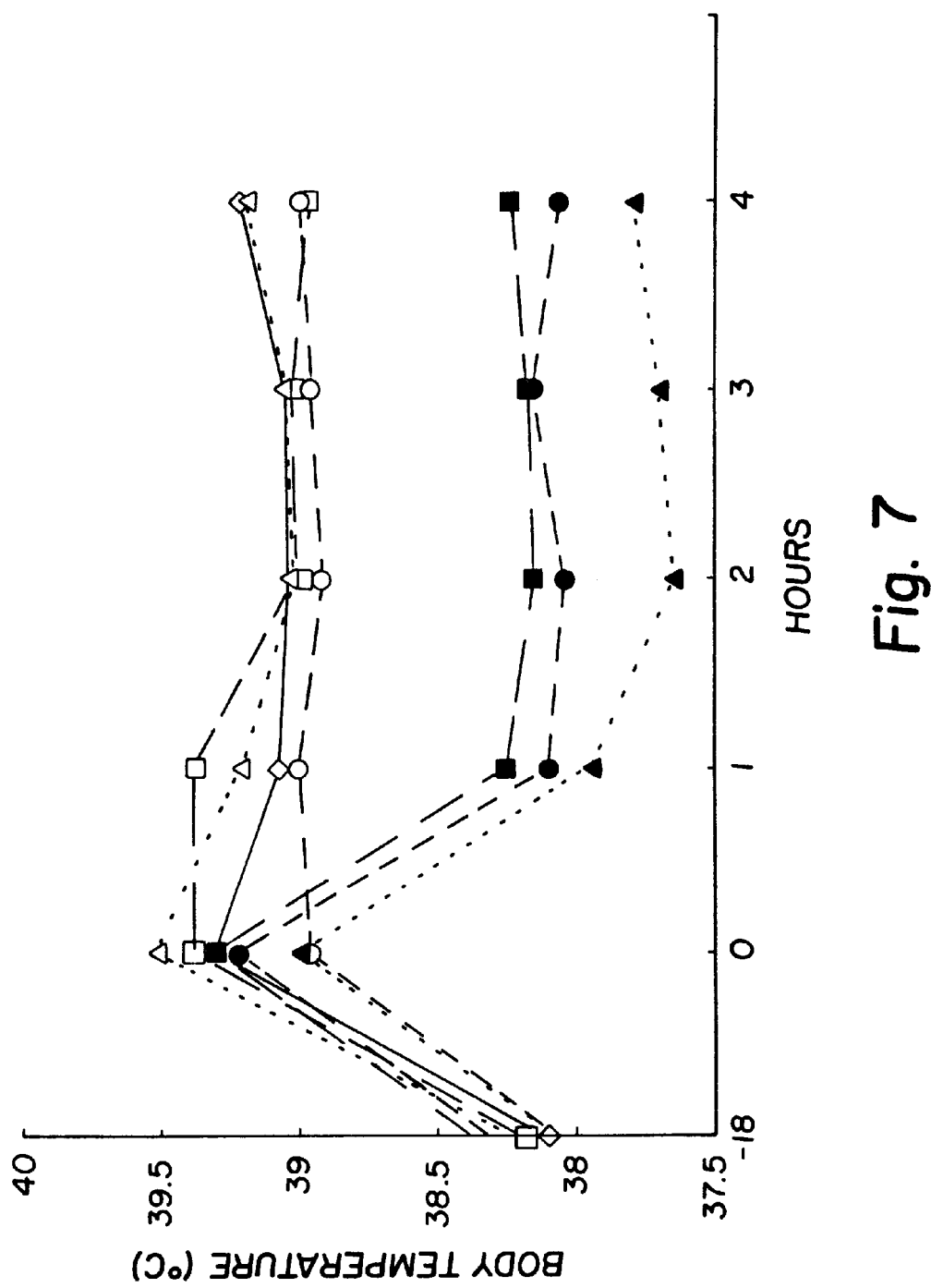

FIG. 7. Antipyretic activity of aspirin (ASA) alone when administered at doses which range from 2.5–90.0 mg/kg. In this and all subsequently figures the test agents were intragastrically administered 18 hrs after the rats were subcutaneously injected with 2 g/kg Brewer's Yeast to induce a 0.5–1.0° C. increase in body temperature. It can be appreciated that doses of aspirin of <10 mg/kg failed to reduce the fever during the 4 hour study period (Saline=-◊-; ASA, 2.5 mg/kg=-□-; ASA, 5 mg/kg=-○-; ASA, 10 mg/kg=-Δ-; ASA, 20 mg/kg=-■-; ASA, 45 mg/kg=-●-; ASA, 90 mg/kg=-▼-).

Figure 8:
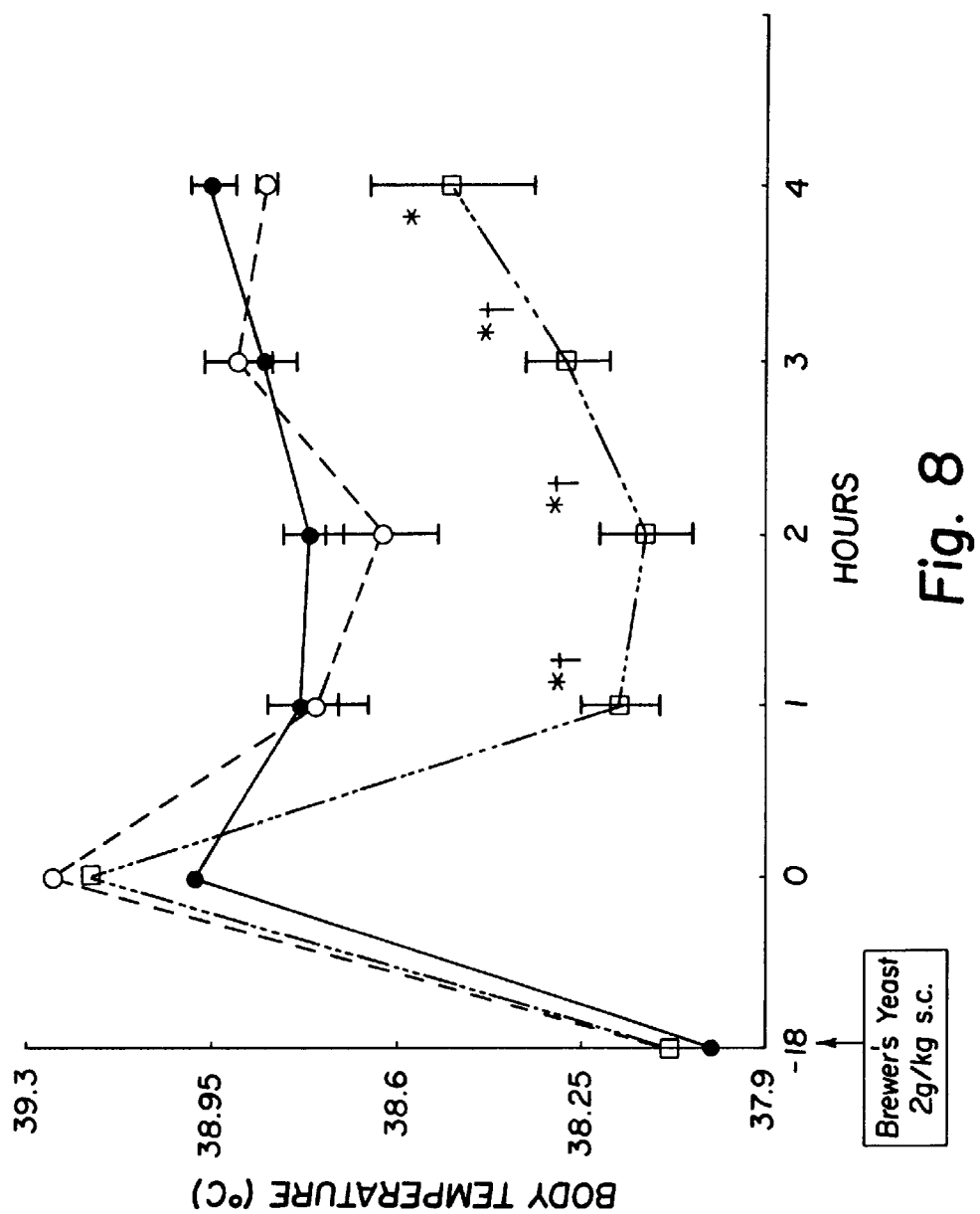

FIG. 8. In contrast to the above pattern aspirin (ASA) when complexed with an equimolar concentration of dipalmitoylphosphatidylcholine (DPPC) effectively reduced fever at a dose of 9.0 mg/kg, whereas the anionic phospholipid, DPPG, failed to augment aspirin anti-pyretic activity at this same sub-threshold dose. This figure also demonstrates that anionic phospholipid is essentially biologically inert in terms of enhancing the anti-pyretic action of aspirin (ASA, 9.0 mg/kg=-●-; ASA/DPPC, 9.0 mg/kg=-□-; ASA/DPPG, 9.0 mg/kg=-○-; n=5/grp; *=$p<0.05$ vs ASA; †=$p<0.05$ vs ASA/DPPG).

Figure 9:
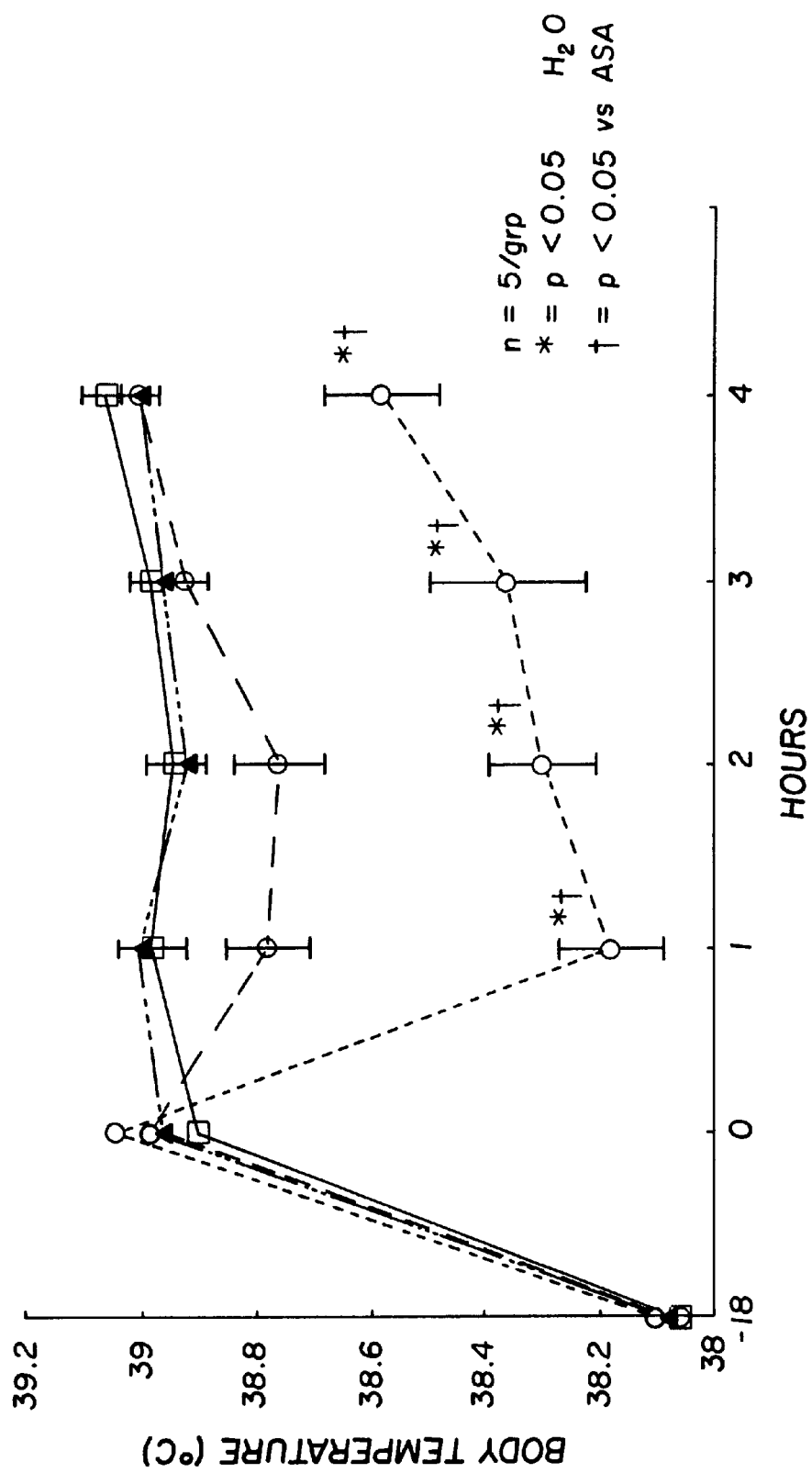

FIG. 9. ASA at a subthreshold dose of 4.5 mg/kg, which had no antipyretic activity alone, effectively reduced fever when complexed with an equimolar concentration of DPPC ($H_2O$=-□-; $H_2O$/DPPC (4.5 mg/kg)=-▼-; ASA (4.5 mg/kg)=-⊖-; ASA/DPPC (4.5 mg/kg)=---○---).

Figure 10:
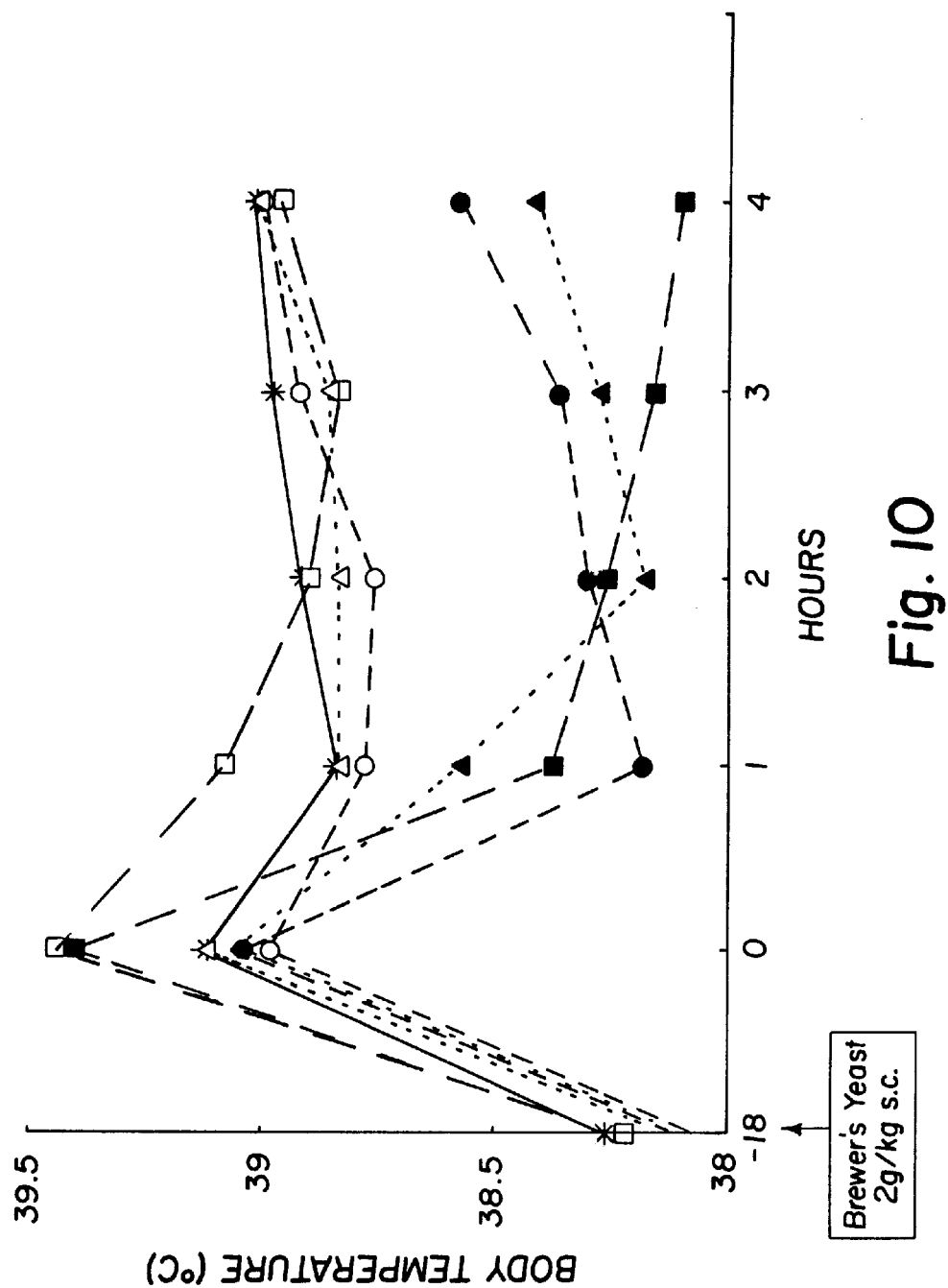

FIG. 10. Compilation of all the data at subthreshold doses (2.5–9.0 mg/kg) of ASA. ASA alone (open symbols) data demonstrates the enhancement of antipyretic activity when ASA was complexed to DPPC (closed symbols) (Saline=-*-; ASA, 9 mM=-□-; ASA, 4.5 mM=-○-; ASA, 2.5 mM=---Δ---; ASA/DPPC, 9 mM=-■-; ASA/DPPC, 4.5 mM=-●-; ASA/DPPC, 2.25 mM=---▼---).

Figure 11:
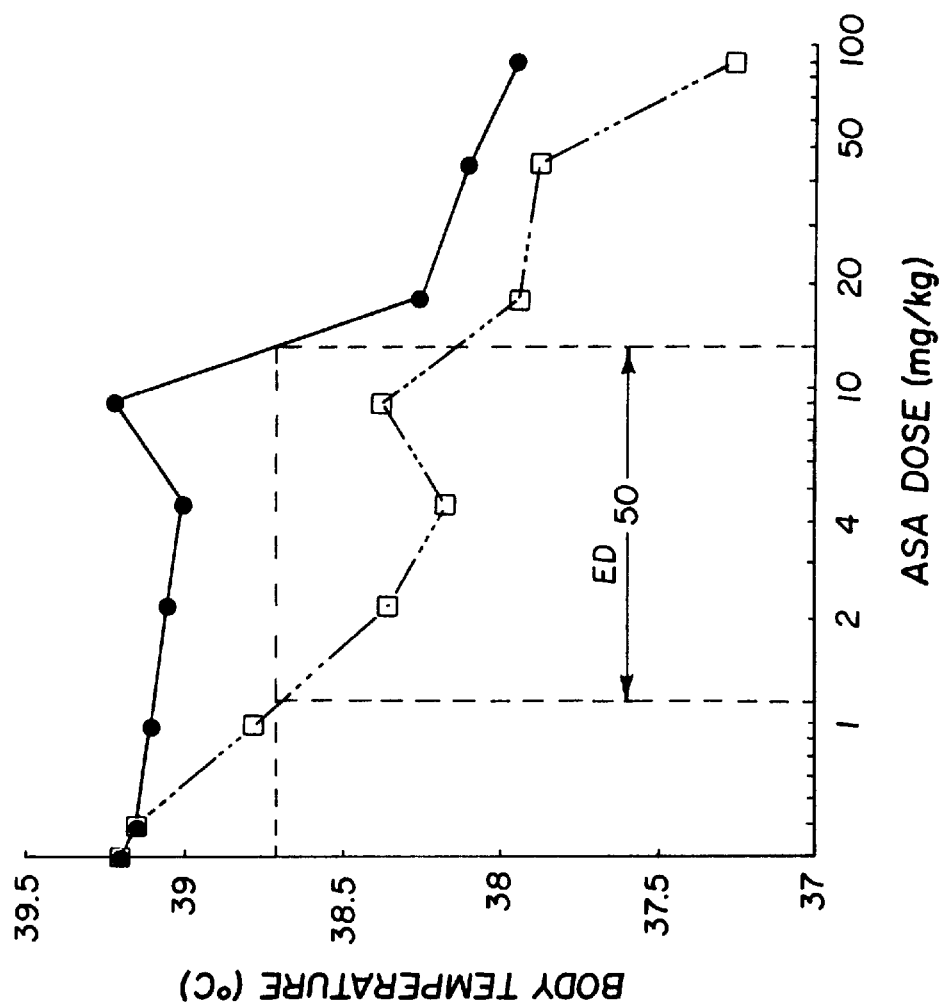

FIG. 11. Dose-response analysis of the antipyretic activity of ASA alone and the ASA/DPPC (equimolar ratio) complex 1 hr (FIG. 11) (ASA=-●-; ASA/DDPC=-□-) after intragastric administration. The potency of the ASA, as reflected by the $ED_{50}$ is increased ~10 fold when it is administered with the zwitterionic phospholipid.

Figure 12:
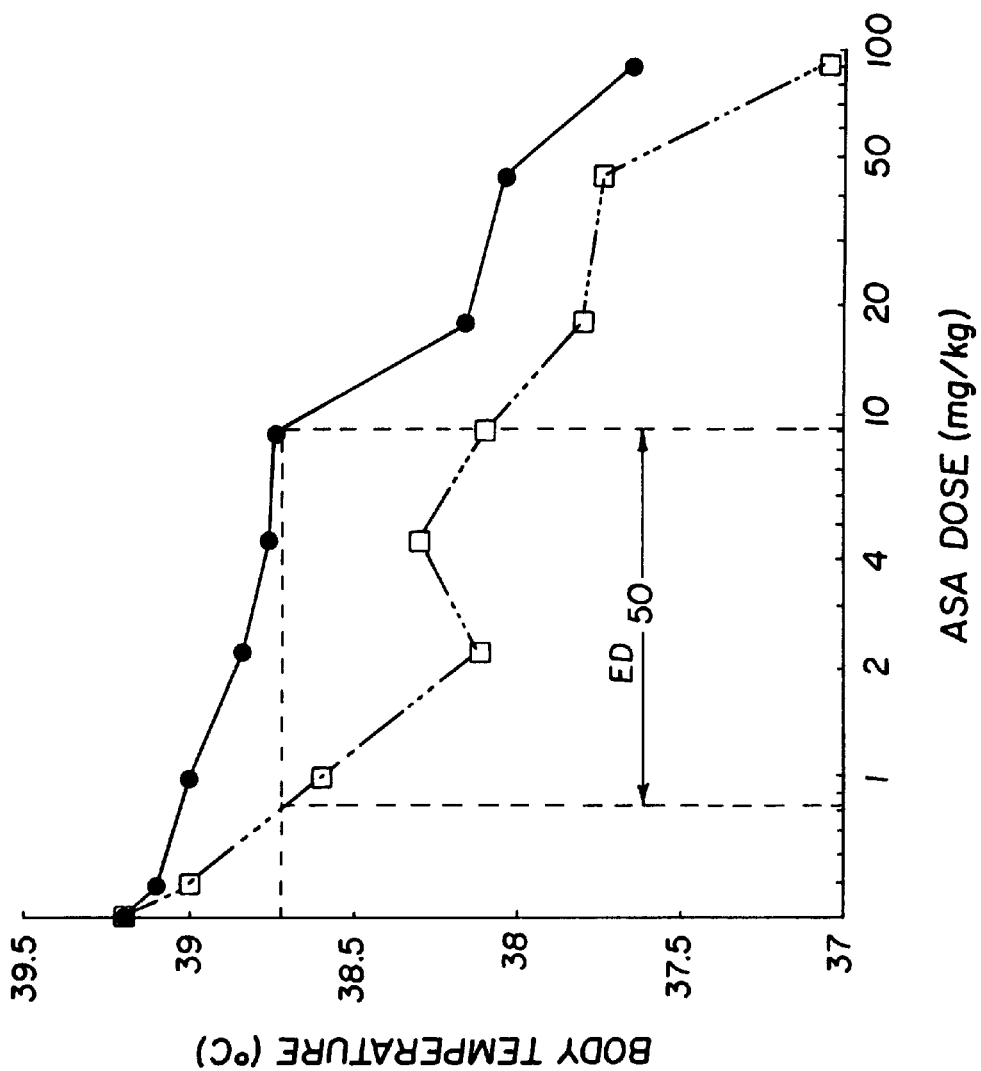

FIG. 12. Dose response analysis of the anti-pyretic activity of ASA alone and the ASA/DPPC (equimolar ratio) complex 2 hours after intragastric administration.

Figure 13:
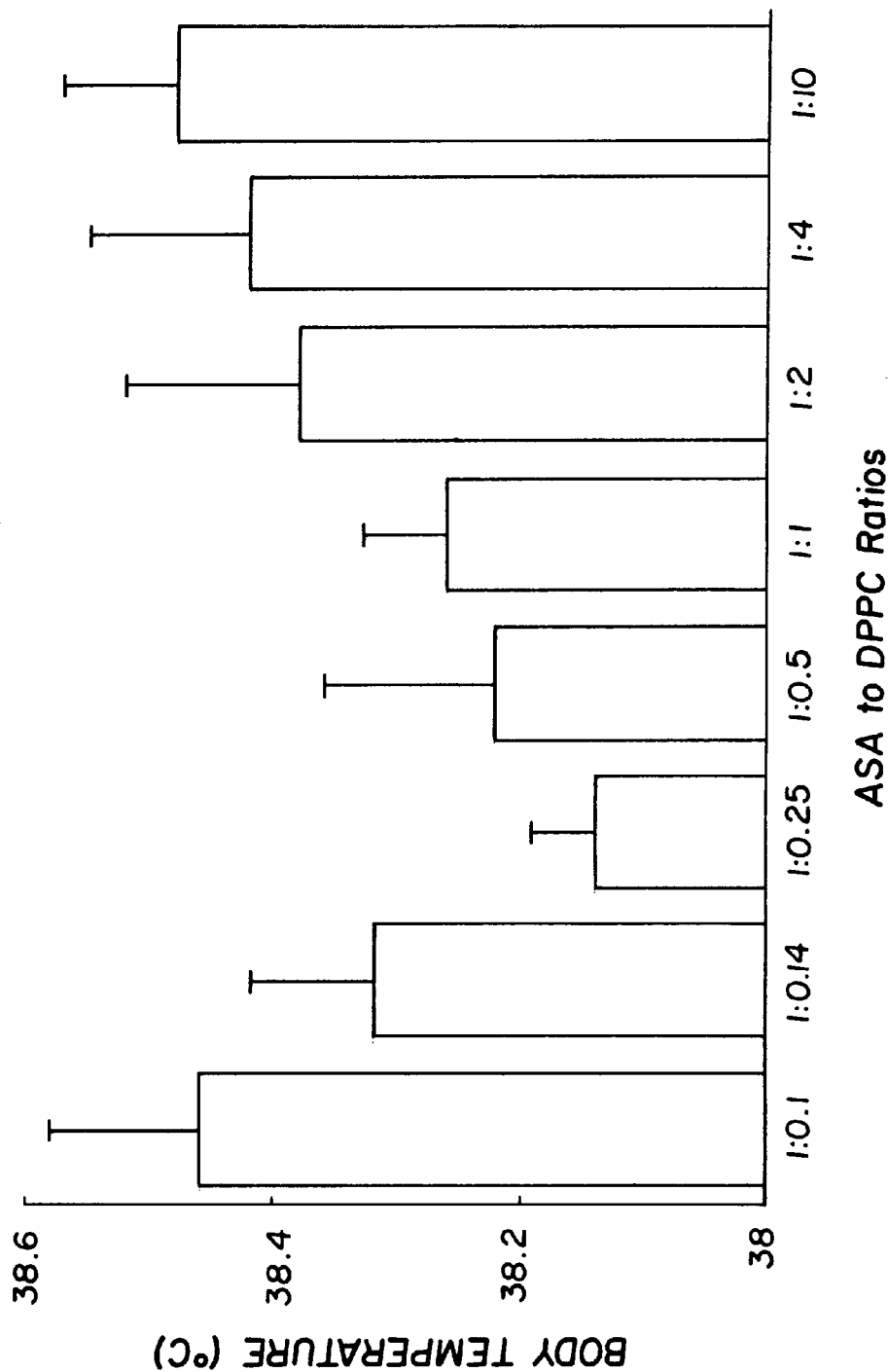

FIG. 13. Effect of varying the ASA:DPPC ratio from 1:1 on antipyretic activity at 1 hr post intragastric administration. It can be appreciated that the ability of the zwitterionic phospholipid to enhance the antipyretic activity of ASA was lost when the molar concentration of DPPC was increased (from unity) by a factor of 4 or decreased by a factor of 10 (ASA=9.01 mg/kg).

Figure 14:
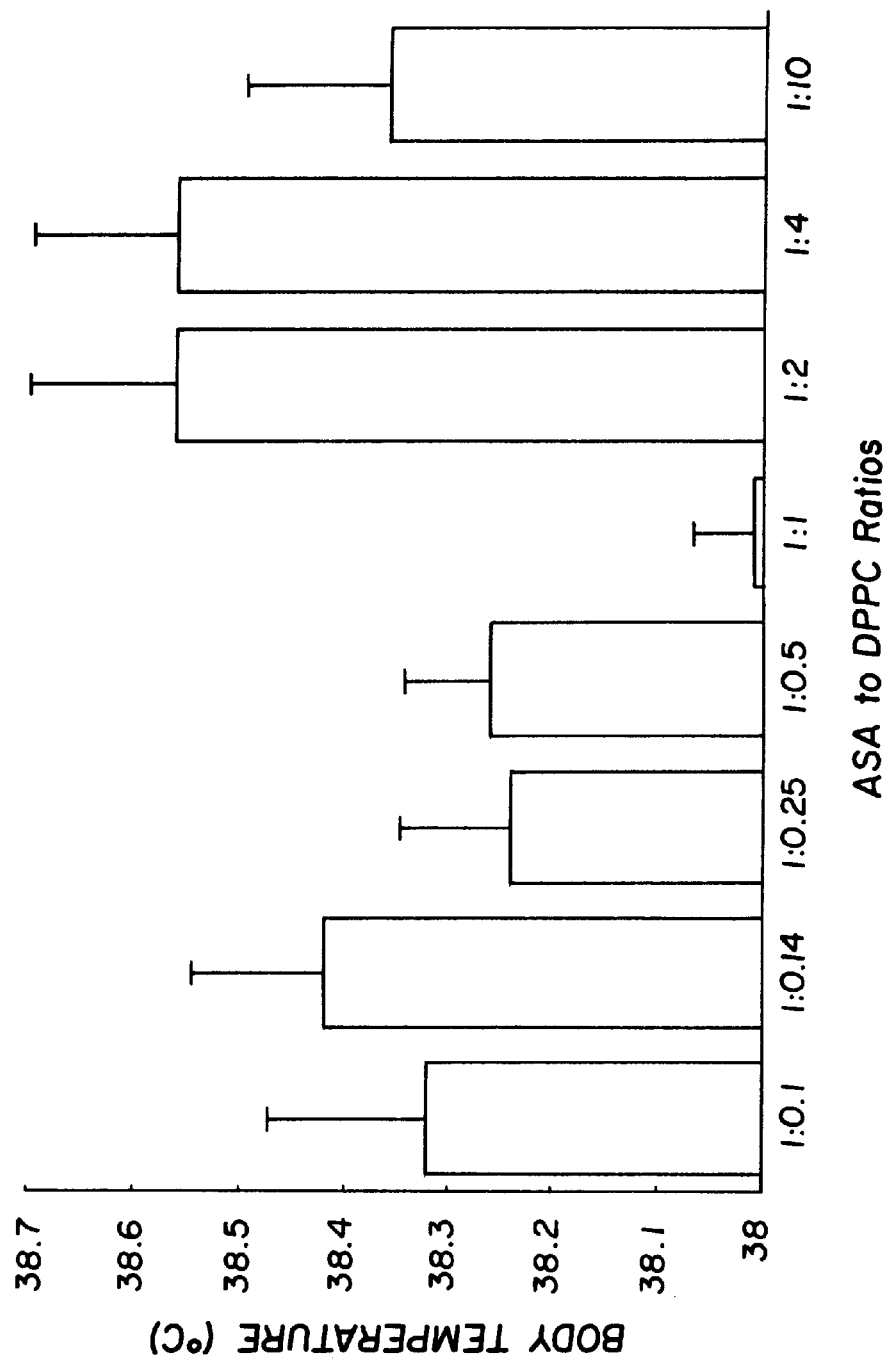

FIG. 14. Effect of varying the ASA:DPPC ratio from 1:1 on the antipyretic activity of the complex 2 hours post intragastric administration (Legends same as in FIG. 13) (ASA=9.01 mg/kg).

Figure 15:
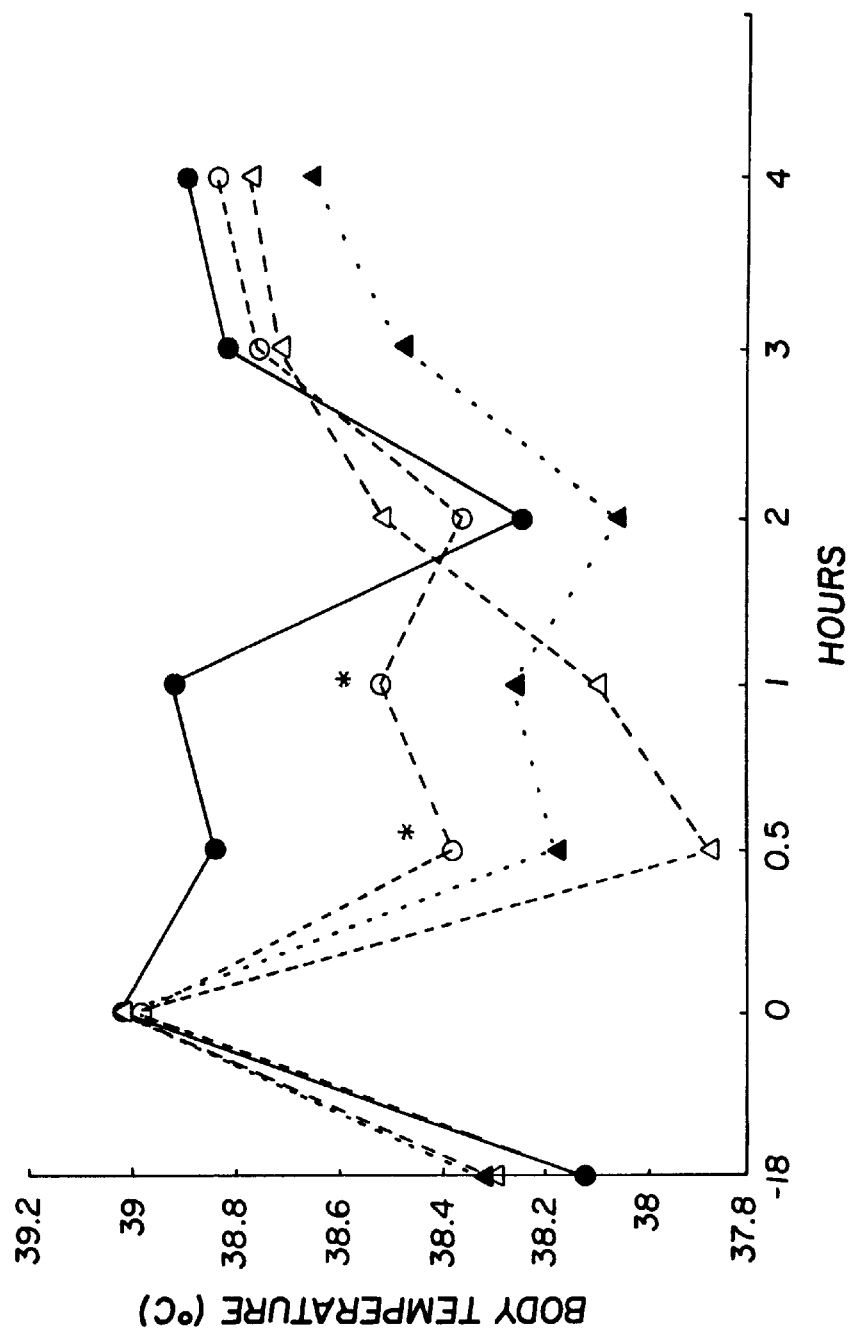

FIG. 15. At subthreshold doses the antipyretic efficacy of ASA could be clearly enhanced (0–120 min. post-administration), if the NSAID was administered as a microemulsion containing DPPC and tripalmitin (TP). In all cases the molar ratio of ASA:DPPC was maintained at 1:1, whereas the TP was administered in excess (weight ratio of DPPC:TP=1:4) (n=5/grp; *=$p>0.05$ vs ASA/DPPC; ASA/DPPC 1 mg/kg=-●-; ASA/DPPC/TP, 1 mg/kg=---○---; ASA/DPPC, 9 mg/kg=--▼--; ASA/DPPC/TP, 9 mg/kg=---Δ--).

Figure 16:
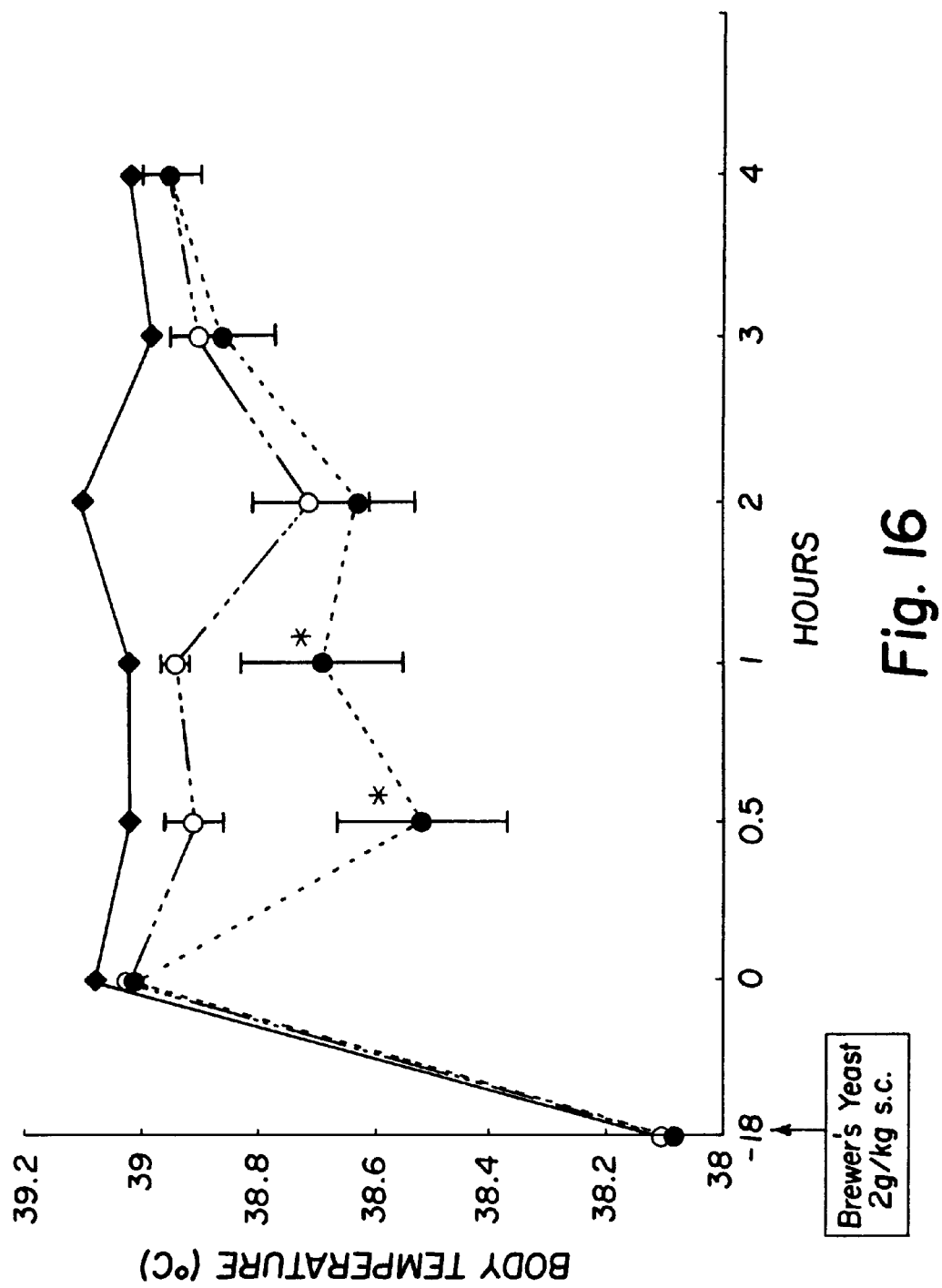

FIG. 16. It can be appreciated that the addition of the neutral lipid provided a further enhancement of antipyretic activity, even over that of ASA/DPPC, as can best be seen with the 1 mg/kg subthreshold ASA dose (n=10/grp; *=$p<0.05$ vs ASA/DPPC; ASA, 1 mg/kg=-♦-; ASA/DPPC=-○-; ASA/DPPC/TP=---●---).

Figure 17:
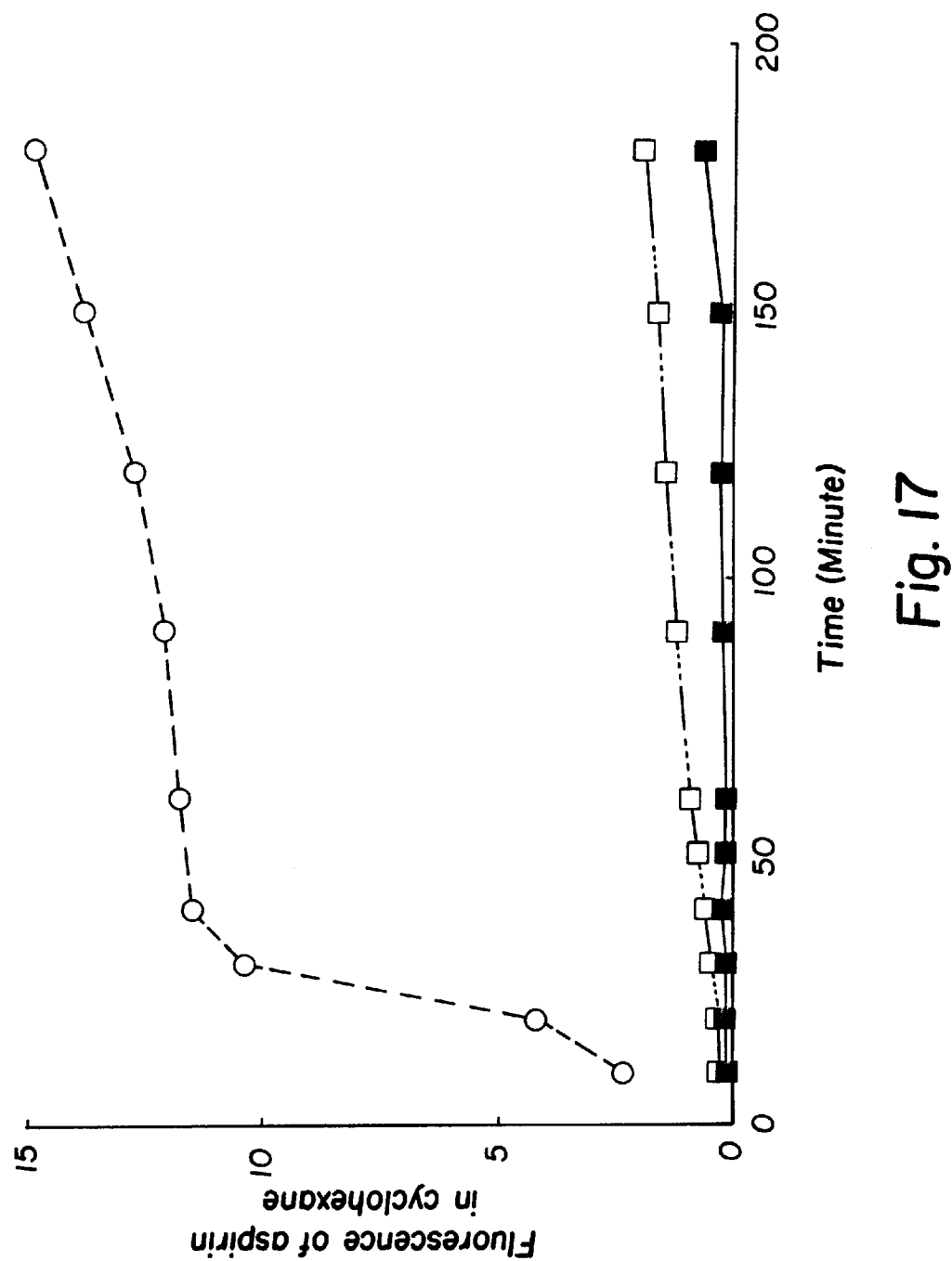

FIG. 17. The ability of DPPC to promote the movement of aspirin from water into a lipidic cyclohexane phase (as a membrane model) is greatly accelerated by the presence of the neutral lipid, tripalmitin (TP) to form a microemulsion. This may provide an explanation why the presence of neutral lipids further promote the therapeutic potency of the NSAID/DPPC complex (DPPC+TP (1:4), 2.5 mM+ASA, 10 mM (sonicated)=-○-; DPPC, 2.5 mM+ASA, 10 mM (sonicated)=-□-; TP, 2.5 mM+ASA, 10 mM=-■-).

Figure 18:
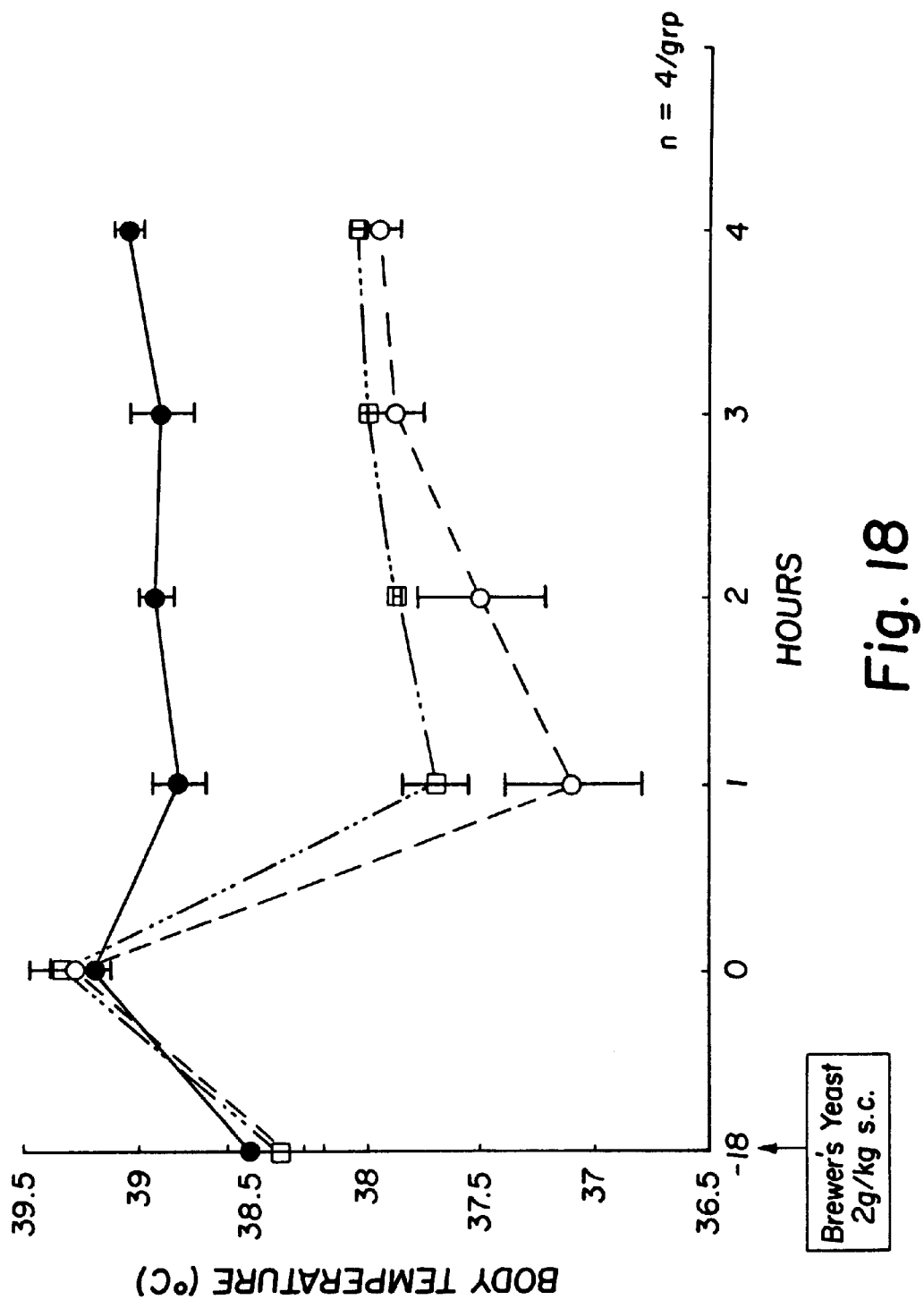

FIG. 18. The ability of DPPC to enhance the anti-pyretic activity of ASA was seen with indomethacin (Saline=-●-; indomethacin (10 mg/kg)=-□-; indomethacin (10 mg/kg)/DPPC=-○-).

Figure 19:
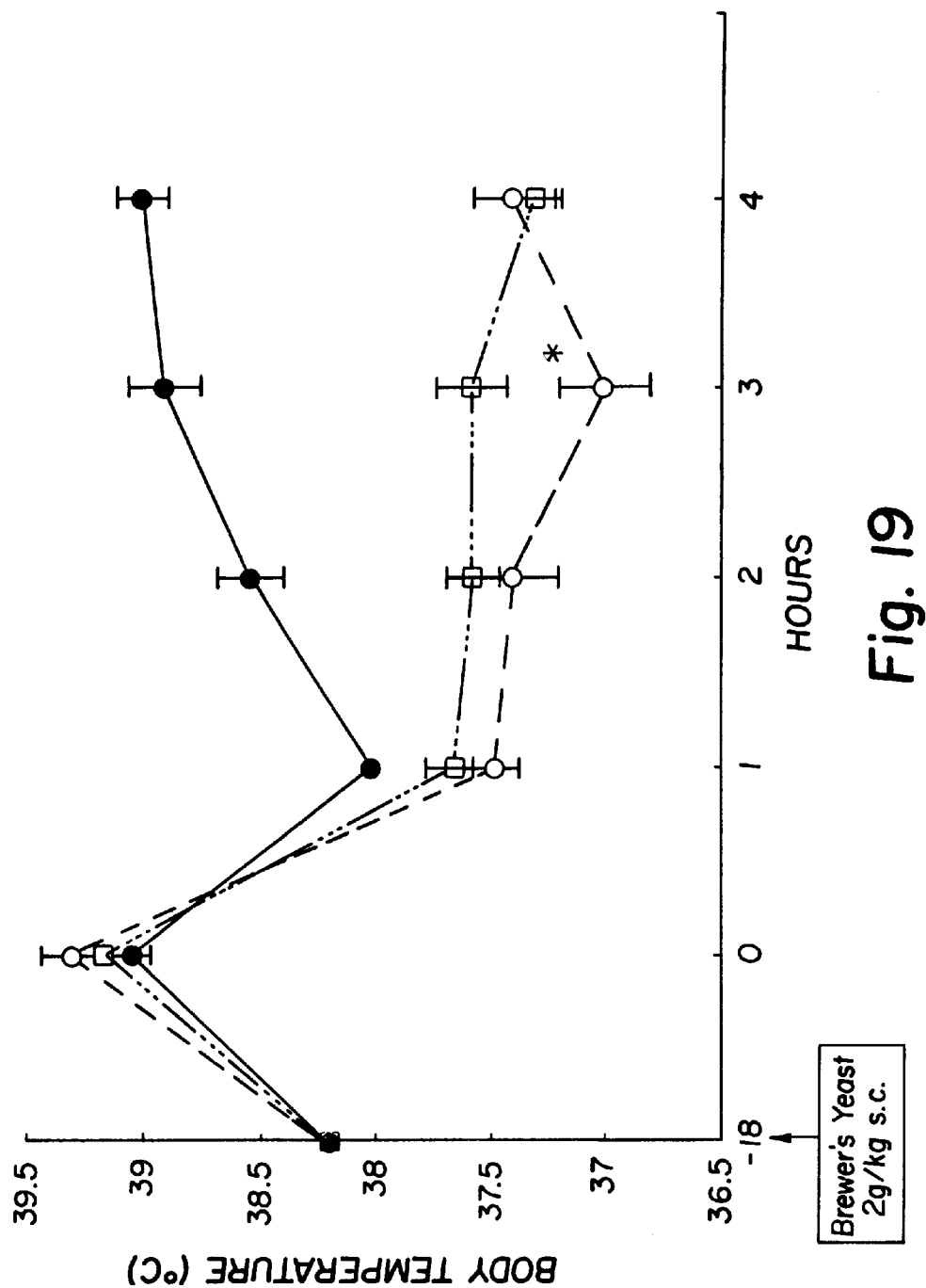

FIG. 19. Demonstrates the ability of DPPC to enhance the anti-pyretic activity of naproxen (25 mg/kg dose) (Saline=-●-; naproxen (25 mg/kg)=-□-; naproxen (25 mg/kg)/DPPC=-○-).

Figure 20:
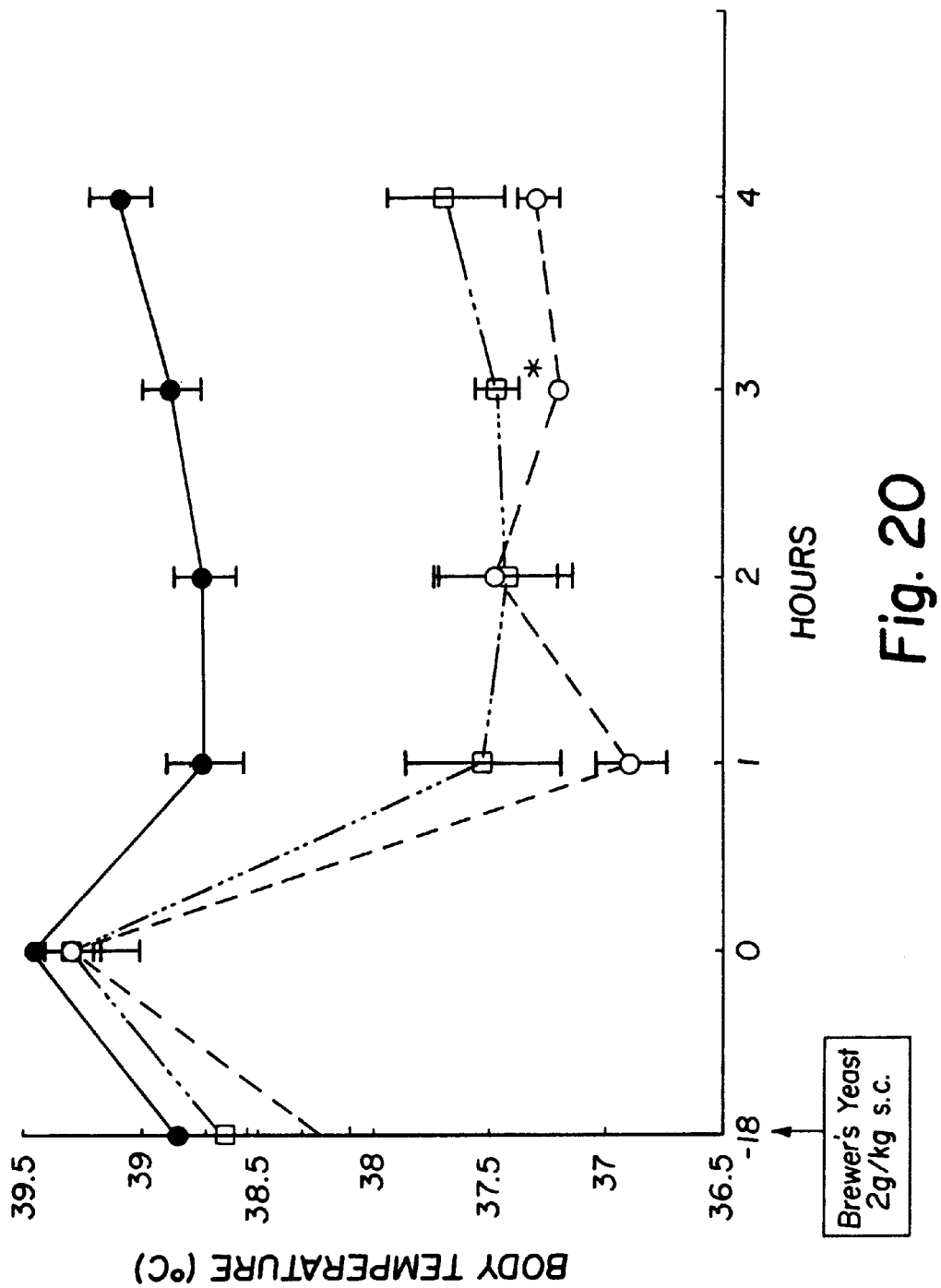

FIG. 20. Demonstrates the ability of DPPC to enhance the anti-pyretic activity of diclofenac, 10 mg/kg (Saline=-□-; diclofenac (10 mg/kg)=-□-; diclofenac (10 mg/kg)/DPPC=-○-; n=5/grp; *=$p<0.05$ vs. DICLO).

Figure 21:
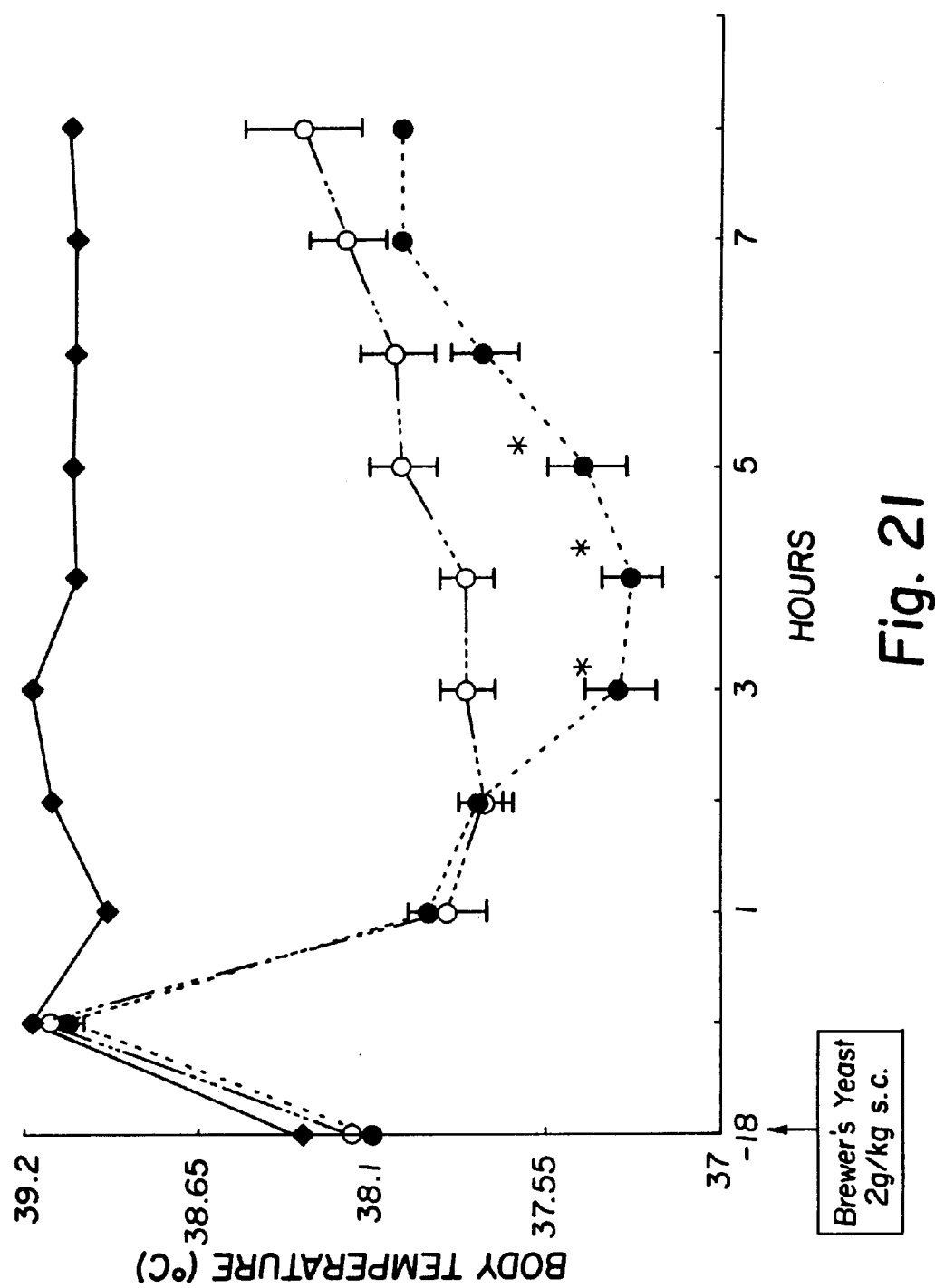

FIG. 21. Demonstrates the ability of DPPC to enhance the anti-pyretic activity of salicylic acid (SA) (70 mg/kg dose) (Saline=- -; SA (70 mg/kg)=-○-; SA (70 mg/kg)/DPPC=-●-; n=5/grp, *=$p<0.05$ vs. SA/DPPC).

Figure 22:
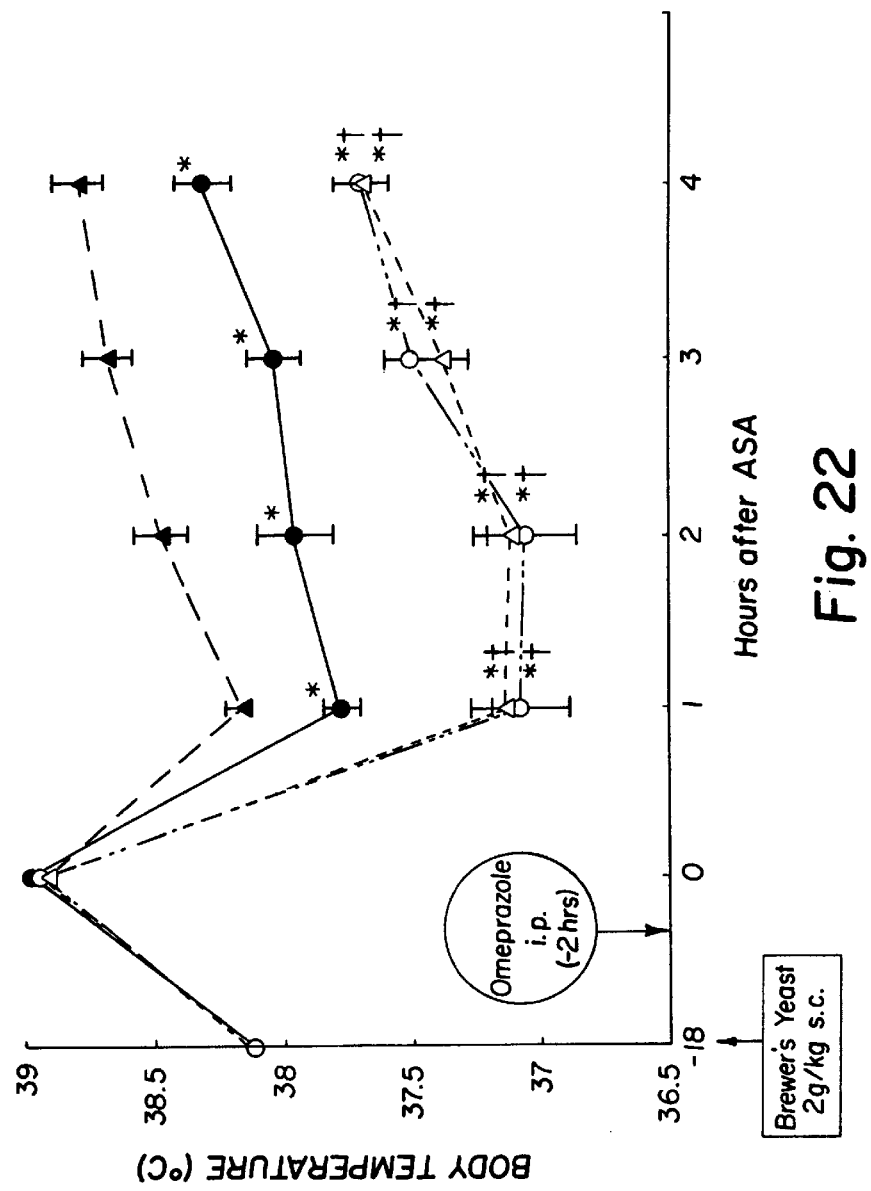

FIG. 22. Antipyretic activity of ASA (18 mg/kg) and ASA/DPPC complex with IP injection of omeprazole (150 mg/kg) two hours prior to NSAID dosage. ASA (saline)=-●-; ASA/DPPC (Sal)=-○-; ASA (omeprazole)=---▼--; ASA/DPPC (omep)=---Δ--; n=5/grp; *=$p<0.05$ vs. ASA (omep); †=$p<0.05$ vs. ASA (Sal).

Figure 23:
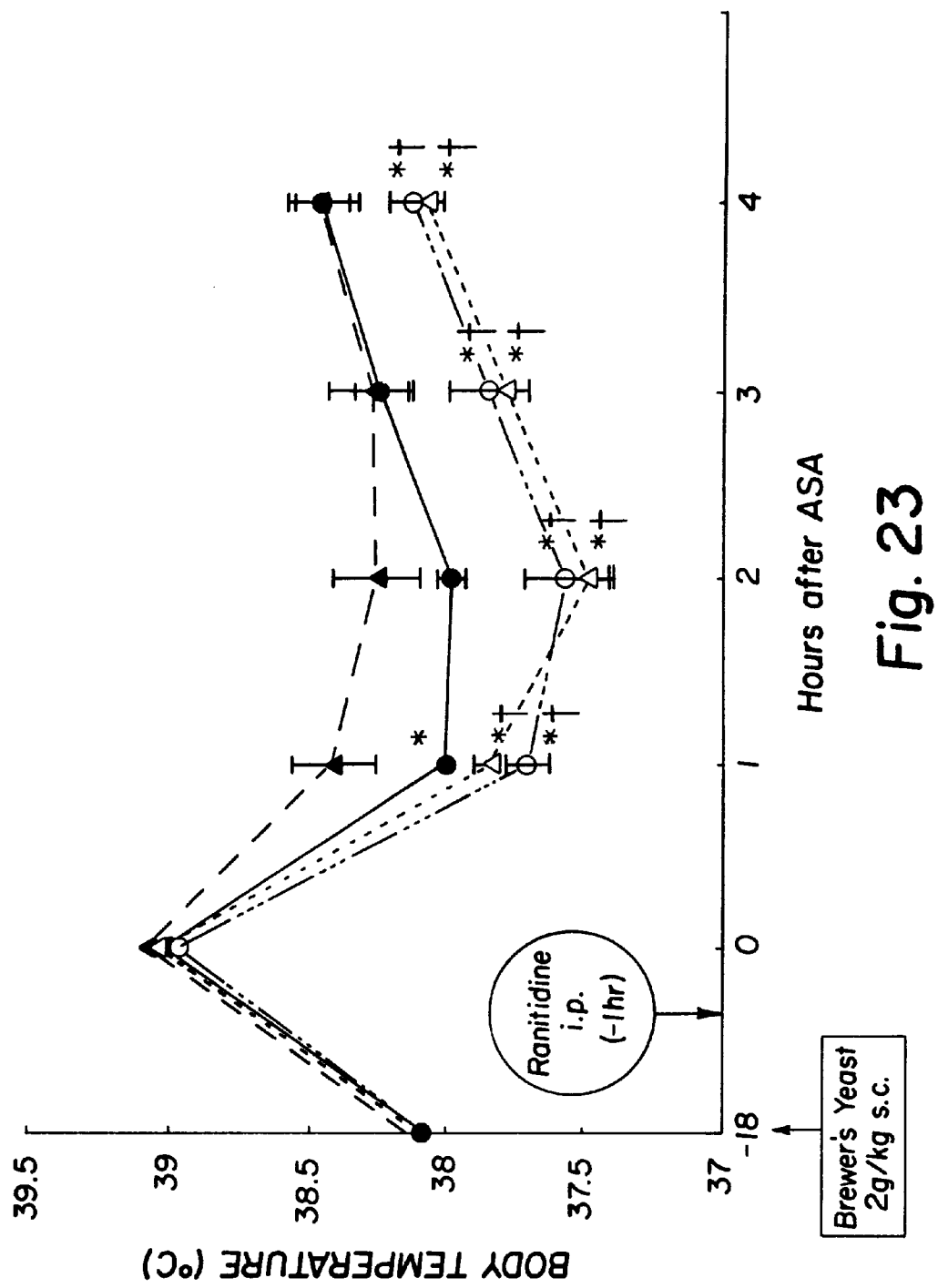

FIG. 23. Antipyretic activity of ASA (18 mg/kg) and ASA/DPPC complex with IP injection of Ranitidine (2 mg/kg) 1 hour prior to NSAID dosage. ASA (saline)=-●-; ASA (DPPC)=-○-; ASA (Ranitidine)=---▼--; ASA/DPPC (Ranitidine)=---Δ--; n=5/grp; *=$p<0.05$ vs. ASA (rani); †=$p<0.05$ vs. ASA (Sal).

Figure 24:
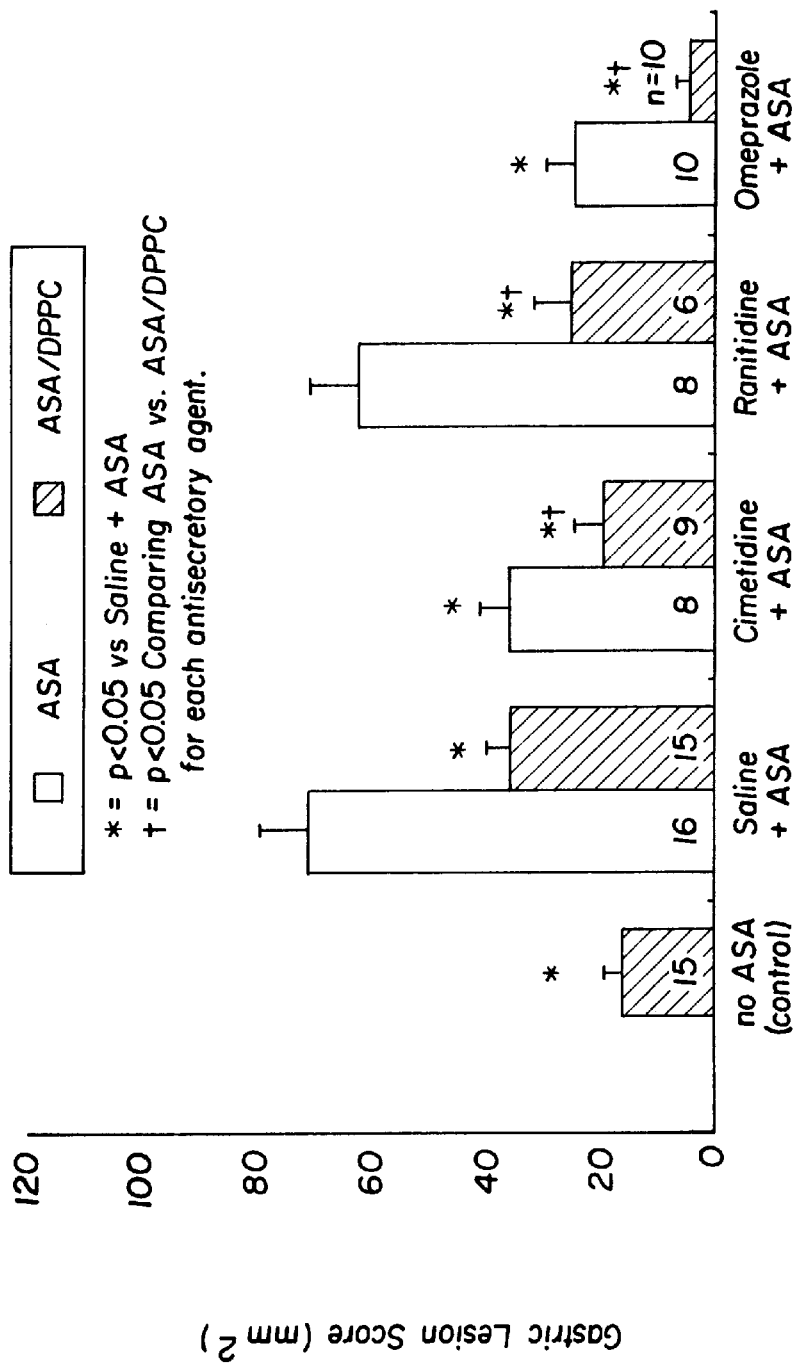

FIG. 24. Demonstrates that aspirin's ability to acutely induce gastric lesions was reduced to a variable degree in rats pretreated with an antisecretory agent (see open bars), with omeprazole and cimetidine being most protective. In contrast, antisecretory drugs consistently potected against aspirin-induced gastric lesions if the NSAID was chemically associated with DPPC (see stippled bars).

Pretreatment of rats with any one of the antisecretory agents, prior to the intragastric administration of phospholipid-complexed aspirin, afforded the animals full protection against NSAID-induced gastric lesion in this ulcer model.

Figure 25:
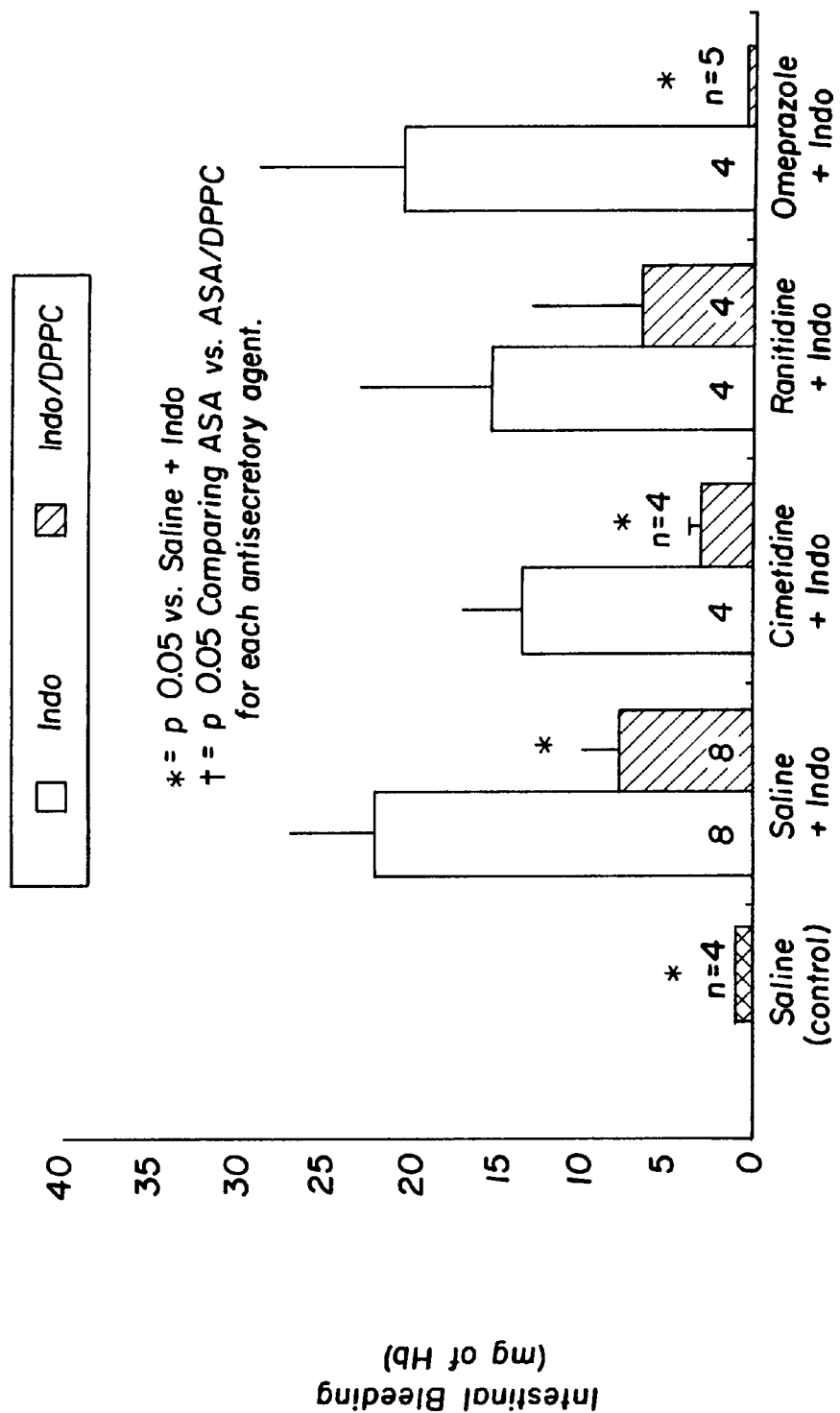

FIG. 25. Indicates that the combination therapy of antisecretory agents with indomethacin/DPPC proved superior to either the acid-inhibitor or the phospholipid alone in the prevention of acute NSAID-induced GI bleeding over an 18 hour period.

Figure 26A:
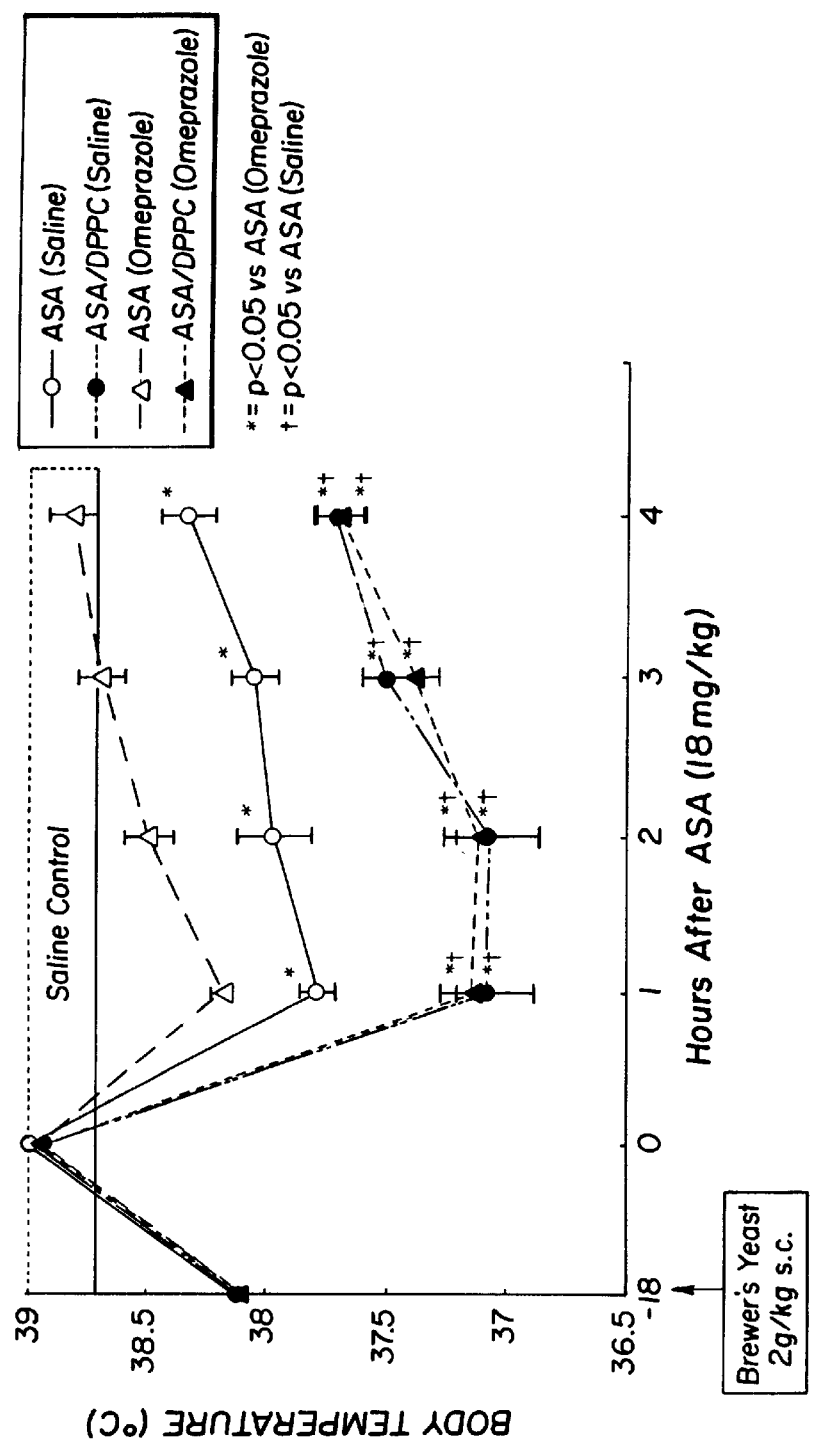
Figure 26B:
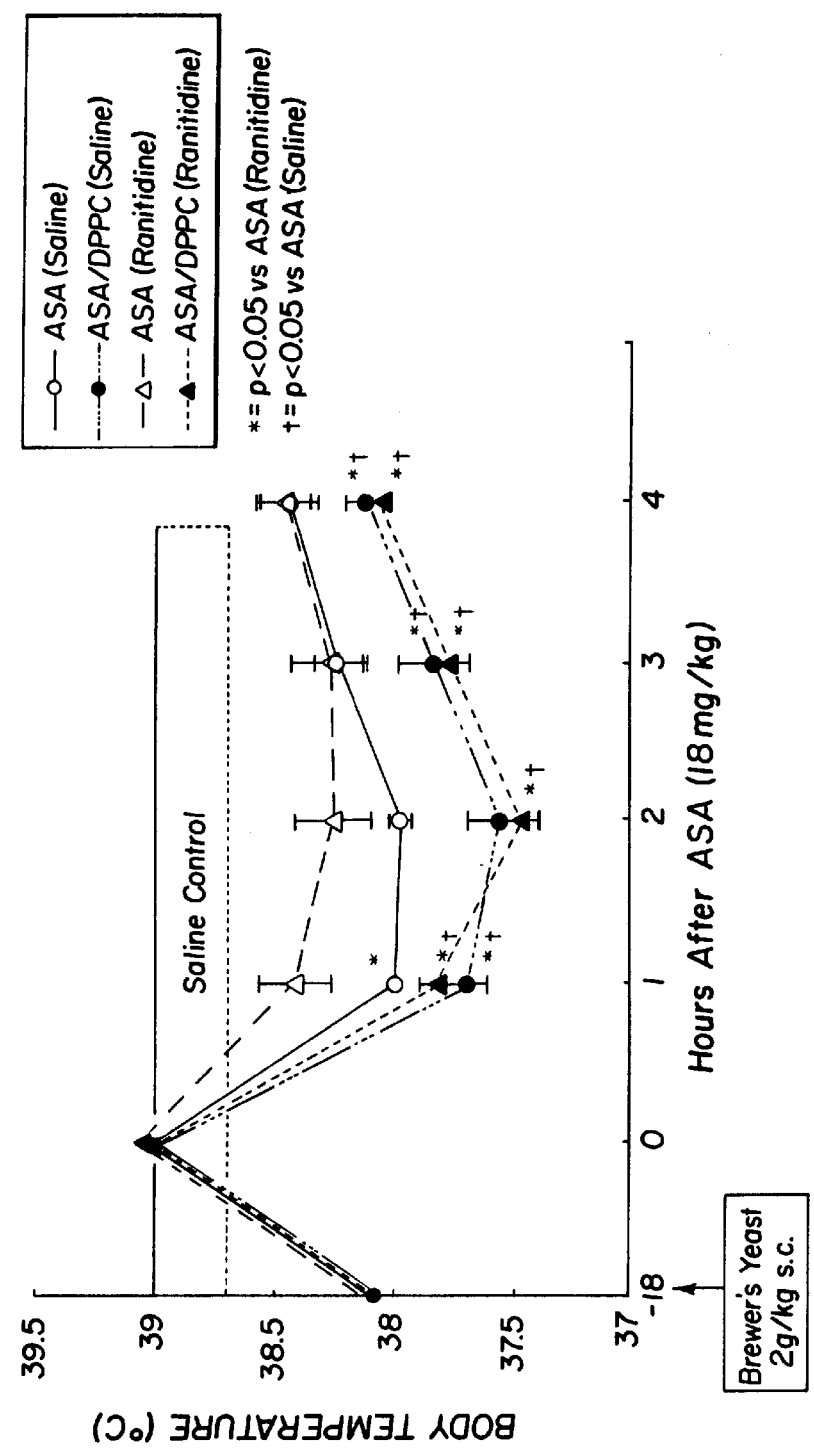
Figure 26C:
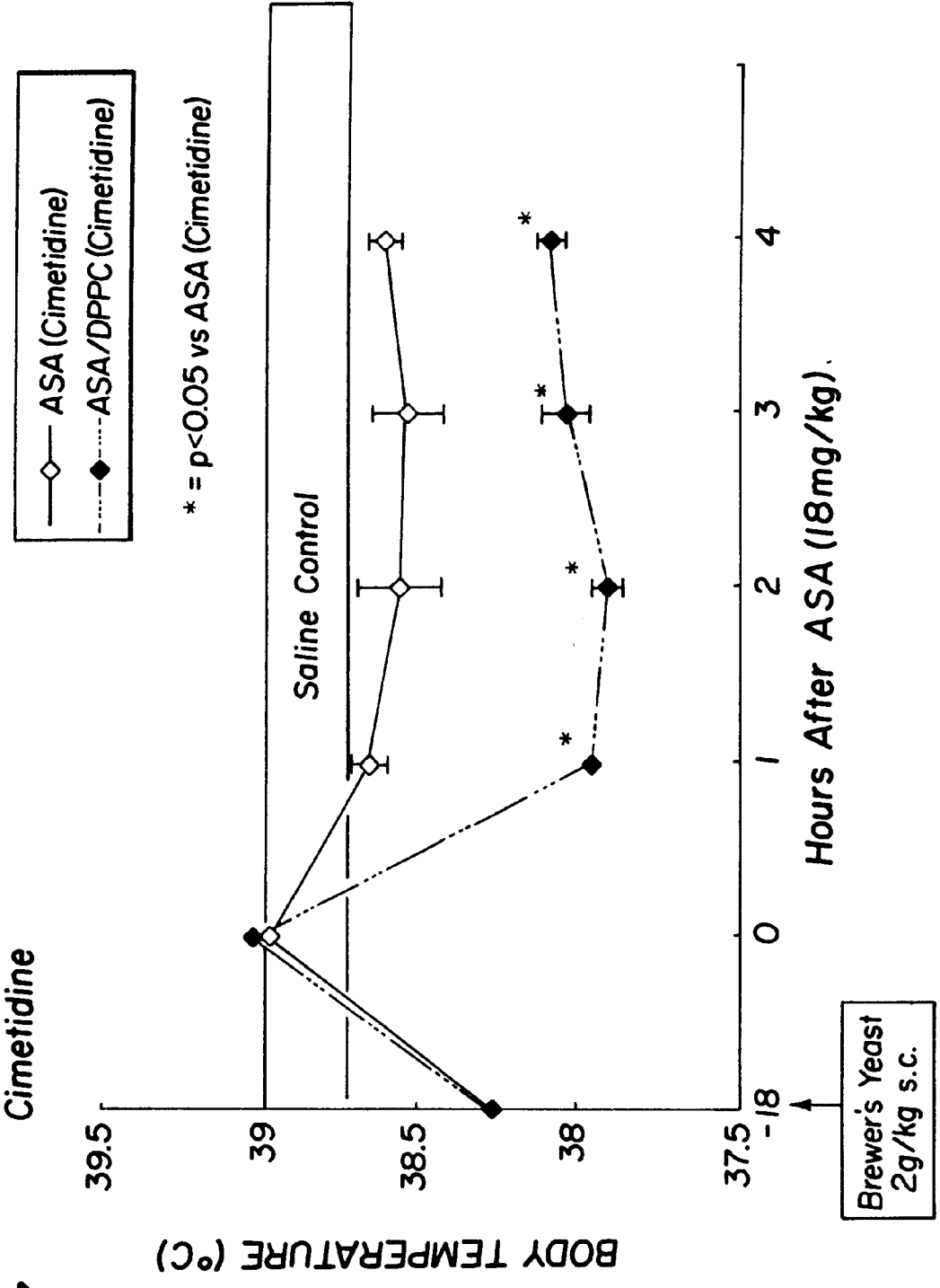

FIGS. 26A–26C. Indicates that the antipyretic activity of aspirin, administered at a dose of 18 mg/kg, was clearly attenuated if the rats were pretreated with antisecretory doses of omeprazole (FIG. 26A), ranitidine (FIG. 26B), or cimetidine© (FIG. 26C). However, the antisecretory agents' ability to attenuate aspirin's antipyretic activity was completely reversed if the NSAID was preassociated with DPPC, to increase the drug's lipophilic characteristics.

Figure 27:
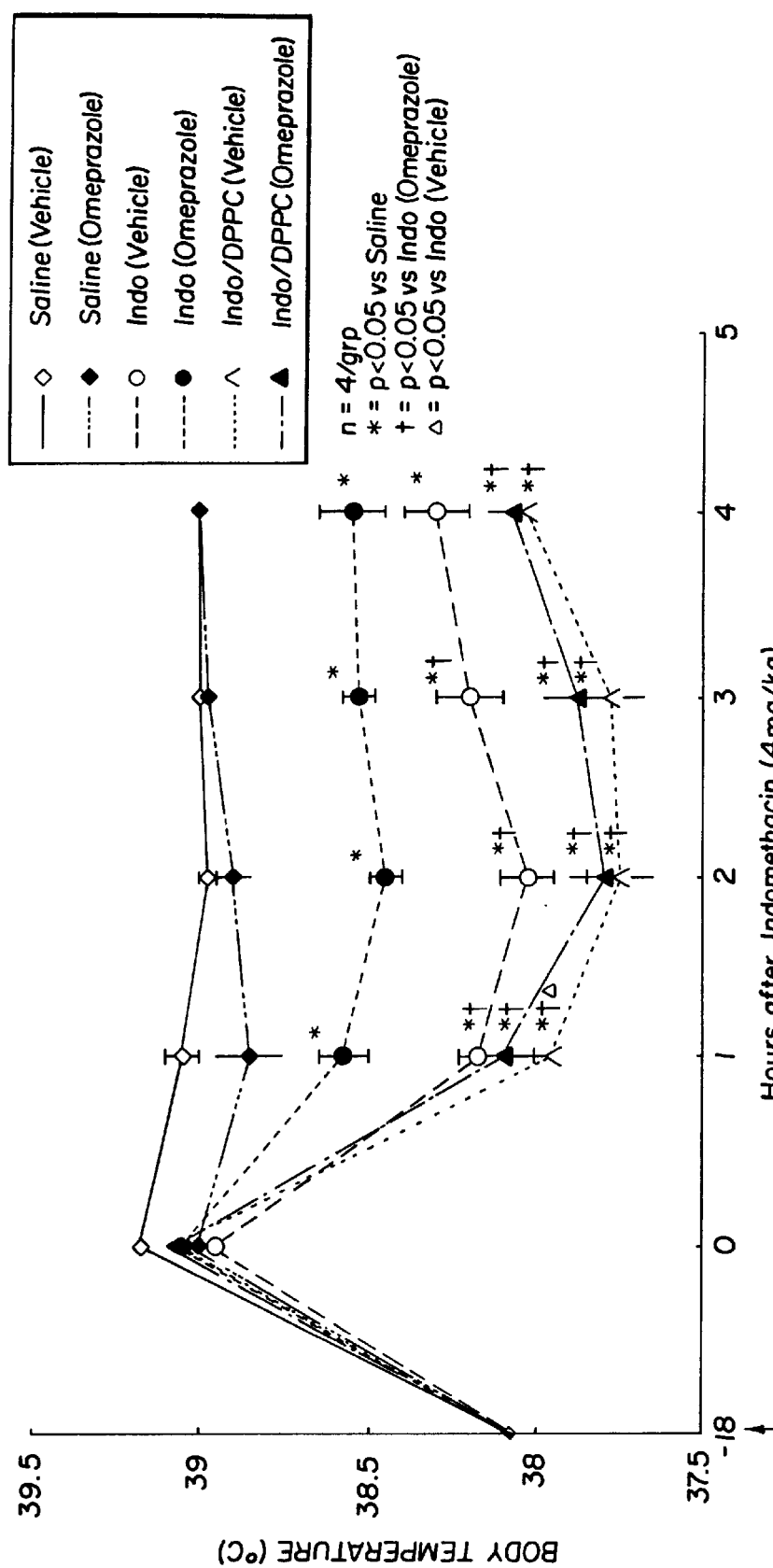

FIG. 27. Demonstrates that the proton pump inhibitor, omeprazole had an effect of reducing the antipyretic activity of indomethacin, administered at a dose of 4 mg/kg, which once again could be overcome if the NSAID was administered as a complex with DPPC.

Figure 28A:
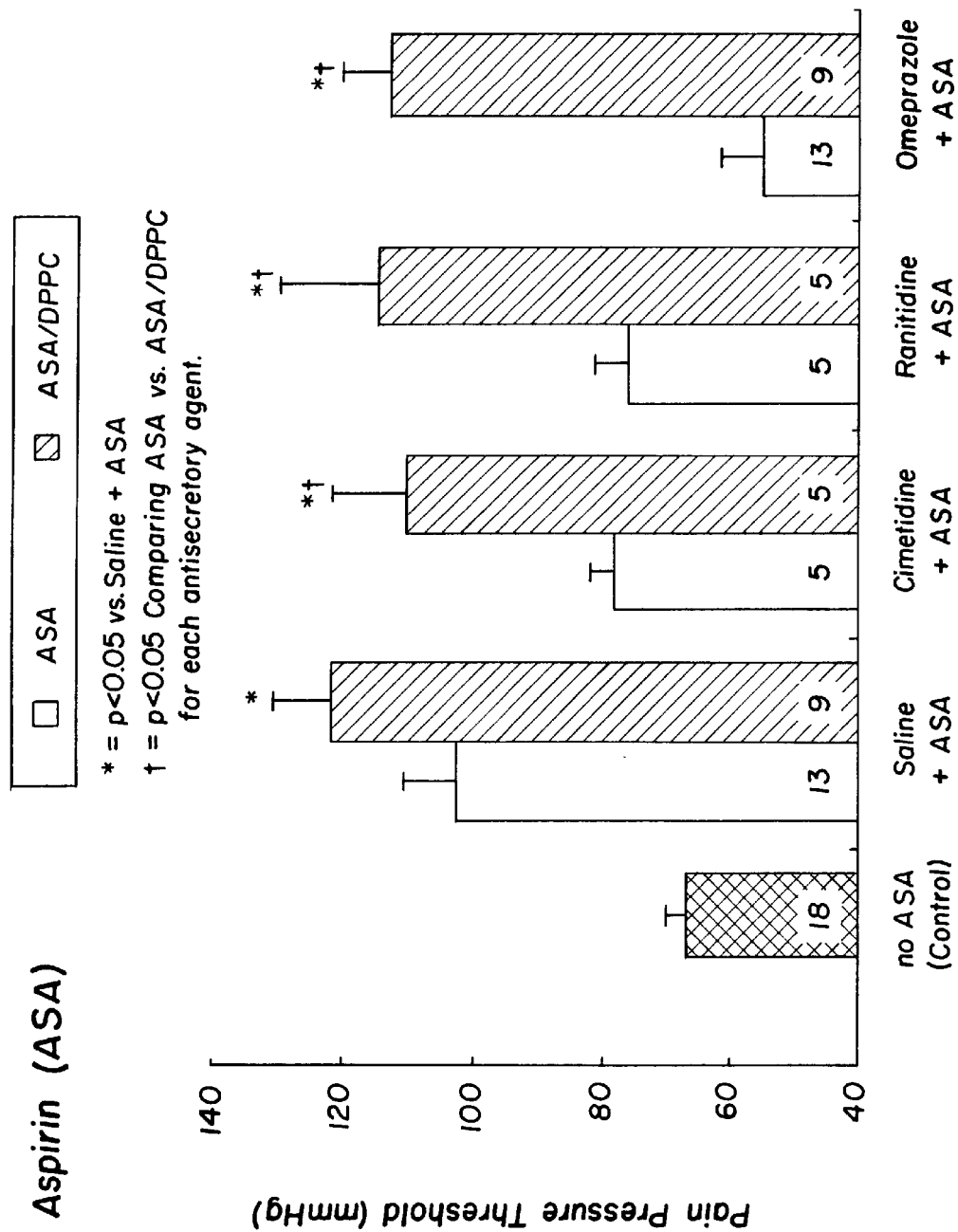
Figure 28B:
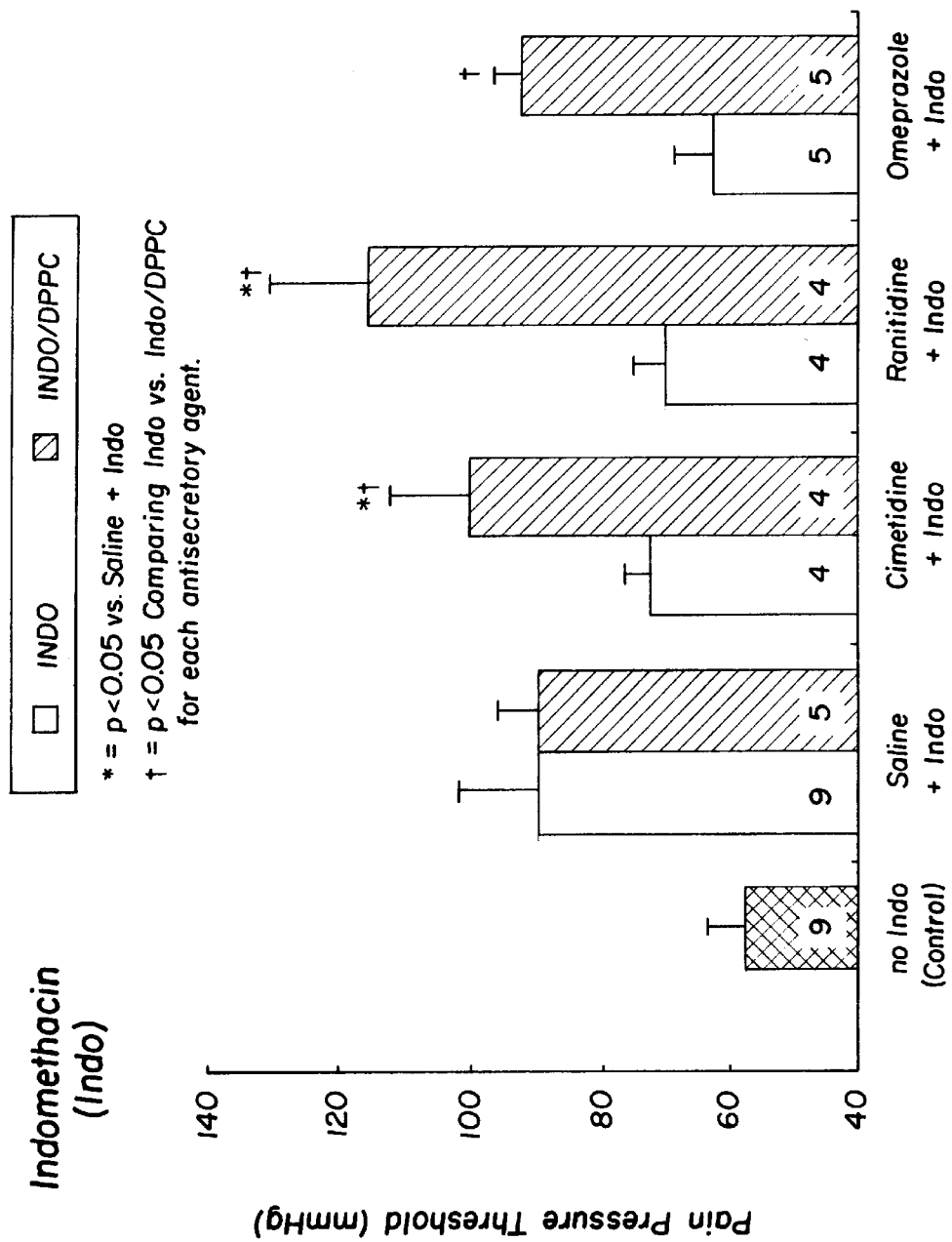

FIGS. 28A–28B. Demonstrate that the analgesic activity of both aspirin and indomethacin was similarly attenuated if rats were pretreated with an antisecretory agent. Under control conditions the "pain pressure threshold" of the inflamed paw increased approximately two-fold, from 40–60 mm Hg to 90–100 mm Hg, 2 hours after rats were administered the $ED_{50-80}$ dose of either NSAID alone. This analgesic action of both aspirin and indomethacin was clearly reduced or abolished altogether if the rats were pretreated with one of the potent antisecretory agents (compare open-bars). Furthermore, the analgesic activity of both aspirin and indomethacin could be restored in rats pretreated with an inhibitor of gastric acid secretion, if the NSAIDs were administered in the lipid-associated state (compare stippled- to open-bars for each antisecretory agent). An analgesic activity pattern very similar to that described above were observed 26 hours after rats received three consecutive treatments of aspirin or indomethacin±DPPC (at 0, 6, and 24 hours) preceded 1 hour earlier with an iruection of an antisecretory agent. Once again the NSAID-induced analgesia was significantly reduced by pretreatment with one of the three antisecretorv agents which could be overcome if the NSAIDs were chemically associated with DPPC. It is also important to note that at both time-points in the absence of one of the above antisecretory agents, both the antipyretic and analgesic activities of aspirin and indomethacin were at least as good and most cases enhanced when the drug was complexed to DPPC over that observed with the NSAID alone (compare stippled-to open-bars of rats treated with saline).

DETAILED DESCRIPTION OF THE PREFERRED EMBODIMENTS

The present invention arises from the discovery that aspirin and other NSAIDs chemically associate with zwitterionic phospholipids, such as dipalmitoyl phosphatidylcholine (DPPC). Important embodiments of the invention include methods of enhancing the various therapeutic activities of NSAID's, such as antipyretic, anti-inflammatory, and analgesic pharmacological activities. Surprisingly, these responses are observed without evidence of gastrointestinal side effects as demonstrated in acute and chronic animal models of NSAID injury in the present disclosure.

The data disclosed herein indicates that NSAIDs have the capacity to chemically associate with zwitterionic phospholipids in both organic and aqueous solvent systems, and in doing so, both classes of molecules undergo profound changes in their physical and chemical properties. Complex formation in aqueous solvent systems is shown to occur more efficiently at pH values at or slightly below the pKa of the NSAID. Therefore, without being bound by any theory, it is contemplated that the intermolecular bonding is not covalent, but is instead both hydrophobic and electrostatic, with the latter association being between the negatively charged carboxyl group of the NSAID and the positively charged nitrogen of the phospholipid. This possible interaction has been supported by computer assisted molecular modelling programs (Quanta and CHARMm), which also indicate that the NSAID/phospholipid complex has a lower molecular free energy (greater thermodynamic stability) than either reactant alone.

According to the present invention, it would be expected that orally administered NSAIDs would chemically associate with the intrinsic zwitterionic phospholipids that coat the luminal aspects of the mucus gel layer of the upper GI tract. A description of luminal aspects of the mucus gel layer is described in Goddard et al., (1990) and Kao et al. (1990). While not intending to be limited to any particular mechanism of action, this intermolecular association is thought to be the basis for the attenuation in surface activity and/or the loss of stability of the interfacial extracellular phospholipid layer, and to culminate in an NSAID induced decrease in mucosal hydrophobicity and barrier properties.

Description of the Lipid Compounds

The phospholipids of the present invention are characterized generally by the formula:

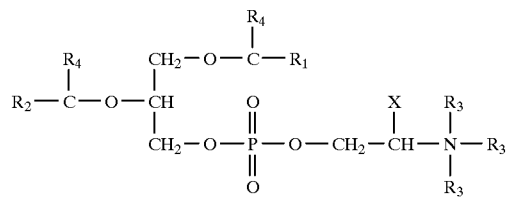

wherein $R_1$ and $R_2$ are saturated or unsaturated substitutions ranging from 8 to 32 carbon atoms; $R_3$ is H or $CH_3$, and X is H or COOH; and $R_4$ is =O or $H_2$.

As will be appreciated by those of skill in the art, the foregoing chemical structure defines a zwitterionic phospholipid structure and embraces a wide range of phospholipids, including but not limited to phosphatidyl cholines, phosphatidyl ethanolamines, phosphatidyl serines and various other zwitterionic phospholipids.

Other phospholipids that may be employed in the composition include: phosphatidylcholine, phosphatidylethanolamine, phosphatidylinositol, phosphatidylserine, sphingomyelin, and other ceramides, and mixtures thereof.

Description of the NSAID's

A few of the non-steroidal anti-inflammatory agents that may be employed in the methods and compositions disclosed herein include by way of example: pyrazolones, phenylkbutazonc (4-butyl-1,2-diphenylpyrazolidine-3,5-dion), and oxyphenbutazone (4-butyl-2-(4-hydroxyphenyl)-1-p-phenylpyrazolidine-3,5-dion), salicylic acid derivatives such as salicylic acid salicylic acid amide, acetylsalicylic acid, benorilate (4-acetamidophenyl-o-acetylsalicylate), and diflunisal (5-(2,4-difluorophenyl)-salicylic acid); Indoles, especially indometacine and its analogs such as indometacine (1-(p-chlorobenzyl)-5-methoxy-2-methylindole acetic acid), glucametacine (1-(p-chlorobenzoyl-5-methoxy-2-methylindole-3-yl acetic acid glucose amide), acemetacine (1-(p-chlorobenzoyl)-5-methoxy-3-methylindole-3-acetic acid-glycolic acid-ester), and sulindac (5-fluor-2-methyl-1-p-(methylsulphenyl)-benzylidene-indene-3-acetic acid);

Phenyl acetic acid or phenyl propionic acid derivatives such as ibuprofen (2-(4-isobutylphenyl)-propinic acid); naproxen (2-(6-methoxy-2-naphthyl)-propinic acid), alclofenac (4-allyloxy-3-chlorophenyl-acetic acid), ketoprofen (2-(3-benzylphenyl)benzoic acid), diclofenac (2-(2,6-dichlorophenylamino)-phenylacetic acid), fenoprofen (2-(3-phenyloxyphenyl)-acetic acid), tolmetin (1-methyl-5-(p-toluyl)-pyrrole-2-yl-acetic acid), flurbiprofen (2-2-fluorobiphenyl-4-ye-proprionic acid), and suprofen (p-2-thenoyl-hydratropic acid) phenyl-propionic acid); Anthranilic acids and their nitrogen analogs such as flufenamino acid (N-(m-trifluoromethylphenyl)anthranilic acid), mefenamino acid (N-(2,3-dimethylphenyl)-anthranilic acid), and niflumin acid (2-(3-trifluoromethylaminolino)-nicotinic acid).

Phospholipid compounds found to be particularly useful in the practice of the present invention are dilinoleoyl phosphatidylcholine (DLL-PC), dipalmitoyl phosphatidylcholine (DPPC) and egg phosphatidylcholine (Egg-PC or $PC_e$). In DPPC, a saturated phospholipid, the saturated aliphatic substitution $R_1$ and $R_2$ are $CH_3$—$(CH_2)_{14}$, $R_3$ is $CH_3$ and X is H. In DLL-PC, an unsaturated phospholipid, $R_1$ and $R_2$ are $CH_3$—$(CH_2)_4$—CH=CH—$CH_2$—CH=CH—$(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid).

Description of the Neutral Lipids

Neutral lipids form another component of some embodiments of the compositions described herein. This class of lipids include the triglycerides.

The triglycerides useful in the practice of the present invention are generally characterized by the formula:

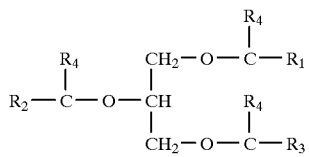

wherein $R_1$, $R_2$ and $R_3$ are each saturated or unsaturated substitutions ranging from 4 to 32 carbon atoms; and $R_4$ is either =O or $H_2$.

As will be appreciated, this structure embraces a wide range of triglycerides, both saturated and unsaturated, and include, for example, triglycerides such as tripalmitin (saturated), triolein and trilinolein (both unsaturated). A further listing of saturated and unsaturated fatty acids that can be esterified or ether-linked to the triglyceride in question is provided in U.S. Pat. No. 5,032,585, which is specifically incorporated herein by reference.

In a particular anticipated pharmaceutical preparation, the preparation will be provided in a pill form suitable for human ingestion, and contain about 2 to about 300 mg per kg aspirin or salicylate, together with an equimolar amount of PC, DPPC, or a combination thereof, or any other zwitterionic phospholipid. In the described methods, the compositions include the NSAID and the zwitterionic phospholipid in molar ratios ranging from about 1:0.1 to about 1:20, and preferably from about 1:0.5 to about 1:2. In a most preferred embodiments, the ingredients are included in a molar ratio of about 1:1.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

GI Legionary and Bleeding—Effect of NSAID and Zwitterionic Phospholipid Compositions The present example demonstrates the utility of the present invention for providing compositions that reduce the GI-related side-effects commonly associated with NSAIDS.

In order to retard the ability of NSAIDs to interact with the extracellular phospholipid lining of the mucus gel layer, several NSAIDs were preassociated with zwitterionic phospholipids and the effect was determined in various rat ulcer models. The present example shows that ability of the NSAIDs to induce acute and/or chronic GI lesions and bleeding was remarkably decreased when the drugs were administered as a complex with DPPC or related phospholipids. Surprisingly, the anti-pyretic and anti-inflammatory activity of aspirin appeared to be consistently enhanced when associated with zwitterionic phospholipids. This is in contrast to previous side effects of other formulations that reportedly suffer from reduced therapeutic efficacy or onset (Alpsten et al., 1982; Mojaverian et al., 1987).

Ulcer Models

Gastric lesions were acutely induced in rats in accordance with the following techniques. For the salicylate-based NSAIDs, fasted male Sprague Dawley rats (150–200 g) were intragastrically injected with saline (control), ASA or salicylate, or the drugs preassociated with an equimolar concentration of DPPC (all solutions adjusted to a pH of 3.1). Ten minutes later, the rats were intragastrically challenged with 1 ml of 0.6 N HCl. Gastric lesions were macroscopically scored 60 minutes later in accordance with a previously outlined method (Lichtenberger et al., 1983, incorporated herein by reference).

In order to investigate the effects of non-salicylate NSAIDs to induce GI bleeding, fasted rats were subcutaneously injected with N-nitro-L-arginine Methyl Ester (L-NAME), 1 hr. before and 1 and 6 hrs. after intragastrically receiving 1 ml of the NSAIDs; indomethacin, diclofenac, and naproxen administered alone and in association with an equimolar concentration of DPPC. The Nitric Oxide synthesis inhibitor, L-NAME, is administered before and after the NSAID to increase the rat's sensitivity to the drug in accordance with the method of Chen et. al., *Gastroenterology* 104: A53, 1993). Eighteen hours after receiving the NSAID, the distal half of the intestine was excised and flushed with 10 ml of saline. The hemoglobin (Hb) concentration of the intestinal perfusate was measured as an estimate of GI bleeding in accordance with a previously described method (Lichtenberger et al., 1983).

Rats were treated with ASA over a two week period to investigate the chronic effects of NSAID exposure (in the presence and absence of phospholipids) on hematocrit, gastric mucosal hydrophobicity, and granuloma formation. In order to ensure that the rat had an empty stomach prior to receiving the daily intragastric dose of ASA, they were placed on a reverse lighting schedule (9 AM/lights off; 5 PM/lights on), and were only provided access to chow during the day (dark period). The test solutions (saline, ASA and ASA/Phospholipon 90G complex) were intragastrically administered between 8 AM–9 AM daily during the two week study period. In these chronic exposure experiments, ASA was complexed with an equimolar concentration of Phospholipon 90G (purified soya lecithin, prepared and obtained from Nattermann GmbH of Cologne, Germany) instead of DPPC. At the completion of the study period, blood was collected into a capillary tube for the determination of hematocrit and the stomach was excised for contact angle analysis.

One of a number of NSAIDs was intragastrically administered to rats alone or preassociated with an equimolar concentration of DPPC or Phospholipon 90 G (purified soya lecithin, prepared by Nattermann GmbH of Cologne Germany) in several models of acute and chronic injury of the upper GI tract. Two contrasting animal models were employed to determine the ability of DPPC to protect against acute NSAID injury to the GI tract. For salicylate-based NSAIDs, which primarily induce stomach injury, gastric lesions were scored in fasted rats who were initially treated with aspirin or salicylate alone or complexed with DPPC and challenged 10 minutes later with a supra-physiological dose of HCl. For non-salicylate NSAIDs (indomethacin, diclofenac and naproxen) which predominantly induce injury to the mid-distal regions of the small intestine, the quantity of intraluminal blood was assessed in the distal half of the small intestine of rats who were pre- and post-treated with the Nitric Oxide synthetase inhibitor, L-NAME (N-nitro-L-arginine methyl ester).

Figure 4A:
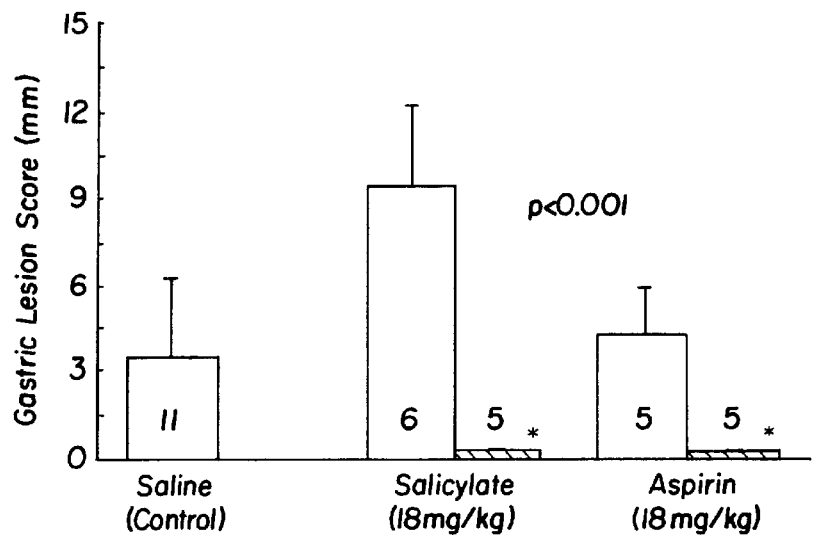
FIG. 4A. The injurious potential of salicylate and ASA to induce gastric lesions (in rats subsequently challenged with 0.6N HCl), is remarkably decreased when the NSAIDs are intragastrically administered in association with DPPC (without DPPC=clear bar; with DPPC=hatched bar).
Figure 4B:
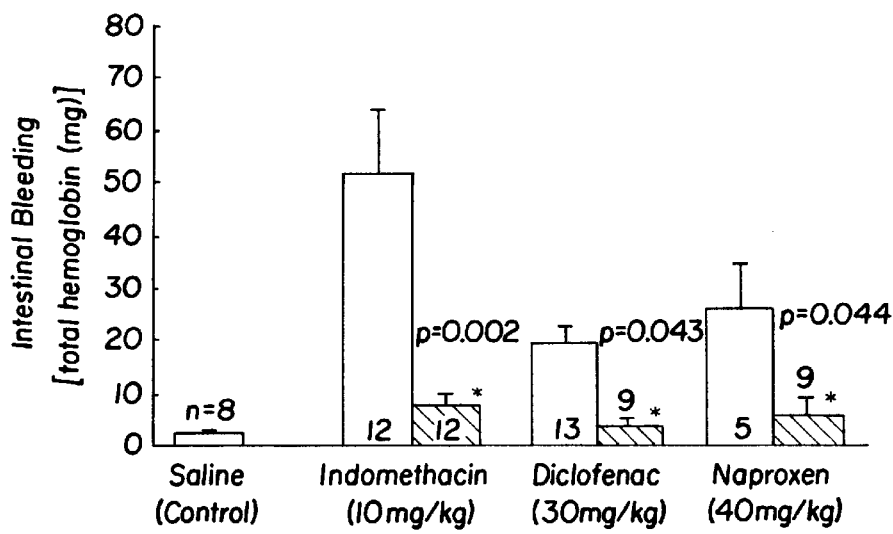
FIG. 4B. The injurious potential of non-salicylate NSAIDs to induce GI bleeding (in rats pre- and post-treated with L-NAME to increase the animal's susceptibility to the NSAID) is remarkably decreased when the drugs are intragastrically administered in association with DPPC (without DPPC=clear bar; with DPPC=hatched bar).

The results, shown in FIG. 4A and FIG. 4B, respectively, clearly demonstrate (in rats sensitized to the drugs) that the injurious potential of both salicylate-based and non-salicylate NSAIDs to induce acute GI lesions and bleeding is significantly reduced, by >85%, if the NSAID is preassociated with the zwitterionic phospholipid prior to administration. Similarly, daily administration of aspirin to rats over a 2 week period resulted in a significant fall in both hematocrit and gastric mucosal hydrophobicity, which was prevented in rats that received the aspirin/Phospholipon G complex (Table 2).

TABLE 2

Effect of DPPC on Aspirin's Chronic GI Side Effects

| Group | Gastric Mucosal Hydrophobicity (degrees, Contact Angle)[b] | Hematocrit |
| --- | --- | --- |
| Saline (Control) | 52.2 ± 2.7(6) | 51.7 ± 0.4(10) |
| Aspirin (90 mg/kg) | 15.8 ± 6.6[c](6) | 47.8 ± 0.2[c](10) |
| Aspirin + Phospholipon G | 55.3 ± 5.8[c,d](6) | 53.1 ± 0.4[c,d](10) |

[b]Gastric mucosal hydrophobicity was measured by contact angle analysis as described in Hills et al., 1983; Goddard et al., 1987; Goddard et al., 1990.
[c]$p < 0.05$ in comparison to saline-treated control values.
[d]$p < 0.05$ in comparison to values of aspirin-treated rats.
(n) number of rats/group

EXAMPLE 2

Solubility Studies; Complex formation between NSAIDS and Zwitterionic Phospholipids To demonstrate the effect of DPPC on the solubility of the sodium salts of the five NSAIDs (naproxen, indomethacin, diclofenac, salicylate and aspirin) in chloroform, each NSAID was added to chloroform at a 30 nM final concentration. DPPC was dissolved in the chloroform that was contained in half the tubes at a final concentration which ranged between 5–40 nM, prior to the addition of the NSAID salt. DPPC, as well as PC and other zwitterionic phospholipids useful in the practice of the invention, may also be dissolved in other organic solvents, such as ethanol, in the practice of the present invention. The tubes were gently mixed at 25° C. for 16 hrs, after which they were photographed and/or centrifuged (2,000 g for 15 min) and the supernatant collected to determine the concentration of NSAID in solution. The latter was assessed by measuring the NSAID's UV absorbance at 290 nm, and comparing these readings to the appropriate standard curves for each NSAID. It should be noted that for each of the five NSAIDs a linear relationship existed between the drug's concentration (nM) in water and the UV absorbance reading. The equations for the regression lines for each of the NSAIDs were as follows: aspirin, $y=2.603x-0.004$, $r=0.999$; salicylate, $y=8.780x+0.123$, $r=0.999$; indomethacin, $y=18.325x+0.156$, $r=0.999$; diclofenac, $y=21.523x+0.008$, $r=0.999$; and naproxen, $y=3.732x+0.005$, $r=0.999$. In all cases the readings for the unknowns fell within the linear portion of the standard curves. Further, the presence of DPPC in the solvent did not interfere with these analyses, as it failed to contribute to the UV absorbance reading in the absence of the NSAID.

To assess the effect of DPPC on the solubility of the sodium salt of ASA in water, ASA was dissolved in water at a final concentration of 30 nM (pH adjusted to 6.0), and its intrinsic fluorescence (290 nm/excitation; 406 nm/emission) was monitored. DPPC was present as a lipidic suspension in half the tubes at a final concentration which ranged between 15–60 nM. The tubes were gently mixed at 25° C. for the desired incubation period, after which they were centrifuged (2,000 g for 15 min) and the supernatant collected to determine the concentration of ASA in solution. Once again a linear relationship ($y=14.02+0.353$, $r=0.999$) was found between the fluorescent reading and the concentration of aspirin in solution.

Figure 2A:
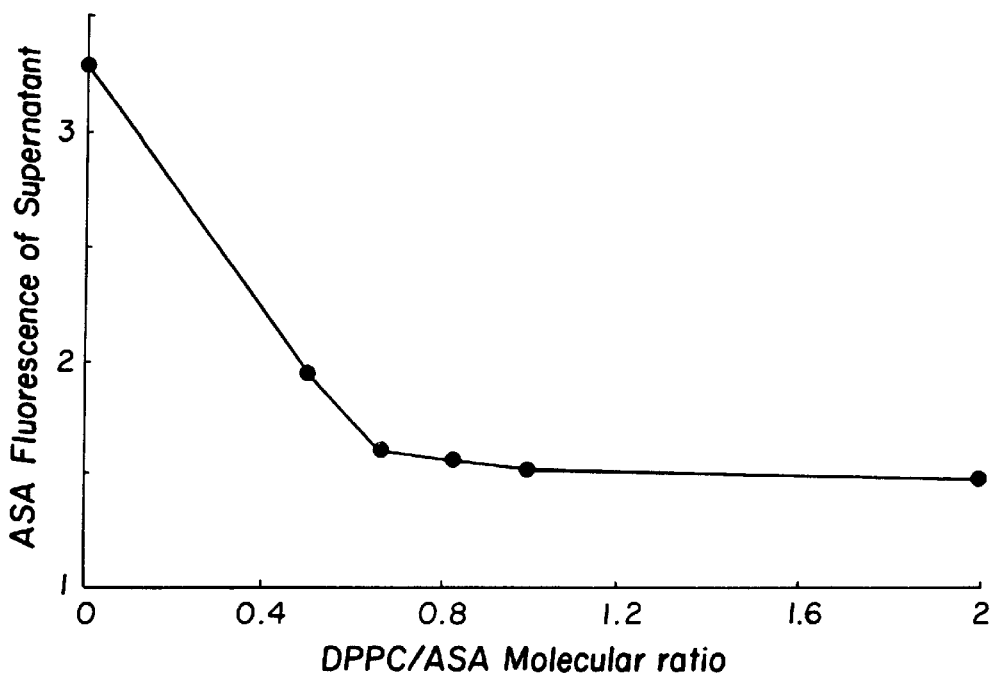
FIG. 2A. The DPPC-induced reduction in ASA's solubility in water was maximal when both reactants were present in equimolar concentration over a 60 min. incubation period at 25° C.
Figure 2B:
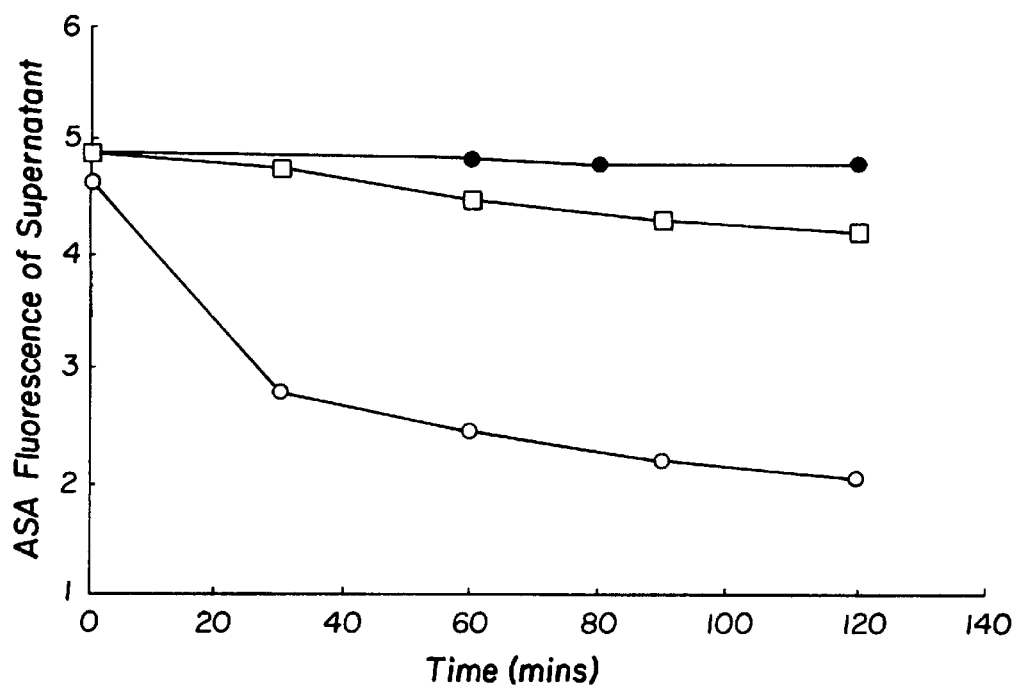
FIG. 2B. Time course at 25° C. of the reduction in ASA's solubility in water induced by the presence of equimolar concentrations of DPPC. In contrast, the concentration of ASA in water was not significantly changed over time by the addition of an equimolar concentration of the anionic phospholipid, DPPG as a lipidic suspension (ASA only=-•-; DPPG/ASA=-□-; DPPC/ASA=-○-).

It can be appreciated from FIG. 1A and FIG. 1B that the sodium salts of these NSAIDs are insoluble in chloroform unless an equimolar or greater concentration of DPPC is added to the organic solvent, at which point complete solvation takes place. Conversely the sodium salts of the NSAIDs are readily soluble in either saline or water, and are removed from solution as a complex within minutes after an equimolar concentration of DPPC is added as a lipidic suspension. The solubility of aspirin in saline can be followed either by monitoring its intrinsic fluorescence or radioactivity (employing $^{14}C$-labelled aspirin). FIG. 2A and FIG. 2B demonstrate that the injection of DPPC into an aqueous solution results in the precipitation of the NSAID, presumably as a complex with the phospholipid. The rapid change in solubility of the NSAID in both the organic and aqueous solvent systems does not occur if DPPC is substituted by the anionic phospholipid, dipalmitoylphosphatidylglycerol (DPPG).

EXAMPLE 3

Granuloma Formation and Enhanced Anti-Inflammatory Activity

The present example demonstrates the utility of the present methods for enhancing the anti-inflammatory activity of ASA accomplished when ASA, or other non-steroidal anti-inflammatory drug complexed with Phospholipon 90G.

A foreign-body granuloma model widely used by those of skill in the art to assess anti-inflammatory action was employed.

The inventors used the rat model of foreign-body granuloma formation. This model is recognized by those of skill in the art as a representative model for granuloma formation and anti-inflammatory activity, as described in Ucelay et al., (1988); and Castro et al., (1980). These references are specifically incorporated herein for the purpose of providing details associated with the use of this model.

Methods

The above model has been successfully employed in both rats and invertebrates to quantify this most basic component of a tissue's response to injury (Ucelay et al., 1988; Castro et al., 1980; Clatworthy et al., 1994, each incorporated herein by reference). Sterile tared cotton string was surgically implanted (bilaterally) under the abdominal skin of ether anesthetized rats on day 1 of the study period, and then randomly placing rats in a group to be daily treated with saline, aspirin or the NSAID complexed with Phospholipon 90G over a two-week period.

At the completion of the study period the string with the adherent granuloma tissue was surgically dissected from the euthanized rats and dried in a vacuum for several days at room temperature, until a baseline dry weight was obtained. The difference between this value and the initial dry weight of the string prior to implantation divided by the latter value provided an estimate of the weight of granuloma tissue. This technique proved to be very reproducible and accurate, as determined both by the close agreement between the changes in weight of the two pieces of string that were implanted contralaterally in each animal (<12.5% difference in values between the right and left string); and the low variance (<8%) in values of granuloma formation within a group of animals.

Improvement in the anti-inflammatory efficacy of ASA was observed over a 2 week study period. This effect is seen when the NSAID was administered as a complex with Phospholipon G at concentrations below the maximally effective dose for this particular drug (see Table 3, FIG. 5).

TABLE 3

Effect of Aspirin ± DPPC Formulations on Foreign-Body Granuloma Formation.

| Group | ±DPPC | n | Granuloma Formation[a] |
|---|---|---|---|
| Saline (Control) | − | 5 | 3.20 ± 0.10 |
| ASA (90 mg/kg) | − | 5 | 1.90 ± 0.10[b] |
|  | + | 5 | 1.4 ± 0.10[b,c] |
| ASA (140 mg/kg) | − | 6 | 1.07 ± 0.09[b] |
|  | + | 6 | 1.00 ± 0.15[b] |

[a]The values represent the dry weight of the string with adherent granuloma tissue - dry weight of string/dry weight of the string.
[b]$p < 0.05$ in comparison to saline-treated control values.
[c]$p < 0.05$ in comparison to values of rats treated with NSAIDs alone.

EXAMPLE 4

Contact Angle Analysis

The present example is provided to describe the model which was used to examine the surface tension reducing action of the compositions of a combination of non-steroidal anti-inflammatory agent and zwitterionic phospholipid.

Contact angle analysis was performed with the use of a goniometer on excised gastric mucosal tissue, that was lightly blotted and dried, as previously outlined (Hills et al., 1983; Goddard et al., 1987; Goddard et al., 1990, each incorporated herein by reference). Briefly, this was accomplished by applying a droplet of water (~5 μl) to the tissue surface, and employing the telescopic eyepiece of the goniometer to measure the maximal angle that is dissected at the triple point, where the solid/liquid/ and air interface meet.

EXAMPLE 5

Antipyretic Activity

An established rat fever model was used in the present example to demonstrate the utility of the invention for enhancing the anti-pyretic activity of a NSAID by combining these class of agents with a phospholipid.

The rat fever model involves the injection of rats with Brewer's yeast (2 g/kg, s.c.) to induce an increase in fever of 0.5–1.5° C. These models are described in Adams et al. (1968) and Ucelay et al. (1988), which references are specifically incorporated herein for this purpose. The animals were intragastrically treated (instilled) with either saline, 90 mg/kg ASA, or 90 mg/kg ASA preassociated with an equimolar concentration of DPPC. Similar antipyretic analyses were performed with the sodium salts of the following NSAIDs: diclofenac (10 mg/kg), indomethacin (10 mg/kg) and naproxen (30 mg/kg), alone and complexed with an equimolar concentration of DPPC. All test solutions were titrated to a pH of 4.5 prior to intragastric administration. Rectal temperatures were monitored in conscious, restrained rats at all indicated times. This technique provided a very reliable and reproducible estimate of the antipyretic activity of NSAID formulations as indicated by the fact the variance within a group was low, with the standard errors <5% of the mean values, and the fact that the difference in mean temperature values for a given group varied <2% between separate experiments.

EXAMPLE 6

Pharmaceutical Compositions

The complexes described in the present example are preferably for oral administration, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds (i.e., NSAID and Zwitterionic phospholipid and/or neutral lipid) may be incorporated with excipients or carriers and used in the form of ingestible tablets, buccal tablets, troches, capsules, elixirs, suspensions, syrups, wafers, and the like. Such compositions and preparations should contain enough active NSAID compound to achieve an effective plasma level of the active drug. Aspirin, for example, would be provided in doses of from about 10 mgm, or about 20 mg, or 32.5 mg or even up to 60 mg, or 300 mgs/kg would be contained in each tablet or dose, where employed for administration to animals having a weight of about 60 kg–70 kg. The dose will vary depending on the NSAID or combinations of NSAIDs used. The amount of the NSAID in particular preparations is more generally described as an amount of NSAID or combination of NSAIDs effective to provide a pharmacologically active plasma concentration of the drug when used in combination with zwitterionic phospholipid. These amounts are determinable by one of ordinary skill in the pharmaceutical arts given the data disclosed herein, and general pharmaceutical references such as Remingtons Pharmaceutical Sciences.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose, aspartame or saccharin may be added, or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both.

A syrup of elixir may contain the active compounds sucrose as a sweetening agent methyl and propylparabens as preservatives, a dye and flavoring, such as cherry or orange flavor, again formulated for oral administration. Of course, any material used in preparing any dosage unit form should be pharmaceutically pure and substantially non-toxic in the amounts employed. In addition, the active compounds may be incorporated into sustained-release preparation and formulations.

The present compositions may also be formulated as injectable formulations, or as formulations suitable for enteral administration, according to those techniques known to those of ordinary skill in the medicinal arts.

EXAMPLE 7

Lipid-Permeability of NSAID/Phospholipid Complex

The present example illustrates the utility of the invention for providing compositions and methods for enhancing the bio-absorption and bio-availability of NSAID's. The diffusion of aspirin (alone and complexed with phospholipid) from water into cyclohexane was used as a model to estimate the membrane permeability of the drug.

Permeability Analysis

The sodium salt of ASA (also salicylate) was dissolved in 5 ml of water at a final concentration of 100 mM (pH adjusted to 6.0) and gently stirred at 25° C. An equal volume of cyclohexane was layered over the aqueous solution and the entry of the NSAID into the organic phase was monitored fluorometrically over time. In order to determine the effect of phospholipid association on the lipid permeability of the NSAID, ASA (or salicylate) at the above concentration was sonicated in the presence of 0.5 mM phospholipid (DPPC or DPPG) in water (adjusted to a pH of 7), and its rate of diffusion into the cyclohexane phase was measured fluorometrically. This was accomplished by removing 1 ml of the top phase chloroform solution by pipette, injecting it into the cuvette to obtain the fluorescence reading, and returning the sample to the incubation vessel to assure that the volume did not change. This entire process could be completed in <30 seconds.

In these studies, the concentration of NSAID:phospholipid in water was adjusted to a molar ratio of 200:1, creating a large driving force to promote NSAID flux into the hydrocarbon phase, and minimizing the turbidity encountered with high phospholipid concentrations.

Results

Figure 3:
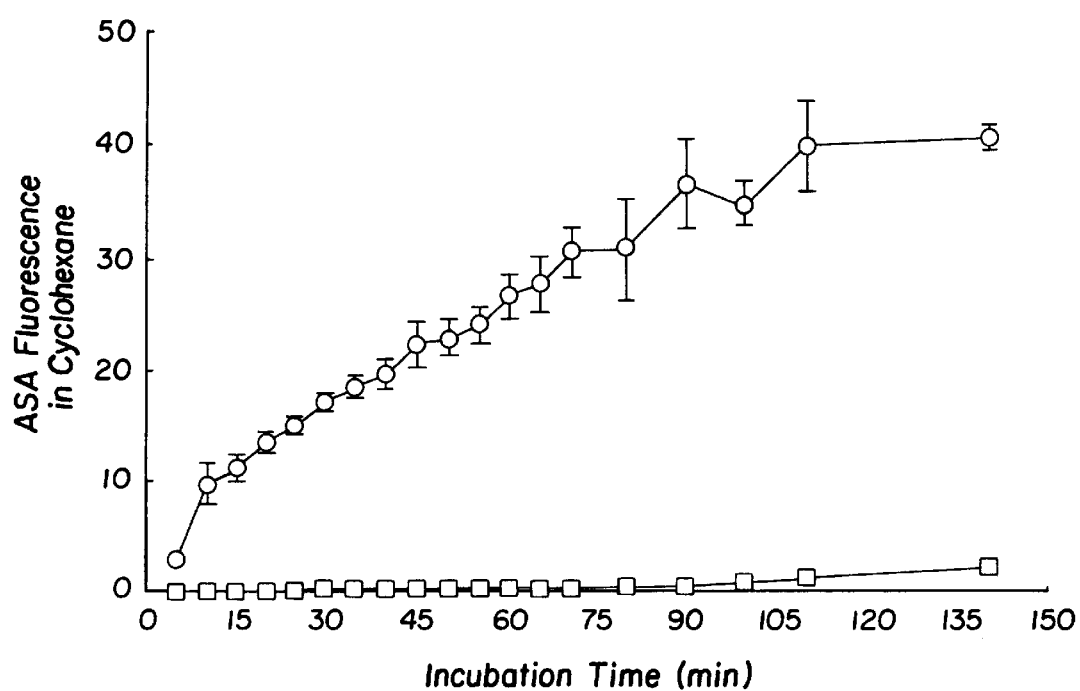
FIG. 3. The passive diffusion of ASA from water into cyclohexane is markedly accelerated by the presence of zwitterionic (DPPC) but not anionic (DPPG) phospholipids in the aqueous solution (ASA/DPPC=-○-; ASA/DPPG=-□-; DPPC=-•-; ASA=-x-).

Under neutral conditions, the passive diffusion of aspirin across an aqueous hydrocarbon interface, as assessed fluorometrically, was negligible unless it was chemically associated with the zwitterionic phospholipid, DPPC (See FIG. 3). Furthermore, this increase in the flux rate into the organic phase, was simply not a consequence of liposomal encapsulation since the NSAID failed to enter cyclohexane if the anionic phospholipid, DPPG was substituted for DPPC. These studies also revealed that DPPC promoted the flux of sodium-salicylate from the aqueous to the organic phase in a similar manner.

EXAMPLE 8

Anti-Inflammatory and Anti-Pyretic Activity of NSAID/Phospholipid Complex

This example demonstrates the utility of the present invention for enhancing the fever-reducing potential of the NSAID (20 mg/kg dose) when chemically associated with a zwitterionic phospholipid. The ability of NSAIDs (administered alone and complexed with DPPC) to reduce fever in rats was determined. Fever was induced 18 hrs prior to drug treatment by the subcutaneous administration of Brewer's yeast (Adams et al., 1968; Ucelay et al., 1988).

Figure 4C:
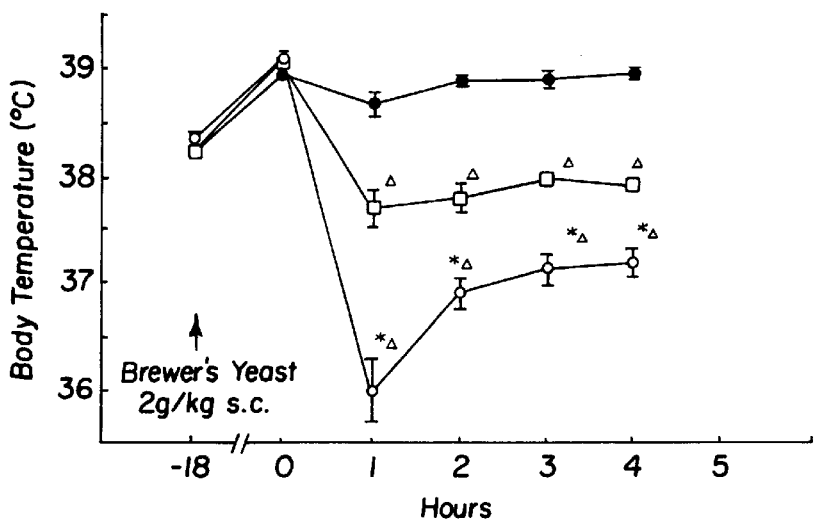
FIG. 4C. The anti-pyretic activity of the NSAID (aspirin—dose 90 mg/kg) is not diminished, and is augmented if administered as a lipidic suspension. Asterisk (*)

The results (See FIG. 4C) indicate that the anti-pyretic activity of the ASA/DPPC complex was significantly greater than that of the NSAID alone, at all time periods examined.

The enhancement in anti-pyretic activity of the NSAID/DPPC complex compared to the NSAID alone over the first three hours after intragastric administration, was observed to a lesser degree with sodium salts of the following drugs; diclofenac (−0.29° C.), indomethacin (−0.28° C.), and naproxen (−0.30° C.).

EXAMPLE 9

Enhancement of Antipyretic Activity of ASA/DPPC Complex at Subthreshold ASA Dosage The antipyretic activity of the ASA/DPPC complex was determined in rats as in Example 8 (supra), this time at much lower doses, more than 2 times lower than in Example 8. In the present example, a dosage of 9.0 mg/kg ASA was administered either alone or complexed with DPPC. The data from this study is summarized in FIG. 6.

As can be seen in FIG. 6, ASA alone does not have significant antipyretic activity at this dosage level, however ASA complexed with DPPC does have significant antipyretic activity over a five hour period. The dosage level in the present example is a 10-fold reduction of the standard dosage of 90 mg/kg, as used in Example 8, and reported in FIG. 4C.

Based on the recommended human dosages of 90 mg/kg for juvenile rheumatoid arthritis, or 325 to 650 mg for antipyretic or analgesic treatment in adults (See pages 1110–1111, Remington's Pharmaceutical Sciences, 18th Edition, Mack Publishing Company, Easton, Pa., 1990, incorporated herein by reference), it is expected that ASA complexed with DPPC, or other zwitterionic phospholipid, at a 10-fold lower dosage, i.e. approximately 9 mg/kg for juvenile rheumatoid arthritis or 32.5 to 65 mg for antipyretic activity in adults, would be as effective as the normal dosage of ASA alone to provide fever-reducing activity.

EXAMPLE 10

Analgesic Effect of Complexed-NSAIDS

It is contemplated that, in light of the demonstrated enhancement of the effects of NSAIDs (anti-inflammatory and antipyretic) when complexed with a zwitterionic phospholipid, or even further administered in combination (i.e., in a mixture) with a neutral lipid (triglyceride) that the analgesic effects of these drugs will also be enhanced when complexed with the phospholipids. Two established pain tests, using rats, may be employed to demonstrate enhancement of this effect. Tail retraction occurs in response to a noxious stimulus that generates pain. Tail retraction response may be observed and timed in rats given a placebo in order to determine a base line reaction time. If after receiving either DPPC-complexed or uncomplexed aspirin the time latency between pain induction (with a laser heat source) and tail retraction increases, this is a direct reflection of the analgesia. Retraction times will be compared between placebo and aspirin-treated rats. The test will be conducted with varying dosages and varying times after the administration of the placebo, aspirin, and/or other NSAIDs, or complex to determine if dosage or duration have some effect on the strength of the analgesia.

A model for analgesic effect in rats involves animals injected with formalin. The rats are injected under the dorsal surface of the right hind paw with a 0.05 ml volume of 15% formalin and saline solution (Helmstetter and Fanselow, 1987). The treated rats are then given the aspirin, and/or other NSAIDs, aspirin/DPPC or PC complex, or placebo at various times before and after injection with the irritating solution. The rats are then placed in a cage and their behavioral responses to the painful stimulus are be observed (employing a video camera system) and graded as follows: (1) freezing—an absence of all activity other than respiration; (2) paw lifting—the rat holds its treated paw close to its body; (3) paw licking—the rat either licks the treated paw or has some other type of mouth contact with it; and (4) general activity—this involves any other type of general movement. The behavioral response of the rat is indicative of its sensitivity. The formalin test, along with the tail flick test, comprises two distinct and separate tests to evaluate pain sensitivity and analgesia effectiveness.

EXAMPLE 11

Effects of Low Dose Aspirin (9 Mg/Kg) Alone and as a Complex with Phospholipid/Neutral Lipids on Foreign-Body Granuloma Formation in Rats[4]

The present example is provided to demonstrate the utility of the present invention for reducing inflammation. The string granulona model described herein was again used to demonstrate the activity of the presently disclosed methods for treating this condition.

Sterile tared string was surgically implanted. Five days later rats were intragastrically administered twice a day with either saline, ASA alone, or ASA lipid mixtures. Rats were sacrificed after each rat received 5 doses of the test compounds and the string and granuloma excised and weighed.

*$p<0.05$ vs. ASA alone.
ASA=Aspirin;
DPPC=Dipalmitoylphosphatidylcholine,
TP=Tripalmitin;
TO=Triolein

TABLE 4

| Saline | ASA | ASA DPPC/TP | ASA PhospholiponG/TO |
|---|---|---|---|
| 4.08(8) ±25 | 3.89(8) ±0.06 | 3.44(8) ±0.24 | 3.49(8)* ±0.17 |

Table 4. As demonstrated in the data provided in Table 4, a phospholipid (DPPC)/neutral lipid (TO) microemulsion appeared to modestly enhance the anti-inflammatory activity of ASA when the NSAID was administered at a subthreshold dose (9 mg/kg) for this activity.

EXAMPLE 12

Effect of DPPC on Aspirin's Inhibitory Effect on Platelet Aggregation

The present example demonstrates the ability of Non-Steroidal Anti-Inflammatory Drugs (NSAIDs) to inhibit cellular activation resulting in either platelet aggregation or the synthesis and release of inflammatory mediators. The activity is shown to be enhanced if the NSAIDs are administered as a complex with zwitterionic phospholipids alone or together with neutral lipids.

TABLE 5

| | % Platelet Aggregation | |
|---|---|---|
| ASA Conc | −DPPC | +DPPC |
| High Ristocetin (1.5 mg/ml) Test | | |
| 0.00 | 93% | 100% |
| 0.01 mM | 100% | 100% |
| 0.1 mM | 83% | 87% |
| 1.0 mM | 95% | 35% |
| 1.0 mM[a] | 100% | 84% |
| Low Ristocetin (0.75 mg/ml) Test | | |
| 0.00 | 75% | 94% |
| 0.01 mM | 65% | 12% |
| 0.1 mM | 26% | 20% |
| 1.0 mM | 80% | 6% |
| 1.0 mM[a] | 39% | 15% |

Abbreviations: ASA = aspirin
DPPC = dipalmitoylphosphatidylcholine
DPPC was added at a conc. equimolar to the aspirin.
In the absence of aspirin, DPPC was added at a final concentration of 1 mM.
[a]Second study.

The advantage of this invention is it will allow the NSAIDs to be administered at a lower than normal dose, due to their enhanced efficacy and potency—thus increasing their effectiveness and minimizing their side-effects on the GI tract and other organ systems.

A number of embodiments of the invention would include the combination of NSAIDs with zwitterionic phospholipids alone and together with neutral lipids. These combinations would both increase the efficacy and potency of NSAIDs to inhibit the activation of: 1) platelets; 2) neutrophils; 3) monocytes/macrophages; 4) lymphocytes; 5) Pans and 7) other bone-marrow derived cell types.

Considering the interest in the pharmaceutical industry in the role of NSAIDs in the prevention of cardiovascular disease and tissue/joint inflammation, the presently described pharmaceutical preparations would provide alternative clinical management protocols with a improved bioavailability at lower doses of the sometimes irritative NSAID regimen.

This list would include at minimum the 20–40 pharmaceutical companies presently marketing an NSAID.

EXAMPLE 13

Anti-Secretory Agents Together with NSAID and Lipids

The present example demonstrates the utility of the present invention for compositions that include an anti-secretory drug, such as Tagamet, or other histamine type 2 receptor antagonist, or Omeprazole (Prilosec™, or other proton-pump inhibitor or $H^+/K^+$ATPase inhibitors), either before or along with an NSAID complexed with phospholipid and/or neutral lipid (such as a triglyceride). These embodiments of the invention are further described in Example 14.

While not intending to be limited to any particular mechanism of action, by including a phospholipid and/or neutral lipid, the poor absorption of NSAID's that sometimes results with an anti-secretory agent administered therewith, may to some degree be prevented or lessened. Hence, the bioavailability and therapeutic action of the NSAID when administered together with an anti-secretory agent may be maintained, and in some cases enhanced.

The present example also demonstrates that the therapeutic (antipyretic) activity of aspirin, and other NSAIDs, is attenuated if animals are pre-treated with an agent that inhibits gastric acid secretion. Omeprazole (sold under the name Prilosec™) is in the class of "proton pump inhibitors", also called "$H^+/K^+$ ATPase inhibitors" that act by irreversibly binding to and inhibiting $H^+/K^+$ ATPase of the perietal cell, the rate limiting enzyme in gastric HCI secretion. Ranitidine (sole under the name Zantac™) is in the class of "$H_2$ receptor antagonists" that prevents histamine from binding to its type-2 receptor on the parietal cell to inhibit gastric acid secretion. It can be appreciated from FIGS. 22 and 23 that the blocking effect of these two classes of antisecretory drugs on the therapeutic actions of the NSAID, however, is overcome if the NSAID is complexed with a zwitterionic phospholipid. As demonstrated in FIGS. 23 and 23, aspirin at a dose of 20 mg/kg failed to reduce fever in rats if the NSAID was administered in conjunction with either the proton pump inhibitor (Prilosec™) or a histamine blocker, Ranitidine (Zantac™). This block in therapeutic activity due to inhibition of gastric acid secretin was overcome if the NSAID was administered as a complex with phospholipid, DPPC.

EXAMPLE 14

Therapeutic Regimens

The present example is provided to demonstrate various therapeutic combination regimens for treating fever, inflammation and pain. These regimens include the administration of NSAIDs together with phospholipid and/or neutral lipid.

Agents that include phospholipid, such as lecithin—tablets and the like, may be used as part of the regimens disclosed herein for the enhancement of NSAID activity.

Therapeutic Regimen

For use as an improved regimen (e.g., anti-pyretic, platelet aggregation, analgesic), the present invention contemplates an initial administration of the phospholipid, such as in a tablet or phospholipid-containing agent, such as lecithin tablets, that contain phospholipid (e.g., phosphatidyl choline).

Either at the same time or following the administration of a phospholipid or phospholipid containing agent, the patient would then be given an NSAID. The NSAID may also be administered in combination with the phospholipid as a single composition, or alternatively as a combination with both a phospholipid and a neutral lipid, such as a triglyceride (e.g., TO).

The present inventors also propose regimens that include the administration of an NSAID and phospholipid and/or neutral lipid, either before or at the same time as an anti-secretory drug, such as Tagamet® and Prilosec™. This is because antisecretory drugs are observed by the present inventor to reduce the anti-pyretic action of NSAID's. It is expected that the inclusion of phospholipid and/or neutral lipid will improve the observed reduced absorption of NSAID's observed when NSAIDs are administered with an antisecretory agent alone. Typically, this reduced absorption required that a higher dose of the NSAID be administered to the patient in order to provide the desired therapeutic effect.

Combinations of NSAIDs with zwitterionic phospholipids alone or in combination with neutral lipids will promote the ability of this family of drugs to influence certain target cells, such as neutrophils, platelets, eosinophils, macrophages, and others. In doing so, said phospholipids will increase the efficacy and potency of the NSAIDs to inhibit the cellular cyclo-oxygenase and the formation of arachidonic acid-derived products and other agents involved in cellular aggregation, adhesion, and the synthesis and release of inflammatory mediators and/or cytokines.

EXAMPLE 15

GI Side-Effects of NSAIDS are Reduced by Antisecretory Agents

Rodent model systems were employed in the present study to investigate the effects of combination therapy on the GI toxicity and therapeutic activity of aspirin and indomethacin. A comparison was then made of these results to phospholipid-associated NSAIDs.

Methods

Fasted rats were pretreated with either saline or an antisecretory dose of omeprazole, ranitidine or cimetidine and 1–2 hours later were intragastrically administered saline, aspirin or indomethacin. In ulcer models, aspirin-treated rats were post-challenged with intragastric HCl and gastric lesions measured, whereas indomethacin treated rats were pre- and post-challenged with L-NAME, and GI bleeding assessed. For antipyretic and analgesic activity rectal body temperature in febrile rats was measured, and the rat's pain sensitivity to pressure applied to an inflamed limb respectively.

Results

NSAID-induced GI ulceration and bleeding were reduced in rats pretreated with antisecretory agents and abolished in rats administered phospholipid-associated NSAIDs in combination with inhibitors of acid secretion. The antipyretic and analgesic activity of both NSAIDs were attenuated in rats pretreated with an antisecretory agent. This pH-dependent block in therapeutic activity was overcome if the NSAID is preassociated with a phospholipid to enhance the drug's lipophilic characteristics. The present example demonstrates that the combination therapy of antisecretory agents and NSAIDs, chemically associated with phospholipids, has distinct advantages with regards to both low GI toxicity and restored therapeutic activity.

EXAMPLE 16

Proton Pump Inhibitors and H2 Receptor Antagonists, Effects on Acute GI Toxicity, Antipyretic, and Analgesic Activity of Non-Steroidal Anti-Inflammatory Agents In the present study, rat model systems were also employed to investigate the effects of both proton pump inhibitors and H2 receptor antagonists on the acute GI toxicity, antipyretic and analgesic activity of aspirin and indomethacin. Parallel studies were performed with these NSAIDs coupled to phospholipids to demonstrate this as an effective strategy to increase the bioavailability of the NSAID in the presence of an anti-secretory agent, while providing enhanced protection against the drugs' injurious actions.

Materials and Methods

Animals

Male Sprague Dawley rats weighing 150–175 g were purchased from Harlan Sprague Dawley Inc (Indianapolis, Ind.) and housed in our institution's Animal Care Center 5–10 days before study, during which time they had ad libitum access to water and Harlan Teklab F-6 Rodent Diet (Madison, Wis.). All animal protocols employed exceeded NIH guidelines in the treatment and welfare of laboratory animals.

Gastric pH

Fasted rats were injected intraperitoneally with saline (control) or various doses of omeprazole (Astra Hässle AB, Molndal, Sweden), cimetidine or ranitidine (Sigma Chemical Co., St. Louis, Mo.). One hour later, the rats were ether anesthetized and after a midline incision, the stomachs were exteriorized, and 2 ml of $H_2O$ was injected into the gastric lumen and collected for pH analysis.

Ulcer Models and Chemical Association of NSAIDs with DPPC

Rats were fasted overnight and then injected i.p. with an acid-inhibitory dose of omeprazole (400, $\mu$moles/kg or 140 mg/kg) ranitidine (5 mg/kg) or cimetidine (50 mg/kg). One hour later, the rats were intragastrically administered an $ED_{50-80}$ dose of aspirin (ASA, 20 mg/kg) and challenged 10 min later with an intragastric dose of 0.6 N HCl as outlined previously. In this and all subsequent studies, the NSAIDs were administered either alone or chemically associated with an equimolar concentration of dipalmitoylphosphatidylcholine (DPPC).

The NSAID/DPPC complex was prepared, by initially dissolving the required amount of DPPC in chloroform, followed by exhaustive overnight evaporation of the organic solvent under vacuum. The NSAID salt, which was dissolved in water and subsequently titrated to the desired pH, was added to the tube containing the lipid film, followed by 15 min of sonication in a bath type sonicator (Laboratory Supplies Co. Inc., Hicksville, N.Y.). Sixty min after administration of ASA±DPPC, the rats were euthanized by $CO_2$ asphyxiation and the stomachs removed, and gastric lesions scored in accordance to a previously described method as described in Lichtenberger et al. (1995) (Natural Medicine, 1:154–158), which reference in specifically incorporated herein by referenced for this purpose.

The second animal model was based on a method described in Lichtenberger et al. (1995), in which fasted rats were administered $N^G$-nitro-L-arginine methyl ester (L-NAME, 20 mg/kg, i.p.) 1 hour before and 3 and 6 hours after the animals intragastrically received indomethacin±DPPC, at a dose of 10 mg/kg or saline (control). In this study the antisecretory agents were administered (i.p.) 90 min prior to indomethacin (or saline) treatment. Eighteen hours after the administration of the NSAID (or saline), the rats were euthanized ($CO_2$ asphyxiation) and the distal half of the intestine was flushed with 10 ml of saline which in turn was collected for hemoglobin analysis to provide an estimate of GI bleeding as outlined in Lichtenberger et al. (1995).

Antipyretic Activity

The antipyretic activity of NSAIDs was evaluated and compared in conscious rats who were made febrile by the subcutaneous injection of 2 g/kg Brewers yeast and fasted thereafter, in accordance to the method described by Adams et al., (1968) J. Pharm. Pharmac. 20:305–312 (incorporated herein by reference). Eighteen hours later, the fasted febrile rats (body temperature increased by 0.5–1.0° C.) were injected with an antisecretory agent or an equivalent volume of vehicle injected by the same route. One hour later, the rats intragastrically received 1 ml of an approximate $ED_{50-80}$ dose of either aspirin (18 mg/kg) or indomethacin (18 mg/kg) alone or the drugs preassociated with DPPC (adjusted to a pH of 7.0). Rectal body temperature was monitored over the subsequent 4 hour period.

Analgesic Activity

The ability of NSAIDs to reduce the hyperalgesia (i.e., increased sensitivity to pain) associated with an inflamed hindpaw (induced 4 days previously by the injection of 0.05 ml complete Freund's Adjuvant) was assessed. A modified version of the Randall-Selitto test was used to assess pain sensitivity of each hindpaw. (Lichtenberger et al. (1995) (Randall et al. (1957) Arch. Int. Pharmacolog. 111:409–419.) Rats were restrained in Plexiglass tubes and external pressure was applied sequentially to the uninflamed and inflamed hindpaws (0–250 g at a rate of 16 g/sec with an Analgesymeter (Life Sciences Inst., Woodland Hills, Calif.). The "pain pressure threshold" was defined as the pressure at which an animal exhibits paw withdrawal. In these studies, rats were fasted overnight and pretreated with an antisecretory agent or saline, 1 hour before receiving an $ED_{50-80}$ dose of the NSAID alone (10 mg/kg aspirin, 4 mg/kg indomethacin), or the NSAID preassociated with DPPC as described above. Two hours later, pain pressure thresholds were assessed on the both hindpaws. The dosing regimen described above was repeated at 6 and 24 hours, and the sensitivity to externally applied pressure was measured 2 hours after the animals received the last NSAID dosage.

The results were analyzed with the analysis of variance (ANOVA) procedure. If the ANOVA procedure yielded a significant interaction between variables, post ad hoc comparisons were made with Fisher's LSD test ($p<0.05$). Data are expressed as mean±standard error of the mean, with $p \leq 0.05$ being considered statistically significant.

Results

Table 6 reveals that in the conscious rats, gastric acid secretion was maximally inhibited by the injection of omeprazole at a dose of 400 $\mu$moles/kg, with gastric pH not being significant from neutrality. The $H_2$-receptor blockers, ranitidine and cimetidine, at doses of 5 and 50 mg/kg respectively, were somewhat less efficacious in inhibiting gastric acid secretion in the rat, raising the gastric pH to values >6.0 in 1–2 hours.

TABLE 6

Ability of Antisecretory Drugs to Neutralize Gastric Juice pH in Rats[a]

| Groups | Dose | Gastric Juice pH |
|---|---|---|
| Saline | 0 | 3.45 ± 0.05 |
| Omeprazole[b] | 40 μmoles/kg | 4.15 ± 0.60 |
|  | 400 μmoles/kg | 7.21 ± 0.15* |
| Ranitidine[c] | 5 mg/kg | 6.03 ± 0.27 |
|  | 20 mg/kg | 6.30 ± 0.24* |
| Cimetidine[c] | 20 mg/kg | 3.58 ± 0.46 |
|  | 50 mg/kg | 6.13 ± 0.32* |

[a]Fasted rats were injected i.p. with omeprazole, ranitidine, cimetidine or saline. 2 hours later under other anesthesia a laparotomy was performed. Clamps were then placed at the esophageal and duodenal ends and 2 ml. Of water was injected through the gastric wall into the lumen. After mixing, the gastric fluid was collected for pH analysis.
[b]Omeprazole was suspended in 1 part 10 mg % polyethylene glycol in 5 parts 19 mM $NaHCO_3$.
[c]Ranitidine and cimetidine were solubilized in distilled $H_2O$.
*= $p < 0.05$ vs. The gastric juice pH of control rats injected with saline.

Proton pump inhibitors and H2-receptor antagonists are presently being recommended for both the prevention and treatment of gastroduodenal ulcers associated with NSAID usage based upon encouraging clinical findings.[4–8] Pretreatment of rats with antisecretory doses of omeprazole, ranitidine and cimetidine were moderately effective in reducing GI injury and bleeding induced by acute exposure to aspirin or indomethacin. The GI toxicity of the above potent antisecretory agents were used in combination with phospholipid-associated NSAIDs. The results presented above clearly indicate that this strategy proved the most effective in eliminating the acute GI side-effects of both aspirin and indomethacin.

The results presented here based upon rodent model systems, indicate that the powerful anti-secretory agents—omeprazole, ranitidine and cimetidine appear to attenuate the therapeutic activity of anionic NSAIDs to reduce fever, pain and/or inflammation. This apparent reduction in bioavailability was best observed when the antisecretory agents were administered at a dose to increase gastric juice pH>6.0 and the NSAIDs were administered at an $ED_{50-80}$ dose to induce anti-pyretic, anti-inflammatory/analgesic activity. These findings thereby establish that although combination therapy of antisecretory agents with NSAIDs appears to effectively reduce the GI toxicity of NSAIDs, due to neutralization of gastric acidity, it may be contra-indicated in clinical situations where relief from pain, inflammation and fever is needed.

The mechanism by which omeprazole, ranitidine and cimetidine blocks the therapeutic activity of both aspirin and indomethacin most likely relates to their common ability to neutralize gastric acidity and block the acid-dependent conversion of the NSAIDs into their membrane-permeable lipidic state. Orally administered NSAIDs are absorbed across the upper GI tract primarily in their undissociated lipidic state (McCormack, K & Brune, K).[28] The present inventors' view of the data presented here thus propose that pharmacological neutralization of the gastric juice to pH>pKa of the NSAID would limit the absorption of the drugs across the gastroduodenal mucosa. This block in the gastric absorption of the drugs would result in the movement of the NSAIDs into, and possibly their absorption from, lower regions of the small intestine where they could be exposed to metabolism by both pancreatic and/or brush border enzymes.

The data presented in this invention demonstrated that the antipyretic, and anti-inflammatory activity of the complex was superior to that of the NSAID alone. This apparent enhancement in therapeutic activity may be attributable to an increase in the lipid permeability/solubility of the phospholipid-associated NSAID. It was predicted that ionic binding between the DPPC and the NSAID may shield the NSAID from undergoing pH dependent changes in charge, and that unlike the free-NSAID, the complex would remain lipophilic even as the intragastric pH approached neutrality. Evidence reported here appears to support this assertion, as the block in the NSAIDs' antipyretic and anti-inflammatory/analgesic activities observed with the three potent antisecretory test agents could be overcome if the NSAIDs were administered to rats as a preformed complex with DPPC. It was also of interest to note that even in the absence of the antisecretory agents, both NSAIDs when administered as a lipidic complex appeared to have equivalent or greater therapeutic efficacy to that of the NSAID alone in reducing fever and pain, confirming the present findings on the ability of DPPC to enhance the therapeutic activity of NSAIDs.

TABLE 7

Inhibitors of Gastric Acid Secretion
H2-Receptor Antagonists

| Chemical Name | Brand Name |
|---|---|
| Cimetidine | Tagamet ® |
| Ranitidine | Zantac ® |
| Famotidine | Pepsid ® |
| Nizatidin | Axid ® |
| Proton-Pump Inhibitors |  |
| Omeprazole | Prilosec ® |
| Lansoprazole | Prevacid ® |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically, pharmacologically, and/or physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Adams, S. S., Hebborn, P. & Nicholson, J. S. Some aspects of the pharmacology of ibufenac, a non-steroidal ant-inflammatory agent. *J. Pharm. Pharmac.* 20, 305–312 (1968).
2. Agrawal, N. M. Epidemiology and prevention of non-steroidal anti-inflammatory drug effects in the gastrointestinal tract. *Br. J. Rheumatology* 34 (suppl 1): 5–10 (1995).

3. Alexander, A. M., Veitch, G. B. A. & Wood, J. B. Anti-rheumatic and analgesic drug usage and acute gastro-intestinal bleeding in elderly patients. *J. Clin. Hosp. Pharm.* 10, 89–93 (1985).
4. Allison, M. C., Howatson, A. G., Torrance, C. J., Lee, F. D. & Russell, R. I. Gastrointestinal damage associated with the use of nonsteroidal anti-inflammatory drugs *N. Engl. J. Med.* 327, 749–754 (1992).
5. Alpsten, M., Bogentoft, C., Ekenved, G., & Solvell, L. Gastric emptying and absorption of acetylsalicylic acid administered as enteric-coated microgranules. *Eur. J. Clin. Pharm.* 22, 57–61, 1982.
6. Castro, G. A., Malone, C. & Smith, S. Systemic anti-inflammatory effect associated with enteric trichinellosis in the rat. *J. Parasitol.* 66, 407–412 (1980).
7. Daneshmend, T. K., Stein, A. G., Bhaskar, N. K., Hawkey, C. J. Abolition by omeprazole of aspirin-induced gastric mucosal injury in man. *Gut* 31, 514–519 (1990).
8. Ekstrom, P., Carling, L., Wetterhus, S., Wingren, P. K. Omeprazole reduces the frequency of gastroduodenal lesion and dyspeptic symptoms during NSAID therapy. *Gastroenterology* 108, A87 (1995).
9. Fuster, V., Dyken, M. L., Vokonas, P. S., and Hennekens, C. Aspirin as a therapeutic agent in cardiovascular disease. *Circulation* 87, 659–675 (1993).
10. Ghyczy et al., U.S. Pat. No. 4,309,420.
11. Ghyczy et al., U.S. Pat. No. 4,369,182.
12. Ghyczy et al., U.S. Pat. No. 4,421,747.
13. Goddard, P. J., Kao, Y-C. & Lichtenberger, L. M. Luminal surface hydrophobicity of canine gastric mucosa is dependent on a surface mucous gel. *Gastroenterology* 98, 361–370 (1990).
14. Goddard, P. J., Hills, B. A. & Lichtenberger, L. M. Does aspirin damage the canine gastric mucosa by reducing its surface hydrophobicity? *Am. J. Physiol.* 252, G-421–430 (1987).
15. Graham, D. Y. Prevention of gastroduodenal injury induced by chronic nonsteroidal anti-inflammatory drug therapy. *Gastroenterology* 96, 675–681 (1989).
16. Helmstetter, F. J., Fanselow, M. S. Strain differences in reversal of conditional analgesia by opiod antagonists. *Behavioral Neurosciences,* 101, 735–737 (1987).
17. Hills, B. A., Butler, B. D. & Lichtenberger, L. M. Gastric Mucosal Barrier: The hydrophobic lining to the lumen of the stomach. *Am. J. Physiol.* 244, G-561–568 (1983).
18. Hudson, N., Taha, A. S., Russell, R. I., Sturrock, R. G., Tyre, P., Cottrell, J., Mann, J. G., Swannell, A., Hawkey, C. J. High dose famotidine as healing and maintenance treatment for NSAIDassociated gastroduodenal ulceration. *Gastroenterology* 108, A117 (1995).
19. Jolobe, O. M. P. & Montgomery, R. D. Changing clinical pattern of gastric ulcer: are anti-inflammatory drugs involved? *Digestion* 29, 164–170 (1984).
20. Kao, Y-C., & Lichtenberger, L. M. Phospholipid- and neutral-lipid containing organelled of rat gastroduodenal mucous cells. *Gastroenterology* 101, 7–21 (1991).
21. Kao, Y-C., Goddard, P. J. & Lichtenberger, L. M. Morphological effects of aspirin and prostaglandin on the canine gastric mucosal surface: analysis with a phospholipid cytochemical stain. *Gastroenterology* 98, 592–606 (1990).
22. Kao, Y-C., & Lichtenberger, L. M. Effect of 16, 16 dimethyl prostaglandin $E_2$ on the lipidic organelles of rat gastric surface mucous cells. *Gastroenterology* 104, 103–113 (1993).
23. Kurata J. H., Abbey, D. E. The effect of chronic aspirin use on duodenal and gastric ulcer hospitalizations. *J. Clin. Gastroenterol.* 12, 260–266 (1990).
24. Lichtenberger, L. M., Graziani, L. A., Dial, E. J., Butler, B. D. & Hills, B. A. Role of surface-active phospholipids in gastric cytoprotection. *Science* 219, 1327–1329 (1983)
25. Lichtenberger, L. M., Ulloa, C., Vanous, A. L., Romero, J. J., Dial, E. J., Illich, P. A., Walters, E. T. Zwitterionic phospholipids enhance aspirin's therapeutic activity as demonstrated in rodent model systems. *J. Pharm. Exp. Therap.* in press (1996).
26. Lichtenberger, L. M., Wang, Z. M., Romero J. J., Ulloa, C., Perez, J. C., Giraud, M. N., Barreto, J. C. Non-steroidal anti-inflammatory drugs (NSAIDs) associate with zwitterionic phospholipids: Insight into the mechanism and reversal of NSAID-induced gastrointestinal injury. *Natural Medicine* 1, 154–158 (1995).
27. Ligumsky, M., Grossman, M. I. & Kauffman, Jr., G. L. Endogenous gastric mucosal prostaglandins: their role in mucosal integrity. *Am. J. Physiol.* 242, G337–341 (1982).
28. McCormack, K. & Brune, K. Classical absorption theory and the development of gastric mucosal damage associated with non-steroidal anti-inflammatory drugs. *Arch. Toxicol.* 60, 261–269 (1987).
29. Mojaverian, P., Rocci, Jr., M. L., Conner, D. P., Abrams, W. B. & Vlasses, P. H. Effect of food on the absorption of enteric-coated aspirin: Correlation with gastric residence time. *Clin. Pharm. Ther.* 41, 11–17 (1987).
30. U.S. Pat. No. 4,369,182
31. U.S. Pat. No. 4,421,747
32. U.S. Pat. No. 4,309,402
33. Rainsford, K. D. *Antiinflammatory and Anti-rheumatic Drugs* I, CRC Press, Boca Raton, Fla., (1985).
34. Rainsford, K. D. Mechanism of gastrointestinal toxicity of non-steroidal anti-inflammatory drugs. *Scand. J. Gastroenterol.* 24 (suppl. 163), 9–16 (1989).
35. Randall, L. O., Selitto, J. J. A method for measurement of analgesic activity of inflamed tissue. *Arch. Int. Pharmacodyn.* 111, 409–419, (1957).
36. Scheiman, J. M., Behler, E. M., Loeffler, K. M., Elta, G. H. Omeprazole ameliorates aspirin induced gastroduodenal injury. *Dig. Dis. Sci.* 39, 97–103 (1994).
37. Ucelay, M., Lasheras, B. & Cenarruzabeitia, E. Pharmacological study of the new nonsteroidal anti-inflammatory agent, 4'-Acetamidophenyl-2-(5'-p-toluyl-1'-methylpyrrole) acetate. *Arzheim-Forsch/Drug Research* 38, 546–551 (1988).
38. Whittle, B. J. R. Temoral relationship between cyclooxygenase inhibition, as measured by prostacyclin biosynthesis and the gastrointestinal damage induced by indomethacin in the rat. *Gastroenterology* 80, 94–98 (1981).
39. Whittle, B. J. R., Higgs, G. A., Eakins, K. E., Moncada, S. & Vane, J. R. Selective inhibition of prostaglandin production in inflammatory exudates and gastric mucosa. *Nature* 284, 271–273 (1980).
40. Willard, J. E., Lange, R. A. and Hillis, L. D. The use of aspirin in ischemic heart disease. *N. Engl. J. Med.* 327, 175–181 (1992).

What is claimed is:

1. A method for maintaining or enhancing therapeutic activity of a non-steroidal anti-inflammatory drug in the presence of a drug which inhibits or reduces gastric acid secretion comprising:
   administering a combination of a non-steroidal anti-inflammatory agent and a zwitterionic phospholipid to an animal.

2. The method of claim 1 wherein the drug which inhibits or reduces gastric acid secretion is omeprazole.

3. The method of claim 1 wherein the non-steroidal anti-inflammatory agent is salicylate, naproxen, indomethacine, dichlofenac, aspirin or a mixture thereof.

4. A method for maintaining or enhancing therapeutic activity of a non-steroidal anti-inflammatory drug in the presence of an H2 receptor blocker comprising:

administering an anti-inflammatory agent in association with a zwitterionic phospholipid, wherein the pH is increased above fasting levels in the animal.

5. The method of claim 4 wherein the H2 receptor blocker is ranitidine or cimetidine.

6. The method of claim 4 wherein fasting levels are about pH 1 to about pH 4.

7. A method for maintaining or enhancing the bioavailability of a non-steroidal anti-inflammatory agent in the presence of an anti-secretory agent, comprising:

administering a combination of a non-steroidal anti-inflammatory agent and a zwitterionic phospholipid to an animal, wherein the pharmacological activity of the non-steroidal anti-inflammatory agent is greater than the pharmacological activity of the non-steroidal anti-inflammatory agent in the absence of a zwitterionic phospholipid to an animal receiving an anti-secretory agent.

8. The method of claim 1, 4 or 7 wherein the composition is further defined as comprising an equimolar amount of zwitterionic phospholipid and non-steroidal anti-inflammatory drug.

9. The method of claim 1, 4 or 7 wherein the non-steroidal anti-inflammatory drug is salicylate, naproxen, indomethacin, diclofenac, aspirin, or a mixture thereof.

10. The method of claim 1, 4 or 7 wherein the zwitterionic phospholipid is dipalmitoyl phosphatidyl choline.

11. The method of claim 1, 4 or 7 wherein the composition further comprises a neutral lipid.

12. The method of claim 10 wherein the neutral lipid is a triglyceride.

13. The method of claim 7 wherein the therapeutic activity of the non-steroidal anti-inflammatory agent is enhanced.

14. A pharmaceutical preparation comprising a non-covalently associated combination of non-steroidal anti-inflammatory agent, zwitterionic phospholipid, and anti-secretory agent, wherein a ratio weight of phospholipid: non-steroidal anti-inflammatory agent about 0.1:1.0 to 10:1 is included in the pharmaceutical preparation.

15. The pharmaceutical preparation of claim 14 wherein the zwitterionic phospholipid is dipalmitoyl phosphatidyl choline and the neutral lipid is tripalmitin.

16. The pharmaceutical preparation of claim 14 wherein the antisecretory agent is omeprazole.

* * * * *

UNITED STATES PATENT AND TRADEMARK OFFICE
CERTIFICATE OF CORRECTION

PATENT NO. : 5,955,451
DATED : September 21, 1999
INVENTOR(S) : Lenard Lichtenberger and Bruce D. Butler It is certified that error appears in the above-identified patent and that said Letters Patent is hereby corrected as shown below:

Claim 14, page 32, line 13, before "pharmaceutical preparation" insert --non-gel--;

Claim 15, page 32, line 19, before "pharmaceutical preparation" insert --non-gel--;

Claim 16, page 32, line 22, before "pharmaceutical preparation" insert --non-gel--;

Signed and Sealed this

Twenty-first Day of March, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

| | | |
|---|---|---|
| PATENT NO. | : 5,955,451 | Page 1 of 1 |
| APPLICATION NO. | : 08/719134 | |
| DATED | : September 21, 1999 | |
| INVENTOR(S) | : Lenard Lichtenberger and Bruce D. Butler | |

It is certified that error appears in the above-identified patent and that said Letters Patent is hereby corrected as shown below:

In Column 1, Lines 9, 10 and 11 should be deleted and replaced with the following:

This invention was made with government support under Grant No. DK033239 awarded by the National Institutes of Health. The government has certain rights in the invention.

Signed and Sealed this
Eighth Day of March, 2011

David J. Kappos
*Director of the United States Patent and Trademark Office*